United States Patent
Witters et al.

(10) Patent No.: US 11,486,004 B2
(45) Date of Patent: Nov. 1, 2022

(54) METHODS OF SEQUENCING CIRCULAR TEMPLATE POLYNUCLEOTIDES

(71) Applicant: SINGULAR GENOMICS SYSTEMS, INC., La Jolla, CA (US)

(72) Inventors: Daan Witters, San Diego, CA (US); Allen Lipson, San Diego, CA (US); Eli N. Glezer, Del Mar, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

(21) Appl. No.: 17/719,214

(22) Filed: Apr. 12, 2022

(65) Prior Publication Data

US 2022/0243268 A1 Aug. 4, 2022

Related U.S. Application Data

(63) Continuation of application No. PCT/US2021/041139, filed on Jul. 9, 2021.

(60) Provisional application No. 63/051,094, filed on Jul. 13, 2020.

(51) Int. Cl.
  *C12P 19/34* (2006.01)
  *C12Q 1/6874* (2018.01)
(52) U.S. Cl.
  CPC .................... *C12Q 1/6874* (2013.01)
(58) Field of Classification Search
  CPC .................................................. C12Q 1/686
  See application file for complete search history.

(56) References Cited

U.S. PATENT DOCUMENTS

| | | | |
|---|---|---|---|
| 4,318,846 A | 3/1982 | Khanna et al. |
| 5,034,506 A | 7/1991 | Summerton et al. |
| 5,066,580 A | 11/1991 | Lee |
| 5,188,934 A | 2/1993 | Menchen et al. |
| 5,235,033 A | 8/1993 | Summerton et al. |
| 5,366,860 A | 11/1994 | Bergot et al. |
| 5,426,180 A | 6/1995 | Kool |
| 5,599,675 A | 2/1997 | Brenner |
| 5,641,658 A | 6/1997 | Adams et al. |
| 5,688,648 A | 11/1997 | Mathies et al. |
| 5,750,341 A | 5/1998 | Macevicz |
| 5,763,594 A | 6/1998 | Hiatt et al. |
| 5,800,996 A | 9/1998 | Lee et al. |
| 5,808,045 A | 9/1998 | Hiatt et al. |

(Continued)

FOREIGN PATENT DOCUMENTS

| | | |
|---|---|---|
| WO | WO 1989/010977 A1 | 11/1989 |
| WO | WO1996/007669 A1 | 3/1996 |

(Continued)

OTHER PUBLICATIONS

Bains, W. et al. (Dec. 7, 1988). "A novel method for nucleic acid sequence determination," J Theor Biol 135(3):303-307.

(Continued)

*Primary Examiner* — Kenneth R Horlick
(74) *Attorney, Agent, or Firm* — Mintz, Levin, Cohn, Ferris, Glovsky and Popeo, P.C.

(57) ABSTRACT

Disclosed herein, inter alia, are complexes, kits, and efficient methods of sequencing two strands of a double stranded polynucleotide. In embodiments, methods of sequencing a circular template polynucleotide are provided including generating immobilized extension products.

30 Claims, 8 Drawing Sheets

Specification includes a Sequence Listing.

(56) References Cited

U.S. PATENT DOCUMENTS

| | | | |
|---|---|---|---|
| 5,847,162 | A | 12/1998 | Lee et al. |
| 5,872,244 | A | 2/1999 | Hiatt et al. |
| 6,210,891 | B1 | 4/2001 | Nyren et al. |
| 6,232,465 | B1 | 5/2001 | Hiatt et al. |
| 6,258,568 | B1 | 7/2001 | Nyren |
| 6,274,320 | B1 | 8/2001 | Rothberg et al. |
| 6,664,079 | B2 | 12/2003 | Ju et al. |
| 7,057,026 | B2 | 6/2006 | Barnes et al. |
| 7,115,400 | B1 | 10/2006 | Adessi et al. |
| 7,541,444 | B2 | 6/2009 | Milton et al. |
| 7,790,418 | B2 | 9/2010 | Mayer |
| 8,003,354 | B2 | 8/2011 | Shen et al. |
| 8,178,360 | B2 | 5/2012 | Barnes et al. |
| 10,738,072 | B1 | 8/2020 | Graham et al. |
| 2008/0009420 | A1 | 1/2008 | Scroth et al. |
| 2009/0118128 | A1 | 5/2009 | Liu et al. |
| 2011/0065151 | A1 | 3/2011 | Kumar et al. |
| 2013/0012399 | A1 | 1/2013 | Myers et al. |
| 2014/0322759 | A1 | 10/2014 | Skirgaila et al. |
| 2015/0017635 | A1 | 1/2015 | Myllykangas et al. |
| 2016/0116384 | A1 | 4/2016 | Chen et al. |
| 2016/0272954 | A1 | 9/2016 | Li et al. |
| 2017/0159136 | A1 | 6/2017 | Church et al. |
| 2018/0002735 | A1 | 1/2018 | Drmanac et al. |
| 2018/0274024 | A1 | 9/2018 | Ju et al. |
| 2019/0032128 | A1* | 1/2019 | Chen ............... C12Q 1/6809 |
| 2019/0352327 | A1 | 11/2019 | Wu et al. |
| 2021/0032618 | A1 | 2/2021 | Driscoll et al. |
| 2021/0189460 | A1* | 6/2021 | Hosono ............ C12Q 1/6869 |

FOREIGN PATENT DOCUMENTS

| | | |
|---|---|---|
| WO | WO 2004/018497 A2 | 3/2004 |
| WO | WO 2004/018497 A3 | 3/2004 |
| WO | WO 2017/205336 A1 | 11/2017 |
| WO | WO 2018/148723 A1 | 8/2018 |
| WO | WO 2019/086531 A1 | 5/2019 |
| WO | WO 2020/056044 A1 | 3/2020 |

OTHER PUBLICATIONS

Beattie, W. et al. (1995) "Hybridization of DNA targets to glass-tethered oligonucleotide probes." Molecular biotechnology 4(3): 213.

Bentley, DR. et al. (Nov. 6, 2008). "Accurate whole human genome sequencing using reversible terminator chemistry," Nature 456(7218):53-59.

Chen, F. et al. (2015) "Expansion microscopy." Science 347(6221): 543.

Chen, KH. et al. (2015) RNA imaging. Spatially resolved, highly multiplexed RNA profiling in single cells. Science. 348: aaa6090.

Christian, AT et al. (2001) Proc Natl Acad Sci USA. 98(25):14238-14243.

Dolinnaya, N. et al. (Nov. 25, 1993) "Oligonucleotide circularization by template-directed chemical ligation," Nucleic Acids Research, vol. 21:23, 5403-5407.

Drmanac, S. et al. (Jan. 1998). "Accurate sequencing by hybridization for DNA diagnostics and individual genomics," Nat Biotechnol 16(1):54-58.

Feeney, R. et al. (Apr. 1, 1982) Modification of Proteins; Advances in Chemistry, vol. 198, American Chemical Society.

Fodor, SPA. et al. (Feb. 15, 1991). "Light-directed, spatially addressable parallel chemical synthesis," Science 251(4995):767-773.

International Search Report dated Dec. 30, 2021, for PCT Application No. PCT/US2021/41139, filed Jul. 9, 2021, 5 pages.

Kershaw, CJ., and O'Keefe, RT. (2012) "Splint ligation of RNA with T4 DNA ligase." Methods Mol Biol. 941: 257-269. 10.1007/978-1-62703-113-4_19.

Lage, J. et al. (Mar. 2003) Genome Research 13(2):294-307.

Larsson, C. et al. (2010) "In situ detection and genotyping of individual mRNA molecules." Nature methods 7(5): 395-397.

Lee, JH et al. (2015) "Fluorescent in situ sequencing (FISSEQ) of RNA for gene expression profiling in intact cells and tissues." Nature protocols 10(3): 442-458.

Lizardi, PM. et al. (Jul. 1998) "Mutation detection and single-molecule counting using isothermal rolling-circle amplification," Nat. Genet. 19(3):225.

Mag, M. et al. (Nov. 24, 1992) Tetrahedron letters 33.48: 7319-7322.

Nilsson, M. et al. (1994) "Padlock Probes: Circularizing Oligonucleotides for Localized DNA Detection" Science, vol. 265 Issue 5181:2085-2088.

Rattray, AJ. and Strathern, JN. (2003) "Error-prone DNA polymerases: when making a mistake is the only way to get ahead." Annual review of genetics 37.1: 31-66.

Ronaghi, M. et al. (1996) "Real-time DNA sequencing using detection of pyrophosphate release." Analytical biochemistry 242(1): 84-89.

Ronaghi, M. et al. (Jul. 17, 1998). "A sequencing method based on real-time pyrophosphate," Science 281 (5375):363-365.

Ronaghi, M. (Jan. 2001). "Pyrosequencing sheds light on DNA sequencing," Genome Res 11(1):3-11.

Rubin, E. et al. (1995) "Convergent DNA synthesis: a non-enzymatic dimerization approach to circular oligodeoxynucleotides." Nucleic acids research 23.17: 3547-3553.

Sansone, A. (2019) "Spatial transcriptomics levels up." Nature Methods 16(6): 458.

Shendure, J. et al. (2005) "Accurate multiplex polony sequencing of an evolved bacterial genome," Science 309(5741):1728-1732.

Southworth, MW. et al. (1996) PNAS (93)11: 8281-8285.

Walker, JW. et al. (1988) Journal of the American Chemical Society 110.21: 7170-7177.

Wang, G. et al. (2018). "Multiplexed imaging of high-density libraries of RNAs with MERFISH and expansion microscopy." Scientific reports 8:4847.

Wang, X. et al. (2018) "Three-dimensional intact-tissue sequencing of single-cell transcriptional states." Science 361.6400: eaat5691.

* cited by examiner

METHODS OF SEQUENCING CIRCULAR TEMPLATE POLYNUCLEOTIDES

CROSS-REFERENCE TO RELATED APPLICATIONS

This application claims the benefit of U.S. Provisional Application No. 63/051,094, filed Jul. 13, 2020 which is incorporated herein by reference in its entirety and for all purposes.

REFERENCE TO SEQUENCE LISTING SUBMITTED ELECTRONICALLY

The Sequence Listing titled 051385-528001WO_SL_ST25.TXT, was created on Jul. 3, 2021 in machine format IBM-PC, MS-Windows operating system, is 4,822 bytes in size, and is hereby incorporated by reference in its entirety for all purposes.

BACKGROUND

Genetic analysis is taking on increasing importance in modern society as a diagnostic, prognostic, and forensic tool. DNA sequencing is a fundamental tool in biological and medical research; it is an essential technology for the paradigm of personalized precision medicine. Sanger sequencing, where the sequence of a nucleic acid is determined by selective incorporation and detection of dideoxynucleotides, enabled the mapping of the first human reference genome. While this methodology is still useful for validating newer sequencing technologies, efforts to sequence and assemble genomes using the Sanger method are an expensive and laborious undertaking, requiring specialized equipment and expertise. Next generation sequencing (NGS) methodologies make use of simultaneously sequencing millions of fragments of nucleic acids in a single run. However, traditional next generation sequencing still has shortcomings, such as challenges with detecting rare sequence variants in the context of polymerase errors. Sequencing two strands of the sample dsDNA template, sometimes referred to as paired-end, paired-strand, linked-strand, or dual-read sequencing, is performed in some NGS workflows. In typical paired-end workflows, one strand of the dsDNA template is removed (e.g., referred to as linearization of dsDNA) and a first sequencing read is performed. Following additional amplification steps after the first sequencing read (such as additional rounds of bridge PCR or another amplification process), a regenerated second strand may then be sequenced. These steps add complexity, cost, and time to the DNA sequencing workflow and can also introduce additional errors made by the polymerase used during solid phase amplification.

SUMMARY

In view of the foregoing, innovative approaches to address issues with existing sequencing technologies are needed. Disclosed herein are solutions to these and other problems in the art which, in embodiments, reduce the number of workflow steps needed to execute paired-end sequencing, and increase the fidelity and accuracy of high throughput sequencing methods. In certain embodiments, the compositions and methods provided herein reduce the amount of nucleic acid manipulation and duplication required by traditional next generation sequencing techniques. Prior to the present disclosure, cluster-based sequencing processes would include cleaving and removing one strand from double-stranded molecules in a cluster before generating a first read, without which the second strand would effectively compete with hybridization of the sequencing primer. Generating a sequencing read for the second (cleaved) strand would then require creating a new complementary strand from the sequenced first strand (i.e., a new second strand). In accordance with various embodiments, methods disclosed herein permit reading of the original first and second strands, reducing the time, reagents, expense, and risk of polymerase error inherent in previous methods.

In an aspect is provided a method of sequencing a template polynucleotide. In embodiments, the method includes: (A) generating a partially double-stranded amplification product including a first strand hybridized to a second strand, wherein (i) the partially double-stranded amplification product includes one or more copies (e.g., multiple copies) of the template polynucleotide, and (ii) the first strand and second strand are both covalently attached to a solid surface; (B) generating a first sequencing read by hybridizing one or more first sequencing primers to a single-stranded portion of the first strand, and extending the one or more first sequencing primers; and (C) generating a second sequencing read by hybridizing one or more second sequencing primers to the second strand, and extending the one or more second sequencing primers.

In an aspect, provided herein is a complex including a polynucleotide and a solid support. In embodiments, the complex includes one or more elements described herein with regard to any of the various methods described herein. In embodiments the complex includes (a) a partially double-stranded amplification product including a first strand hybridized to a second strand, wherein (i) the partially double-stranded amplification product includes multiple copies of a template polynucleotide, and (ii) the first strand and second strand are both covalently attached to a solid surface; and (b) one or more first sequencing primer extension products hybridized to a single-stranded portion of the first strand, wherein the sequencing primer extension product includes a modified nucleotide; and (c) one or more polymerases.

BRIEF DESCRIPTION OF THE DRAWINGS

FIG. 4A depicts a fixed cellular matrix 400 including a nucleus 410 and nucleic acids 415. FIG. 4B depicts annealing of a target-specific probe 416 to one of nucleic acids 415 from FIG. 4A. FIG. 4C depicts ligation and circularization of probe 416 from FIG. 4B to generate circularized oligonucleotide 417. FIG. 4D depicts annealing of the circularized oligonucleotide to an immobilized primer 425 attached to cellular component (or matrix) 420.

FIG. 4E depicts a first step of extension and amplification of the circularized oligo to generate an immobilized amplicon 418. After the amplification and denaturation steps described herein, for example in FIG. 1, the 3' ends of the hybridized strands 419 are blocked, as shown in FIG. 4F. FIG. 4G depicts subsequent sequencing primer annealing and initiation of sequencing. Note that cellular components and oligos are not drawn to scale and are spread apart for clarity of illustration.

DETAILED DESCRIPTION

Figure 1A:
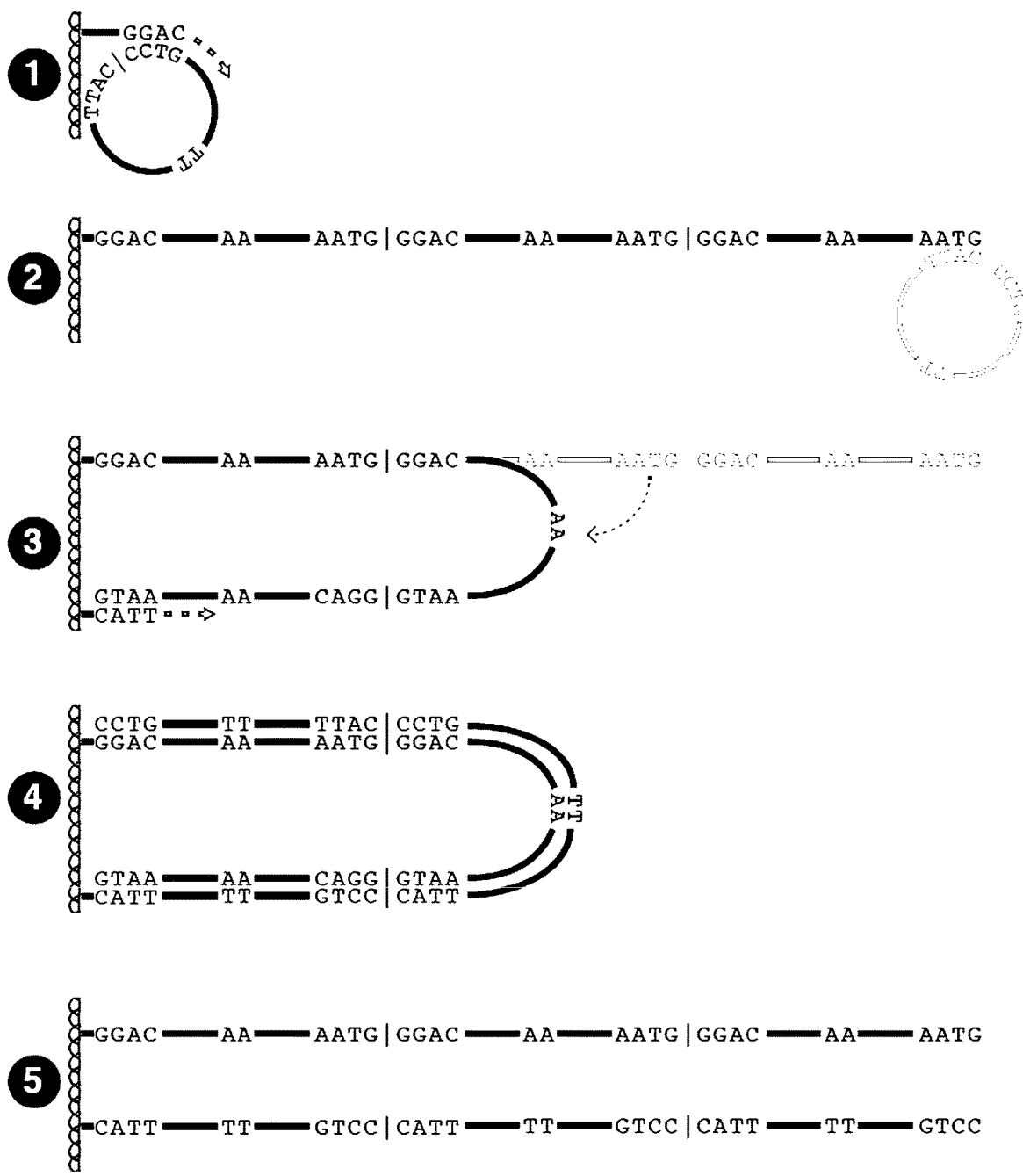
FIGS. 1A-1C. Generalized illustration depicting a sequencing method in accordance with some embodiments. Step 1) shows the hybridization of a circular template polynucleotide to a tethered oligo primer. Step 2) depicts the elongation (i.e., extension) of the tether oligo primer into a concatemer of the circular template. Step 3) shows the bridging over and step 4) shows the extension of a second tether oligo primer to form complementary concatemer strands. After step 5), showing a denaturation step, it is possible in step 6) (starting in FIG. 1B) to imperfectly rehybridize the strands, leaving regions single stranded. After step 7) blocking 3' ends, it is possible to hybridize the first sequencing primer to begin sequencing (step 8). Step 9) shows that after the completion of the first read, this strand can then be optionally cleaved, leaving the second strand fully available for hybridization of the second sequencing primer, for completion of the second read (steps 10 and 11 are shown in FIG. 1C). For illustrative purposes, the bars between defined sequences, representing portions of a template sequence, are 25 nucleotides in length. Alternative template lengths are contemplated herein, in accordance with various embodiments. Sequences illustrated in FIGS. 1A-1C include SEQ ID NOs: 3-7.
Figure 1B:
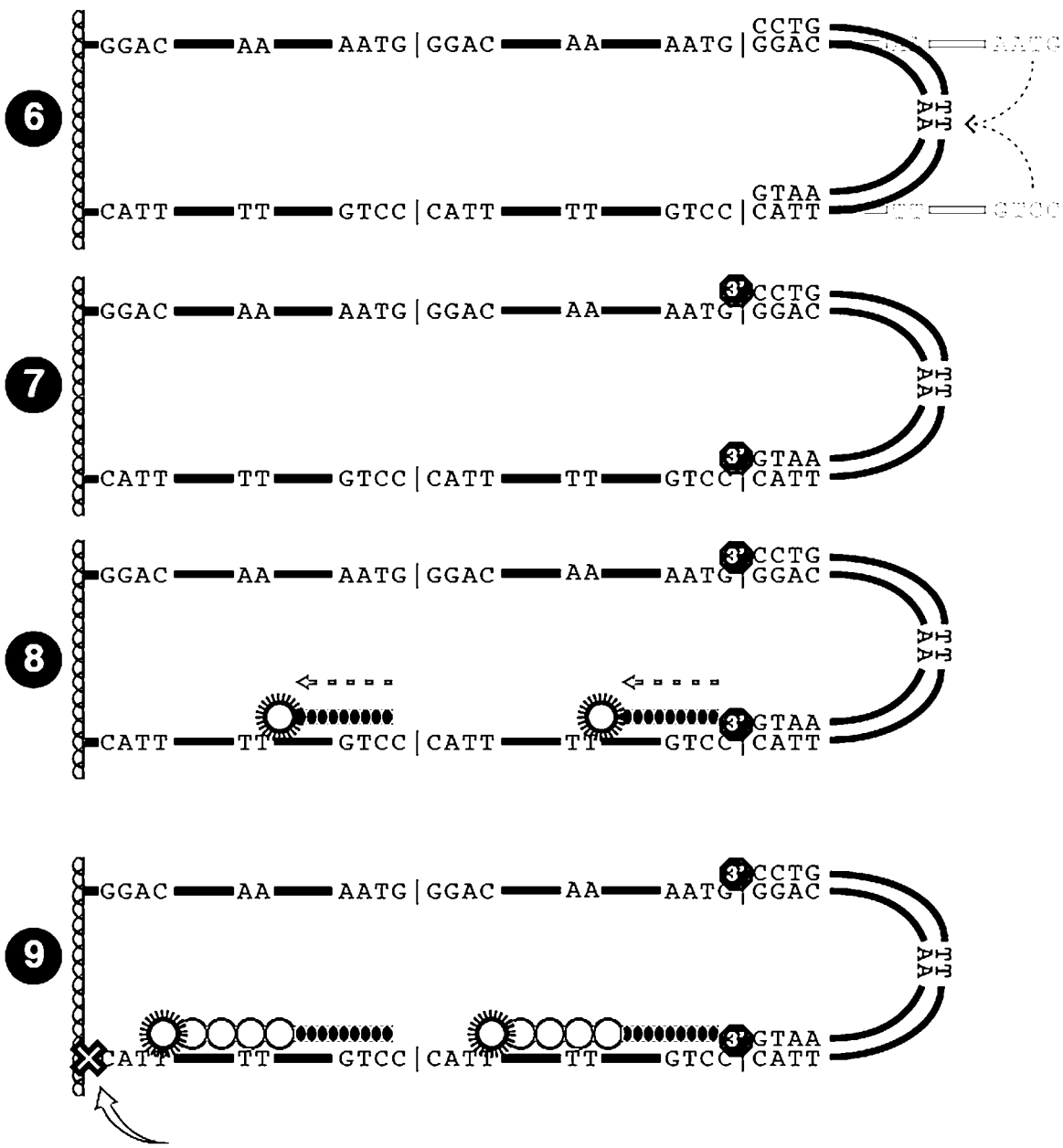
Figure 1C:
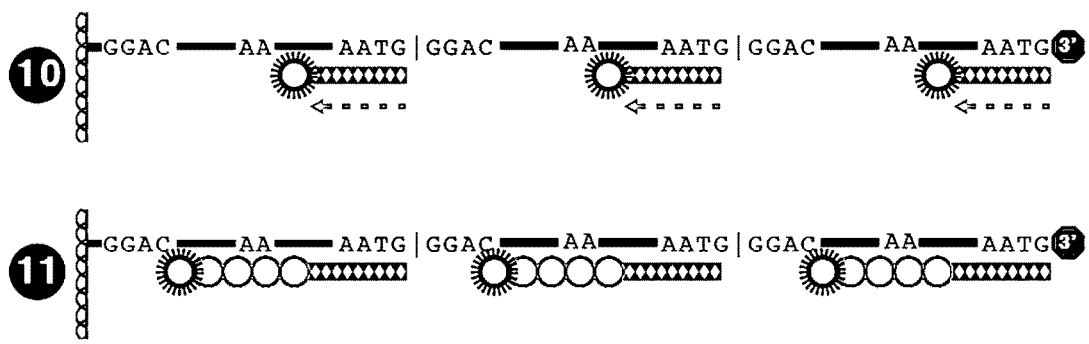

A key feature of some embodiments of methods disclosed herein is that following amplification, two sequencing reads can occur in the same cluster or colony on a clustered array with minimal intervening steps between the first and second read. The terms "cluster" and "colony" are used interchangeably throughout this application and refer to a discrete site on a solid support or within a cell comprised of a plurality of immobilized nucleic acid strands. The term "clustered array" refers to an array formed from such clusters or colonies.

Definitions

The practice of the technology described herein will employ, unless indicated specifically to the contrary, conventional methods of chemistry, biochemistry, organic chemistry, molecular biology, bioinformatics, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, N.Y. 1994); and Sambrook and Green, Molecular Cloning: A Laboratory Manual, 4th Edition (2012). Methods, devices and materials similar or equivalent to those described herein can be used in the practice of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise.

Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are "tethered", "coated", "attached", or "immobilized" to one another or to a common solid or semisolid support. An association may refer to covalent or non-covalent means for attaching labels to solid or semi-solid supports such as beads. In embodiments, primers on or bound to a solid support are covalently attached to the solid support. An association may comprise hybridization between a target and a label.

As used herein, the term "complementary" or "substantially complementary" refers to the hybridization, base pairing, or the formation of a duplex between nucleotides or nucleic acids. For example, complementarity exists between the two strands of a double stranded DNA molecule or between an oligonucleotide primer and a primer binding site on a single stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g. chemical compounds including biomolecules or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, a protein or enzyme.

"Hybridize" shall mean the annealing of a nucleic acid sequence to another nucleic acid sequence (e.g., one single-stranded nucleic acid (such as a primer) to another nucleic acid) based on the well-understood principle of sequence complementarity. In an embodiment the other nucleic acid is a single-stranded nucleic acid. In some embodiments, one portion of a nucleic acid hybridizes to itself, such as in the formation of a hairpin structure. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acid. For example, specific hybridization includes the hybridization of a primer or capture nucleic acid to a portion of a target nucleic acid (e.g., a template, or adapter portion of a template) that is substantially complementary to the primer or capture nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which comprises a double stranded portion of nucleic acid.

A nucleic acid can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction comprises a suitable thermal stable polymerase. Thermal stable polymerases are known in the art and are stable for prolonged periods of time, at temperature greater than 80° C. when compared to common polymerases found in most mammals. In certain embodiments the term "amplified" refers to a method that comprises a polymerase chain reaction (PCR). Conditions conducive to amplification (i.e., amplification conditions) often comprise at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to branched and hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

A nucleic acid can be amplified by a thermocycling method or by an isothermal amplification method. In some embodiments a rolling circle amplification method is used. In some embodiments, amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface or substrate. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge PCR amplification, emulsion PCR, WildFire amplification (e.g., US patent publication US20130012399), and the like, or combinations thereof.

As used herein, the term "nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides.

As used herein, the terms "polynucleotide primer" and "primer" refers to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

In some embodiments, a nucleic acid comprises a capture nucleic acid. A capture nucleic acid refers to a nucleic acid that is attached to a substrate. In some embodiments, a capture nucleic acid comprises a primer. In some embodiments, a capture nucleic acid is a nucleic acid configured to specifically hybridize to a portion of one or more nucleic acid templates (e.g., a template of a library). In some embodiments a capture nucleic acid configured to specifically hybridize to a portion of one or more nucleic acid templates is substantially complementary to a suitable portion of a nucleic acid template, or an amplicon thereof. In some embodiments a capture nucleic acid is configured to specifically hybridize to a portion of an adapter, or a complement thereof. In some embodiments a capture nucleic acid, or portion thereof, is substantially complementary to a portion of an adapter, or a complement thereof. In embodiments, a capture nucleic acid is a probe oligonucleotide. Typically, a probe oligonucleotide is complementary to a target polynucleotide or portion thereof, and further comprises a label (such as a binding moiety) or is attached to a surface, such that hybridization to the probe oligonucleotide permits the selective isolation of probe-bound polynucleotides from unbound polynucleotides in a population. A probe oligonucleotide may or may not also be used as a primer.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s).

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analog" or "analogue", in reference to a chemical compound, refers to compound having a structure similar to that of another one, but differing from it in respect of one or more different atoms, functional groups, or substructures that are replaced with one or more other atoms, functional groups, or substructures. In the context of a nucleotide useful in practicing the invention, a nucleotide analog refers to a compound that, like the nucleotide of which it is an analog, can be incorporated into a nucleic acid molecule (e.g., an extension product) by a suitable polymerase, for example, a DNA polymerase in the context of a dNTP analogue. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine.; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, the term "native nucleotide" is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

In embodiments, the nucleotides of the present disclosure use a cleavable linker to attach the label to the nucleotide. The use of a cleavable linker ensures that the label can, if required, be removed after detection, avoiding any interfering signal with any labelled nucleotide incorporated subsequently. The use of the term "cleavable linker" is not meant to imply that the whole linker is required to be removed from the nucleotide base. The cleavage site can be located at a position on the linker that ensures that part of the linker remains attached to the nucleotide base after cleavage. The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine. The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or formamidopyrimidine DNA glycosylase (Fpg). In embodiments, the scissile linkage site includes a sequence-specific nicking site having a nucleotide sequence that is recognized and nicked by a nicking endonuclease enzyme or a uracil DNA glycosylase.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, the blocking moiety is attached to the 3' oxygen of the nucleotide and is independently

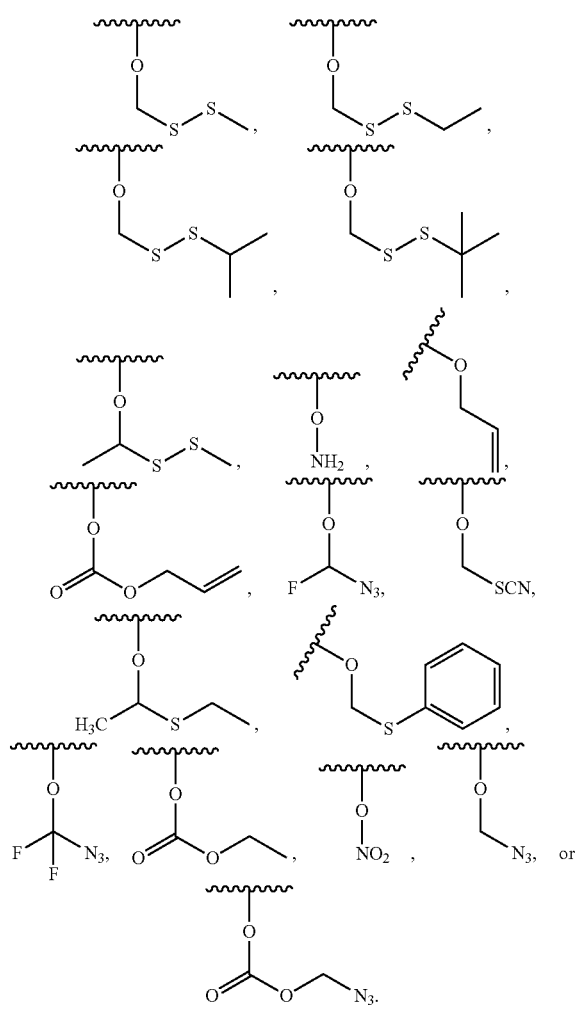

A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes.

As used herein, the terms "blocking moiety," "reversible blocking group," "reversible terminator" and "reversible terminator moiety" are used in accordance with their plain and ordinary meanings and refer to a cleavable moiety which does not interfere with incorporation of a nucleotide comprising it by a polymerase (e.g., DNA polymerase, modified DNA polymerase), but prevents further strand extension until removed ("unblocked"). For example, a reversible terminator may refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Suitable nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group may be represented as —OR [reversible terminating (capping) group], wherein O is the oxygen atom of the 3'-OH of the pentose and R is the blocking group, while the label is linked to the base, which acts as a reporter and can be cleaved. 3'-O-blocked reversible terminators are known in the art, and may be, for instance, a 3'-ONH$_2$ reversible terminator, a 3'-O-allyl reversible terminator, or a 3'-0-azidomethyl reversible terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "label" or "labels" generally refer to molecules that can directly or indirectly produce or result in a detectable signal either by themselves or upon interaction with another molecule. Non-limiting examples of detectable labels include labels comprising fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.).

As used herein, the terms "solid support" and "substrate" and "solid surface" refers to discrete solid or semi-solid surfaces to which a plurality of primers may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A solid support may be used interchangeably with the term "bead." A solid support may further comprise a polymer or hydrogel on the surface to which the primers are attached. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid supports for some embodiments have at least one surface located within a flow cell. The solid support, or regions thereof, can be substantially flat. The solid support can have surface features such as wells, pits, channels, ridges, raised regions, pegs, posts or the like. The term solid support is encompassing of a substrate (e.g., a flow cell) having a surface comprising a polymer coating covalently attached thereto. In embodiments, the solid support is a flow cell. The term "flowcell" as used herein refers to a chamber including a solid surface across which one or more fluid reagents can be flowed. Examples of flowcells and related fluidic systems and detection platforms that can be readily used in the methods of the present disclosure are described, for example, in Bentley et al., Nature 456:53-59 (2008). In certain embodiments a substrate comprises a surface (e.g., a surface of a flow cell, a surface of a tube, a surface of a chip), for example a metal surface (e.g. steel, gold, silver, aluminum, silicon and copper). In some embodiments a substrate (e.g., a substrate surface) is coated and/or comprises functional groups and/or inert materials. In certain embodiments a substrate comprises a bead, a chip, a capillary, a plate, a membrane, a wafer (e.g., silicon wafers), a comb, or a pin for example. In some embodiments a substrate comprises a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, glass, nylon, Wang resin, Merrifield resin, metal (e.g., iron, a metal alloy, sepharose, agarose, polyacrylamide, dextran, cellulose and the like or combinations thereof. In some embodiments a substrate comprises a magnetic material (e.g., iron, nickel, cobalt, platinum, aluminum, and the like). In certain embodiments a substrate comprises a magnetic bead (e.g., DYNABEADS®, hematite, AMPure XP). Magnets can be used to purify and/or capture nucleic acids bound to certain substrates (e.g., substrates comprising a metal or magnetic material).

As used herein, the terms "cluster" and "colony" are used interchangeably to refer to a discrete site on a solid support or within a cell that includes a plurality of immobilized polynucleotides and a plurality of immobilized complementary polynucleotides. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/$cm^2$, at least about 1,000 features/$cm^2$, at least about 10,000 features/$cm^2$, at least about 100,000 features/$cm^2$, at least about 10,000,000 features/$cm^2$, at least about 100,000,000 features/$cm^2$, at least about 1,000,000,000 features/$cm^2$, at least about 2,000,000,000 features/$cm^2$ or higher. In embodiments, the arrays have features at any of a variety of densities including, for example, at least about 10 features/$cm^2$, 100 features/$cm^2$, 500 features/$cm^2$, 1,000 features/$cm^2$, 5,000 features/$cm^2$, 10,000 features/$cm^2$, 50,000 features/$cm^2$, 100,000 features/$cm^2$, 1,000,000 features/$cm^2$, 5,000,000 features/$cm^2$, or higher.

As used herein, the term "selective" or "selectivity" or the like of a compound refers to the compound's ability to discriminate between molecular targets. For example, a chemical reagent may selectively modify one nucleotide type in that it reacts with one nucleotide type (e.g., cytosines) and not other nucleotide types (e.g., adenine, thymine, or guanine). When used in the context of sequencing, such as in "selectively sequencing," this term refers to sequencing one or more target polynucleotides from an original starting population of polynucleotides, and not sequencing non-target polynucleotides from the starting population. Typically, selectively sequencing one or more target polynucleotides involves differentially manipulating the target polynucleotides based on known sequence. For example, target polynucleotides may be hybridized to a probe oligonucleotide that may be labeled (such as with a member of a binding pair) or bound to a surface. In embodiments, hybridizing a target polynucleotide to a probe oligonucleotide includes the step of displacing one strand of a double-stranded nucleic acid. Probe-hybridized target polynucleotides may then be separated from non-hybridized polynucleotides, such as by removing probe-bound polynucleotides from the starting population or by washing away polynucleotides that are not bound to a probe. The result is a selected subset of the starting population of polynucleotides, which is then subjected to sequencing, thereby selectively sequencing the one or more target polynucleotides.

As used herein, the terms "specific", "specifically", "specificity", or the like of a compound refers to the compound's ability to cause a particular action, such as binding, to a particular molecular target with minimal or no action to other proteins in the cell.

In some embodiments, a nucleic acid (e.g., an adapter or a primer) includes a molecular identifier or a molecular barcode. As used herein, the term "molecular barcode" (which may be referred to as a "tag", a "barcode", a "molecular identifier", an "identifier sequence" or a "unique molecular identifier" (UMI)) refers to any material (e.g., a nucleotide sequence, a nucleic acid molecule feature) that is capable of distinguishing an individual molecule in a large heterogeneous population of molecules. In embodiments, a barcode is unique in a pool of barcodes that differ from one another in sequence, or is uniquely associated with a particular sample polynucleotide in a pool of sample polynucleotides. In embodiments, every barcode in a pool of adapters is unique, such that sequencing reads including the barcode can be identified as originating from a single sample polynucleotide molecule on the basis of the barcode alone. In other embodiments, individual barcode sequences may be used more than once, but adapters including the duplicate barcodes are associated with different sequences and/or in different combinations of barcoded adaptors, such that sequence reads may still be uniquely distinguished as originating from a single sample polynucleotide molecule on the basis of a barcode and adjacent sequence information (e.g., sample polynucleotide sequence, and/or one or more adjacent barcodes). In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are about 10 to about 50 nucleotides in length, such as about 15 to about 40, or about 20 to about 30 nucleotides in length. In a pool of different barcodes, barcodes may have the same or different lengths. In general, barcodes are of sufficient length and include sequences that are sufficiently different to allow the identification of sequencing reads that originate from the same sample polynucleotide molecule. In embodiments, each barcode in a plurality of barcodes differs from every other barcode in the plurality by at least three nucleotide positions, such as at least 3, 4, 5, 6, 7, 8, 9, 10, or more nucleotide positions. In some embodiments, substantially degenerate barcodes may be known as random. In some embodiments, a barcode may include a nucleic acid sequence from within a pool of known sequences. In some embodiments, the barcodes may be pre-defined.

In embodiments, a nucleic acid (e.g., an adapter or primer) includes a sample barcode. In general, a "sample barcode" is a nucleotide sequence that is sufficiently different from other sample barcodes to allow the identification of the sample source based on sample barcode sequence(s) with which they are associated. In embodiments, a plurality of nucleotides (e.g., all nucleotides from a particular sample source, or sub-sample thereof) are joined to a first sample barcode, while a different plurality of nucleotides (e.g., all nucleotides from a different sample source, or different subsample) are joined to a second sample barcode, thereby associating each plurality of polynucleotides with a different sample barcode indicative of sample source. In embodiments, each sample barcode in a plurality of sample barcodes differs from every other sample barcode in the plurality by at least three nucleotide positions, such as at least 3, 4, 5, 6, 7, 8, 9, 10, or more nucleotide positions. In some embodiments, substantially degenerate sample barcodes may be known as random. In some embodiments, a sample barcode may include a nucleic acid sequence from within a pool of known sequences. In some embodiments, the sample barcodes may be pre-defined. In embodiments, the sample barcode includes about 1 to about 10 nucleotides. In embodiments, the sample barcode includes about 3, 4, 5, 6, 7, 8, 9, or about 10 nucleotides. In embodiments, the sample barcode includes about 3 nucleotides. In embodiments, the sample barcode includes about 5 nucleotides. In embodiments, the sample barcode includes about 7 nucleotides. In embodiments, the sample barcode includes about 10 nucleotides. In embodiments, the sample barcode includes about 6 to about 10 nucleotides.

The terms "bind" and "bound" as used herein are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules (e.g., as in a substrate, bound to a first antibody, bound to an analyte, bound to a second antibody), thereby forming a complex. As used herein, the term "attached" refers to the state of two things being joined, fastened, adhered, connected or bound to each other. For example, a nucleic acid, can be attached to a material, such as a hydrogel, polymer, or solid support, by a covalent or non-covalent bond. In embodiments, attachment is a covalent attachment.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

As used herein, the terms "sequencing", "sequence determination", and "determining a nucleotide sequence", are used in accordance with their ordinary meaning in the art, and refer to determination of partial as well as full sequence information of the nucleic acid being sequenced (e.g., a template nucleic acid), and particular physical processes for generating such sequence information. That is, the term includes sequence comparisons, fingerprinting, and like levels of information about a target nucleic acid, as well as the express identification and ordering of nucleotides in a target nucleic acid. The term also includes the determination of the identification, ordering, and locations of one, two, or three of the four types of nucleotides within a target nucleic acid. In embodiments, sequencing refers to identifying the sequential nucleotides of a template nucleic acid.

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9° N polymerase or a variant thereof, E. Coli DNA polymerase I, Bacteriophage T4 DNA polymerase, Sequenase, Taq DNA polymerase, DNA polymerase from Bacillus stearothermophilus, Bst 2.0 DNA polymerase, 9° N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or or Therminator IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Therminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant P. abyssi polymerase (e.g., such as a mutant P. abyssi polymerase described in WO 2018/148723 or WO 2020/056044).

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at either the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) polynucleotide strand.

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, the term "sequencing reaction mixture" is used in accordance with its plain and ordinary meaning and refers to an aqueous mixture that contains the reagents necessary to add a nucleotide (e.g., a dNTP or dNTP analogue) to a DNA strand by a DNA polymerase. In embodiments, the sequencing reaction mixture includes a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP)

buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton X), a chelator (e.g., EDTA), and/or salts (e.g., ammonium sulfate, magnesium chloride, sodium chloride, or potassium chloride). As used herein, the term "invasion-reaction mixture" is used in accordance with its plain and ordinary meaning and refers to an aqueous mixture that contains the reagents sufficient to allow a nucleotide or nucleotide analogue to be added to a DNA strand by a DNA polymerase that extends the invasion primer.

Provided herein are methods and compositions for analyzing a sample (e.g., sequencing nucleic acids within a sample). A sample (e.g., a sample comprising nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid).

In some embodiments, a sample comprises nucleic acid, or fragments thereof. A sample can comprise nucleic acids obtained from one or more subjects. In some embodiments a sample comprises nucleic acid obtained from a single subject. In some embodiments, a sample comprises a mixture of nucleic acids. A mixture of nucleic acids can comprise two or more nucleic acid species having different nucleotide sequences, different fragment lengths, different origins (e.g., genomic origins, cell or tissue origins, subject origins, the like or combinations thereof), or combinations thereof. A sample may comprise synthetic nucleic acid.

A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

Provided herein are methods, systems, and compositions for analyzing a sample (e.g., sequencing nucleic acids within a sample) in situ. The term "in situ" is used in accordance with its ordinary meaning in the art and refers to a sample surrounded by at least a portion of its native environment, such as may preserve the relative position of two or more elements. For example, an extracted human cell is considered in situ when the cell is retained in its local microenvironment so as to avoid extracting the target (e.g., nucleic acid molecules or proteins) away from their native environment. An in situ sample (e.g., a cell) can be obtained from a suitable subject. An in situ cell sample may refer to a cell and its surrounding milieu, or a tissue. A sample can be isolated or obtained directly from a subject or part thereof. In embodiments, the methods described herein (e.g., sequencing a plurality of target nucleic acids of a cell in situ) are applied to an isolated cell (i.e., a cell not surrounded by least a portion of its native environment). For the avoidance of any doubt, when the method is performed within a cell (e.g., an isolated cell) the method may be considered in situ. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may include cells or tissues that are normal, healthy, diseased (e.g., infected), and/or cancerous (e.g., cancer cells). A sample obtained from a subject may include cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can include nucleic acids obtained from one or more subjects. In some embodiments a sample includes nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments a subject is suspected of having a genetic variation or a disease or condition associated with a genetic variation.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. In general, cells from any population can be used in the methods, such as a population of prokaryotic or eukaryotic organisms, including bacteria or yeast.

The terms "cellular component" is used in accordance with its ordinary meaning in the art and refers to any organelle, nucleic acid, protein, or analyte that is found in a prokaryotic, eukaryotic, archaeal, or other organismic cell type. Examples of cellular components (e.g., a component of a cell) include RNA transcripts, proteins, membranes, lipids, and other analytes.

A "gene" refers to a polynucleotide that is capable of conferring biological function after being transcribed and/or translated.

As used herein a "genetically modifying agent" is a substance that alters the genetic sequence of a cell following exposure to the cell, resulting in an agent-mediated nucleic acid sequence. In embodiments, the genetically modifying agent is a small molecule, protein, pathogen (e.g., virus or bacterium), toxin, oligonucleotide, or antigen. In embodiments, the genetically modifying agent is a virus (e.g., influenza) and the agent-mediated nucleic acid sequence is the nucleic acid sequence that develops within a T-cell upon cellular exposure and contact with the virus. In embodiments, the genetically modifying agent modulates the expression of a nucleic acid sequence in a cell relative to a control (e.g., the absence of the genetically modifying agent).

The term "synthetic target" as used herein refers to a modified protein or nucleic acid such as those constructed by synthetic methods. In embodiments, a synthetic target is artificial or engineered, or derived from or contains an artificial or engineered protein or nucleic acid (e.g., non-natural or not wild type). For example, a polynucleotide that is inserted or removed such that it is not associated with nucleotide sequences that normally flank the polynucleotide as it is found in nature is a synthetic target polynucleotide.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate groups include —NH$_2$, —COOH, —COOCH$_3$, —N-hydroxysuccinimide, -maleimide,

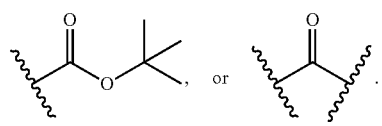

Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| carbodiimides | carboxylic acids | N-acylureas or anhydrides |
| imido esters | amines/anilines | amidines |
| silyl halides | alcohols | silyl ethers |

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., —COOH) is covalently attached to the second bioconjugate reactive group (e.g.,

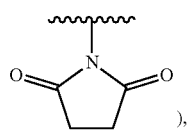

), thereby forming a bioconjugate (e.g.,

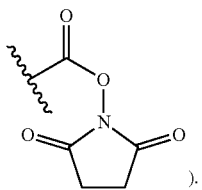

).

In embodiments, the first bioconjugate reactive group (e.g., —NH₂) is covalently attached to the second bioconjugate reactive group (e.g.,

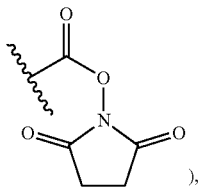

), thereby forming a bioconjugate (e.g.,

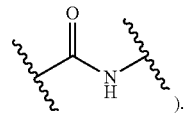

).

In embodiments, the first bioconjugate reactive group (e.g., a coupling reagent) is covalently attached to the second bioconjugate reactive group (e.g.,

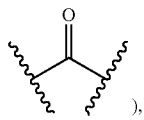 [SMILES: *C(*)=O]

), thereby forming a bioconjugate (e.g.,

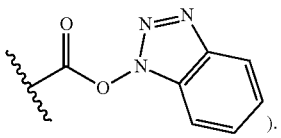 [SMILES: *C(=O)On1nnc2ccccc21]

).

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate includes a molecular entity derived from the reaction of an unsaturated bond, such as a maleimide, and a sulfhydryl group.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (e) sulfonyl halide groups for subsequent reaction with amines, for example, to form sulfonamides; (f) thiol groups, which can be converted to disulfides, reacted with acyl halides, or bonded to metals such as gold, or react with maleimides; (g) amine or sulfhydryl groups (e.g., present in cysteine), which can be, for example, acylated, alkylated or oxidized; (h) metal bonding to reactive phosphorus groups (e.g., phosphines) to form, for example, phosphate diester bonds.; (i) biotin conjugate can react with avidin or strepavidin to form a avidin-biotin complex or streptavidin-biotin complex.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system including two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Methods

In an aspect is provided a method of sequencing a template polynucleotide. In embodiments, the method includes: (A) generating a partially double-stranded amplification product including a first strand hybridized to a second strand, wherein (i) the partially double-stranded amplification product includes one or more copies (e.g., multiple copies) of the template polynucleotide, and (ii) the first strand and second strand are both covalently attached to a solid surface; (B) generating a first sequencing read by hybridizing one or more first sequencing primers to a single-stranded portion of the first strand, and extending the one or more first sequencing primers; and (C) generating a second sequencing read by hybridizing one or more second sequencing primers to the second strand, and extending the one or more second sequencing primers. In embodiments, the multiple copies of the template polynucleotide are part of the same nucleic acid strand. In embodiments, the partially double-stranded amplification product is a concatemer.

In an aspect is provided a method of sequencing a template polynucleotide of a cell in situ. In embodiments, the method includes: (A) generating a partially double-stranded amplification product in a cell, wherein the partially double-stranded amplification product includes a first strand hybridized to a second strand, wherein (i) the partially double-stranded amplification product includes one or more copies (e.g., multiple copies) of the template polynucleotide, and (ii) the first strand and second strand are both immobilized to a cellular component or a matrix (e.g., a synthetic matrix) within the cell; (B) generating a first sequencing read by hybridizing one or more first sequencing primers to a single-stranded portion of the first strand, and extending the one or more first sequencing primers; and (C) generating a second sequencing read by hybridizing one or more second sequencing primers to the second strand, and extending the one or more second sequencing primers. In embodiments, the multiple copies of the template polynucleotide are part of the same nucleic acid strand. In embodiments, the partially double-stranded amplification product is a concatemer. In embodiments, the steps (A), (B), and (C) are performed in situ. In embodiments, the steps (A), (B), and (C) are performed in a cell.

In embodiments, extending the sequencing primers includes incorporating one or more nucleotides or nucleotide analogues and detecting the incorporated nucleotides or nucleotide analogues. In embodiments, (i) generating the first sequencing read includes extending two or more first sequencing primers hybridized to the first strand, and/or (ii) generating the second sequencing read includes extending two or more second sequencing primers hybridized to the second strand. In embodiments, (i) generating the first sequencing read includes extending two or more first sequencing primers hybridized to the first strand, and (ii) generating the second sequencing read includes extending two or more second sequencing primers hybridized to the second strand. In embodiments, (i) generating the first sequencing read includes extending two or more first sequencing primers hybridized to the first strand. In embodiments, (i) generating the first sequencing read includes extending at least two first sequencing primers hybridized to the first strand. In embodiments, (ii) generating the second sequencing read includes extending two or more second sequencing primers hybridized to the second strand. In embodiments, (ii) generating the second sequencing read includes extending at least two second sequencing primers hybridized to the second strand.

In embodiments, neither the first strand, or a portion thereof, nor the second strand, or a portion thereof, is cleaved, removed, or digested during the method described herein. In embodiments, neither the first strand nor the second strand is cleaved, removed, or digested (i.e., moved from the surface) before generating the first sequencing read. In embodiments, the second strand is not cleaved before generating the first sequencing read. In embodiments, the second strand is not removed before generating the first sequencing read. In embodiments, the second strand is not digested before generating the first sequencing read. In embodiments, the first strand is not cleaved before generating the second sequencing read. In embodiments, the first strand is not removed before generating the second sequencing read. In embodiments, removal includes removing a portion of the strands (e.g., a portion of the first strand or a portion of the second strand). In embodiments, the removal is carried out by nicking the strand followed by digesting the strand.

In embodiments, the first strand is cleaved after generating the first sequencing read. In embodiments, the first strand is cleaved after generating the first sequencing read but before generating the second sequencing read. Cleaving one strand of the partially double-stranded amplification product may be referred to as linearization. Suitable methods for linearization are known, and described in more detail in application number US 2009/0118128, which is incorporated herein by reference in its entirety. For example, the first strand may be cleaved by exposing the first strand to a mixture containing a glycosylase and one or more suitable endonucleases. In embodiments, the first strand is attached to the surface in a way that allows for selective removal. If the first template strand is removed from the surface, and the partially double-stranded amplification product is denatured, for example by treatment with hydroxide or formamide, then the second strand remains immobilized as a linearized single strand. If one of the surface immobilized primers includes a cleavage site such that it can be cleaved from the surface, (e.g., diol linkage) the resulting partially double-stranded amplification product can be made single stranded using heat or chemical denaturing conditions to give a single strand containing a primer hybridization site. A cleavage site is a site which allows controlled cleavage of the first template strand by chemical, enzymatic or photochemical means.

Any suitable enzymatic, chemical, or photochemical cleavage reaction may be used to cleave the cleavage site. The cleavage reaction may result in removal of a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulfide linkage with a reducing agent (e.g., THPP or TCEP), in which case the cleavage site should include an appropriate disulfide linkage; chemical cleavage of a diol linkage with periodate, in which case the cleavage site should include a diol linkage;

generation of an abasic site and subsequent hydrolysis, etc. In embodiments, the cleavage site is included in the surface immobilized primer (e.g., within the polynucleotide sequence of the primer). In embodiments, one strand of the double-stranded amplification product (or the surface immobilized primer) may include a diol linkage which permits cleavage by treatment with periodate (e.g., sodium periodate). It will be appreciated that more than one diol can be included at the cleavage site. One or more diol units may be incorporated into a polynucleotide using standard methods for automated chemical DNA synthesis. Polynucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate ($NaIO_4$). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine. In embodiments, cleavage may be accomplished by using a modified nucleotide as the cleavable site (e.g., uracil, 8oxoG, 5-mC, 5-hmC) that is removed or nicked via a corresponding DNA glycosylase, endonuclease, or combination thereof.

In embodiments, the cleavage site is not in the substrate-bound primer (e.g., within the polynucleotide sequence of the primer). In embodiments, the cleavage site is included in the linking moiety responsible for tethering the primer to the substrate. In embodiments, the cleavage site is a cleavable linker (e.g., a disulfide containing linker that cleaves when exposed to a reducing agent).

In embodiments, the template polynucleotide is single-stranded DNA, double-stranded DNA, single-stranded RNA, or double-stranded RNA. In embodiments, the template is single-stranded DNA or single-stranded RNA and is about 10, 20, 50, 100, 150, 200, 300, 500, or 1000 nucleotides in length. In embodiments, the template polynucleotide is double-stranded DNA or double-stranded RNA and is about 10, 20, 50, 100, 150, 200, 300, 500, or 1000 base pairs in length. In embodiments, the template polynucleotide includes single-stranded circular DNA. In embodiments, the template polynucleotide is single-stranded circular DNA. In embodiments, the template polynucleotide includes double-stranded DNA. In embodiments, the template polynucleotide is double-stranded DNA. In embodiments, the template polynucleotide includes single-stranded RNA. In embodiments, the template polynucleotide is single-stranded RNA. In embodiments, the template polynucleotide includes double-stranded RNA. In embodiments, the template polynucleotide is double-stranded RNA.

In embodiments, the template polynucleotide includes primer binding sequences that are complementary to one or more substrate-bound primers. In embodiments, the substrate-bound primers are immobilized to a substrate by a covalent linker. In embodiments, the substrate-bound primers are immobilized to a solid support at the 5' end, preferably via a covalent attachment. In embodiments, the template polynucleotide includes primer binding sequences that are complementary to one or more immobilized primers. In embodiments, the immobilized primers are immobilized to a matrix (e.g., a matrix in a cell) by a covalent linker. In embodiments, the immobilized primers are attached to a matrix at the 5' end, preferably via a covalent attachment. In embodiments, at least some of the substrate-bound primers are phosphorothioated primers. In embodiments, a fraction of the total of the substrate-bound primers are phosphorothioated primers. In embodiments, at least some of the immobilized primers are phosphorothioated primers. In embodiments, a fraction of the total of the immobilized primers are phosphorothioated primers.

In embodiments, the 5' end of the primer contains a functional group that is tethered to the solid support. Non-limiting examples of covalent attachment include amine-modified polynucleotides reacting with epoxy or isothiocyanate groups on the solid support, succinylated polynucleotides reacting with aminophenyl or aminopropyl functional groups on the solid support, dibenzocycloctyne-modified polynucleotides reacting with azide functional groups on the solid support (or vice versa), trans-cyclooctyne-modified polynucleotides reacting with tetrazine or methyl tetrazine groups on the solid support (or vice versa), disulfide modified polynucleotides reacting with mercapto (i.e., sulfhydryl)-functional groups on the solid support, amine-functionalized polynucleotides reacting with carboxylic acid groups on the solid support via 1-ethyl-3-(3-dimethylaminopropyl)-carbodiimide hydrochloride (EDC) chemistry, thiol-modified polynucleotides attaching to a solid support via a disulfide bond or maleimide linkage, alkyne-modified polynucleotides attaching to a solid support via copper-catalyzed click reactions to azide functional groups on the solid support, and acrydite-modified polynucleotides polymerizing with free acrylic acid monomers on the solid support to form polyacrylamide or reacting with thiol groups on the solid support. In embodiments, the primer is attached to the solid support polymer through electrostatic binding. For example, the negatively charged phosphate backbone of the primer may be bound electrostatically to positively charged monomers on the solid support.

In embodiments, the primer includes a first bioconjugate reactive group. In embodiments, the primer is attached to a cellular component. In embodiments, the cellular component includes a second bioconjugate reactive group. In embodiments, the first bioconjugate reactive group is attached to the second bioconjugate reactive group by covalent or non-covalent bonding. In embodiments, the primer is covalently attached to a cellular component. In embodiments, the 5' end of the primer contains a functional group that is tethered to the cellular component. In embodiments, the primer is covalently attached to a matrix within the cell. In embodiments, the 5' end of the primer contains a functional group that is tethered to the matrix within the cell. Non-limiting examples of covalent attachment include amine-modified polynucleotides reacting with epoxy or isothiocyanate groups in the cell or matrix within the cell, succinylated polynucleotides reacting with aminophenyl or aminopropyl functional groups in the cell or matrix within the cell, dibenzocycloctyne-modified polynucleotides reacting with azide functional groups in the cell or matrix within the cell (or vice versa), trans-cyclooctyne-modified polynucleotides reacting with tetrazine or methyl tetrazine groups in the cell or matrix within the cell (or vice versa), disulfide modified polynucleotides reacting with mercapto-functional groups in the cell or matrix within the cell, amine-functionalized polynucleotides reacting with carboxylic acid groups in the cell or matrix within the cell via 1-ethyl-3-(3-dimethylaminopropyl)-carbodiimide hydrochloride (EDC) chemistry, thiol-modified polynucleotides attaching to cell or matrix within the cell via a disulfide bond or maleimide linkage, alkyne-modified polynucleotides attaching to the cell or matrix within the cell via copper-catalyzed click reactions to azide functional groups in the cell or matrix within the cell, and acrydite-modified polynucleotides polymerizing with free acrylic acid monomers in the cell or matrix within the cell to form polyacrylamide or reacting with thiol groups in the cell or matrix within the cell. In embodiments, the primer is attached to the polymer through electrostatic binding. For example, the negatively charged phosphate backbone of the primer may be bound electrostatically to positively charged components in the cell.

In embodiments, the method does not include an amplification step between generating the first sequencing read and generating the second sequencing read. In embodiments, the method does not include an amplification step following the first sequencing read. An amplification step, for example, can include synthesis by a polymerase of a new polynucleotide strand complementary to a template strand by adding an unmodified nucleotide (i.e., a native nucleotide). In embodiments, the amplification step includes an extension reaction. In embodiments, the amplification step includes extending the 5'-end of a substrate-bound primer. In embodiments, the amplification step includes extending the 5'-end of an immobilized primer in a cell. In embodiments, the amplification step includes copying the first strand of the template polynucleotide. In embodiments, the amplification step includes extending the 5'-end of substrate-bound primers to copy the first template polynucleotides to generate a plurality of second template polynucleotides. In embodiments, the amplification step includes extending the 5'-end of immobilized primers in a cell to copy the first template polynucleotides to generate a plurality of second template polynucleotides. In embodiments, the amplification step includes copying at least a portion of the first strand of the template polynucleotide by further extending the sequencing primer.

In embodiments, the method does not include an extension reaction between the first and second sequencing reads. In embodiments, the method does not include extending a substrate-bound primer (e.g., the 5'-end of a primer) between the first and second sequencing reads. In embodiments, the method does not include extending an immobilized primer (e.g., the 5'-end of a primer) between the first and second sequencing reads. In embodiments, the method does not include copying the first strand of the template polynucleotide between the first and second sequencing reads. In embodiments, the method does not include an extension reaction following the first sequencing read. In embodiments, the method does not include extending a substrate-bound primer (e.g., the 5'-end of a primer) following the first sequencing read. In embodiments, the method does not include extending an immobilized primer (e.g., the 5'-end of a primer) following the first sequencing read. In embodiments, the method does not include copying the first strand of the template polynucleotide following first sequencing read.

In embodiments, the partially double-stranded amplification product includes two or more copies of the template polynucleotide in series. In embodiments, the partially double-stranded amplification product is a concatemer. In this context, a concatemer is polynucleotide composed of at least two copies of the target nucleic acid wherein the copies are linked end to end (e.g., 5'-ATTC-ATTC-ATTC-3' (SEQ ID NO:1)). In embodiments, one strand of the partially double-stranded amplification product is a forward concatemer, and the second strand of the partially double-stranded amplification product is the reverse concatemer (i.e., a partial or complete complement to the forward concatemer (e.g., 5'-GAAT-GAAT-GAAT-3' (SEQ ID NO:2)). The phrases "forward" and "reverse" as used herein, when referring to the double-stranded nucleic acid or primers, do not imply a direction of transcription or that either of the strands comprises a coding region, but simply indicate that the two strands are different and are complementary to each other.

In embodiments, the partially double-stranded amplification product includes three or more copies of the template polynucleotide. In embodiments, the partially double-stranded amplification product includes at least three copies of the template polynucleotide.

In embodiments, generating the partially double-stranded amplification product includes exponential rolling circle amplification (eRCA), hyperbranched rolling circle amplification (HRCA), loop-mediated isothermal amplification (LAMP), or multiple displacement amplification (MDA). In embodiments, generating the partially double-stranded amplification product includes exponential rolling circle amplification (eRCA). In embodiments, generating the partially double-stranded amplification product includes hyperbranched rolling circle amplification (HRCA). In embodiments, generating the partially double-stranded amplification product includes loop-mediated isothermal amplification (LAMP). In embodiments, generating the partially double-stranded amplification product includes multiple displacement amplification (MDA).

In embodiments, the partially double-stranded amplification product is an unstructured assembly of polynucleotides that is bound to the solid support with one or more linkers (e.g., covalent linkers). In embodiments, the partially double-stranded amplification product includes regions of single strands and regions of double strands. In embodiments, the partially double-stranded amplification product self assembles into balls with diameters from 50 to 350 nm in size, as determined by known techniques in the art (e.g., atomic force microscopy).

In embodiments, generating the partially double-stranded amplification product includes: (a) amplifying the template polynucleotide to produce a first amplicon including multiple complements of the template polynucleotide; and (b) extending a reverse primer hybridized to the first amplicon to produce a double-stranded amplicon including multiple copies of the template polynucleotide. In embodiments, step (a) is performed in solution and then the first amplicon is hybridized to a solid support, wherein the solid support contains a plurality of substrate-bound primers. In embodiments, both step (a) and step (b) are performed on a solid support, wherein the solid support contains a plurality of substrate-bound primers. In embodiments, step (a) is performed in solution and then the first amplicon is hybridized to a matrix (e.g., a matrix in a cell), wherein the matrix contains a plurality of immobilized primers. In embodiments, both step (a) and step (b) are performed on a matrix in a cell, wherein the matrix contains a plurality of immobilized primers.

In embodiments, generating the partially double-stranded amplification product includes: (a) amplifying the template polynucleotide by extending an amplification primer with a strand-displacing polymerase, wherein the template polynucleotide includes a continuous strand lacking free 5' and 3' ends, and wherein the primer extension generates a first extension product including multiple complements of the template polynucleotide; and (b) amplifying the first extension product or a complement thereof with a plurality of primers attached to the solid surface, wherein the plurality of primers include a plurality of forward primers with complementarity to the first extension product and a plurality of reverse primers with complementarity to a complement of the first extension product, and the amplifying includes a plurality of cycles of strand denaturation, primer hybridization, and primer extension. In embodiments, generating the partially double-stranded amplification product in situ includes: (a) amplifying the template polynucleotide by extending an immobilized amplification primer with a strand-displacing polymerase, wherein the template polynucleotide includes a continuous strand lacking free 5' and 3' ends, and wherein the primer extension generates a first extension product including multiple complements of the template polynucleotide; and (b) amplifying the first extension product or a complement thereof with a plurality of immobilized primers in the cell, wherein the plurality of immobilized primers include a plurality of forward primers with complementarity to the first extension product and a plurality of reverse primers with complementarity to a complement of the first extension product, and the amplifying includes a plurality of cycles of strand denaturation, primer hybridization, and primer extension. In embodiments, the first extension product includes at least one cleavable site (e.g., a cleavable site as described herein). In embodiments, the at least one cleavable site includes deoxyuracil triphosphate (dUTP). The enzyme uracil DNA glycosylase (UDG) may then be used to remove dUTP, generating an abasic site on one strand. The polynucleotide strand including the abasic site may then be cleaved at the abasic site by treatment with endonuclease (e.g EndoIV endonuclease, AP lyase, FPG glycosylase/AP lyase, EndoVIII glycosylase/AP lyase), heat or alkali. In embodiments, the USER' reagent available from New England Biolabs (NEB catalog #M5508) is used for the creation of a single nucleotide gap at a uracil base in a duplex strand. In embodiments, the first extension product is cleaved at the at least one cleavable site prior to step (b).

In embodiments, step (a) includes an amplification technique capable of amplifying a circular template polynucleotide. In embodiments, step (a) includes exponential rolling circle amplification (eRCA). Exponential RCA is similar to the linear process except that it uses a second primer having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5(1994)). In embodiments, step (a) includes hyberbranched rolling circle amplification (HRCA). Hyperbranched RCA uses a second primer complementary to the first amplification product. This allows products to be replicated by a strand-displacement mechanism, which can yield a drastic amplification within an isothermal reaction (Lage et al., Genome Research 13:294-307 (2003), which is incorporated herein by reference in its entirety).

In embodiments, the template polynucleotide to be sequenced may be any polynucleotide that it is desired to sequence. The template polynucleotide may be of known, unknown or partially known sequence, such as, for example in re-sequencing applications. Using the template preparation method described herein, it is possible to prepare arrays of templates (i.e., clusters) starting from essentially any template polynucleotide of known, unknown or partially known sequence. In embodiments, this method is useful in the sequencing of fragments of genomic DNA. The method provides advantages in the identification of genome rearrangements, since the two regions of sequence obtained for each target molecule using the method will be known to be linked within a certain distance of each other in the genome, depending on the size of the starting target molecule.

In embodiments a source nucleic acid (e.g., genomic template DNA) is treated to form single stranded linear fragments (e.g., about 50 to 600 nucleotides). Treatment typically entails fragmentation, such as by chemical fragmentation, enzymatic fragmentation, or mechanical fragmentation, followed by denaturation to produce single stranded DNA fragments. In embodiments, the template polynucleotide includes an adapter. The adaptor may have other functional elements including tagging sequences (i.e., a barcode), attachment sequences, palindromic sequences, restriction sites, sequencing primer binding sites, functionalization sequences, and the like. Barcodes can be of any of a variety of lengths. In embodiments, the primer includes a barcode that is 10-50, 20-30, or 4-12 nucleotides in length. In embodiments, the adapter includes a primer binding sequence that is complementary to at least a portion of a primer (e.g., a sequencing primer). Primer binding sites can be of any suitable length. In embodiments, a primer binding site is about or at least about 10, 15, 20, 25, 30, or more nucleotides in length. In embodiments, a primer binding site is 10-50, 15-30, or 20-25 nucleotides in length.

In embodiments, the template polynucleotide includes single-stranded circular DNA. In embodiments, the template polynucleotide is single-stranded circular DNA. In embodiments, the template polynucleotide includes double-stranded DNA. In embodiments, the template polynucleotide is double-stranded DNA. In embodiments, the template polynucleotide includes single stranded RNA. In embodiments, the template polynucleotide is single stranded RNA. In embodiments, the template polynucleotide includes double stranded RNA. In embodiments, the template polynucleotide is double stranded RNA. In embodiments, the method further includes forming the template polynucleotide by ligating ends of a linear polynucleotide (e.g., a single stranded polynucleotide) together to form a circular template polynucleotide. In embodiments, the method further includes forming the template polynucleotide by ligating a hairpin adapter to an end of a linear polynucleotide. In embodiments, the method includes forming the template polynucleotide includes ligating hairpin adapters to both ends of the linear polynucleotide thereby forming a circular template polynucleotide. In embodiments, the template polynucleotide is single-stranded circular DNA. Methods for forming circular DNA templates are known in the art, for example linear polynucleotides are circularized in a non-template driven reaction with circularizing ligase, such as CircLigase, Taq DNA Ligase, HiFi Taq DNA Ligase, T4 ligase, or Ampligase® DNA Ligase. In embodiments, the method of forming the template polynucleotide includes ligating ends of a linear polynucleotide together. In embodiments, the two ends of the template polynucleotide are ligated directly together. In embodiments, the two ends of the template polynucleotide are ligated together with the aid of a bridging oligonucleotide (sometimes referred to as a splint oligonucleotide) that is complementary with the two ends of the template polynucleotide. In embodiments, the bridging oligonucleotide contains the amplification primer.

Circular polynucleotides of virtually any sequence can be produced using a variety of techniques (see for example U.S. Pat. No. 5,426,180; Dolinnaya et al. Nucleic Acids Research, 21: 5403-5407 (1993); or Rubin et al. Nucleic Acids Research, 23: 3547-3553 (1995), which are incorporated herein by reference). In embodiments, the template polynucleotide of step (a) is a circular polynucleotide that is about 100 to about 1000 nucleotides in length, about 100 to about 300 nucleotides in length, about 300 to about 500 nucleotides in length, or about 500 to about 1000 nucleotides in length. In embodiments, the circular polynucleotide is about 300 to about 600 nucleotides in length. In embodiments, the circular polynucleotide is about 100-1000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides in length. In embodiments, the circular polynucleotide molecule is about 100-1000 nucleotides in length. In embodiments, the circular polynucleotide molecule is about 100-300 nucleotides in length. In embodiments, the circular polynucleotide molecule is about 300-500 nucleotides in length. In embodiments, the circular polynucleotide molecule is about 500-1000 nucleotides in length. In embodiments, the circular polynucleotide molecule is about 100 nucleotides. In embodiments, the initial template polynucleotide molecule is about 300 nucleotides. In embodiments, the circular polynucleotide molecule is about 500 nucleotides. In embodiments, the circular polynucleotide molecule is about 1000 nucleotides. Circular polynucleotides may be conveniently isolated by a conventional purification column, digestion of non-circular DNA by one or more appropriate exonucleases, or both.

In embodiments, the template polynucleotide of step (a) is a circular polynucleotide that is about 100 to about 1000 nucleotides in length, about 100 to about 300 nucleotides in length, about 300 to about 500 nucleotides in length, or about 500 to about 1000 nucleotides in length. In embodiments, the circular polynucleotide is about 300 to about 600 nucleotides in length. In embodiments, the circular polynucleotide includes at least one cleavable site.

In embodiments, the method includes forming the template polynucleotide. The template polynucleotide can be a circular, dumbbell-shaped, or other closed nucleic acid molecule configuration that does not have a free 3' or 5' end. Typical library preparation steps may be performed on a linear template such that it is circularized (e.g., such as the protocols described in Kershaw, C. J., & O'Keefe, R. T. (2012) 941, 257-269). The initial template polynucleotide molecules can vary length, such as about 100-300 nucleotides long, about 300-500 nucleotides long, or about 500-1000 nucleotides long. In embodiments, the initial template polynucleotide molecular is about 100-1000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides. In embodiments, the initial template polynucleotide molecule is about 150 nucleotides. In embodiments, the initial template polynucleotide is about 100-1000 nucleotides long. In embodiments, the initial template polynucleotide is about 100-300 nucleotides long. In embodiments, the initial template polynucleotide is about 300-500 nucleotides long. In embodiments, the initial template polynucleotide is about 500-1000 nucleotides long. In embodiments, the initial template polynucleotide molecule is about 100 nucleotides. In embodiments, the initial template polynucleotide molecule is about 300 nucleotides. In embodiments, the initial template polynucleotide molecule is about 500 nucleotides. In embodiments, the initial template polynucleotide molecule is about 1000 nucleotides.

In embodiments, the amplification primer is attached to the solid surface. In embodiments, the amplification primer is in solution. In embodiments, the amplification primer includes one or more phosphorothioate nucleotides. In embodiments, the amplification primer includes a plurality of phosphorothioate nucleotides. In embodiments, about or at least about 20%, 30%, 40%, 50%, 60%, 70%, 80%, 90%, or about 100% of the nucleotides in the amplification primer are phosphorothioate nucleotides. In embodiments, most of the nucleotides in the amplification primer are phosphorothioate nucleotides. In embodiments, all of the nucleotides in the amplification primer are phosphorothioate nucleotides.

Amplification primer molecules can be fixed to surface by a variety of techniques, including covalent attachment and non-covalent attachment. In embodiments, the amplification primers are confined to an area of a discrete region (referred to as a cluster). The discrete regions may have defined locations in a regular array, which may correspond to a rectilinear pattern, circular pattern, hexagonal pattern, or the like. A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. Interstitial regions will typically have a surface material that differs from the surface material of the features on the surface. For example, features of an array can have primers that exceeds the amount or concentration present at the interstitial regions. In some embodiments the primers may not be present at the interstitial regions. In embodiments, the amplification primer is attached to a solid support and a template polynucleotide is hybridized to the primer. In embodiments, at least two different primers are attached to the solid support (e.g., a forward and a reverse primer), which facilitates generating multiple amplification products from the first extension product or a complement thereof.

In embodiments of the methods provided herein, the clusters have a mean or median separation from one another of about 0.5-5 μm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4., 4.5, 4.6, 4.7, 4.8, 4.9, 5.0 μm or a number or a range between any two of these values. In embodiments, the mean or median separation is about 10-100 microns. In embodiments, the mean or median separation is about or at least about 10, 20, 30, 40, 50, 60, 70, 80, 90, 100 μm or a number or a range between any two of these values. In embodiments, the mean or median separation is about 0.1-10 microns. In embodiments, the mean or median separation is about 0.25-5 microns. In embodiments, the mean or median separation is about 0.5-2 microns. In embodiments, the mean or median separation is about or at least about 0.1 μm. In embodiments, the mean or median separation is about or at least about 0.25 μm. In embodiments, the mean or median separation is about or at least about 0.5 µm. In embodiments, the mean or median separation is about or at least about 1.0 µm. In embodiments, the mean or median separation is about or at least about 2.0 µm. In embodiments, the mean or median separation is about or at least about 5.0 µm. In embodiments, the mean or median separation is about or at least about 10 µm. The mean or median separation may be measured center-to-center (i.e., the center of one cluster to the center of a second cluster). In embodiments of the methods provided herein, the amplicon clusters have a mean or median separation (measured center-to-center) from one another of about 0.5-5 µm. The mean or median separation may be measured edge-to-edge (i.e., the edge of one amplicon cluster to the edge of a second amplicon cluster). In embodiments of the methods provided herein, the amplicon clusters have a mean or median separation (measured edge-to-edge) from one another of about 0.2-5 µm.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about 200-3000 nanometers. In embodiments, the mean or median diameter is about or at most about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000 nanometers or a number or a range between any two of these values. In embodiments, the mean or median diameter is about 100-3000 nanometers. In embodiments, the mean or median diameter is about 100-2000 nanometers. In embodiments, the mean or median diameter is about 500-2500 nanometers. In embodiments, the mean or median diameter is about 200-1000 nanometers. In embodiments, the mean or median diameter is about 1000-2000 nanometers. In embodiments, the mean or median diameter is about or at most about 100 nanometers. In embodiments, the mean or median diameter is about or at most about 200 nanometers. In embodiments, the mean or median diameter is about or at most about 500 nanometers. In embodiments, the mean or median diameter is about or at most about 1000 nanometers. In embodiments, the mean or median diameter is about or at most about 2000 nanometers. In embodiments, the mean or median diameter is about or at most about 2500 nanometers. In embodiments, the mean or median diameter is about or at most about 3000 nanometers.

In embodiments, extending the amplification primer includes incubation with the strand-displacing polymerase in suitable conditions and for a suitable amount of time. In embodiments, the step of extending the amplification primer includes incubation with the strand-displacing polymerase (i) for about 10 seconds to about 30 minutes, and/or (ii) at a temperature of about 20° C. to about 50° C. In embodiments, incubation with the strand-displacing polymerase is for about 0.5 minutes to about 16 minutes. In embodiments, incubation with the strand-displacing polymerase is for about 0.5 minutes to about 10 minutes. In embodiments, incubation with the strand-displacing polymerase is for about 1 minutes to about 5 minutes. In embodiments, the method includes amplifying a template polynucleotide by extending an amplification primer with a strand-displacing polymerase for about 10 seconds to about 30 minutes. In embodiments, the method includes amplifying a template polynucleotide by extending an amplification primer with a strand-displacing polymerase for about 30 seconds to about 16 minutes. In embodiments, the method includes amplifying a template polynucleotide by extending an amplification primer with a strand-displacing polymerase for about 30 seconds to about 10 minutes. In embodiments, the method includes amplifying a template polynucleotide by extending an amplification primer with a strand-displacing polymerase for about 30 seconds to about 5 minutes. In embodiments, the method includes amplifying a template polynucleotide by extending an amplification primer with a strand-displacing polymerase for about 1 second to about 5 minutes. In embodiments, the method includes amplifying a template polynucleotide by extending an amplification primer with a strand-displacing polymerase for about 1 second to about 2 minutes.

In embodiments, incubation with the strand-displacing polymerase is at a temperature of about 35° C. to 42° C. In embodiments, incubation with the strand-displacing polymerase is at a temperature of about 37° C. to 40° C. In embodiments, incubation with the thermostable strand-displacing polymerase is at a temperature of about 40° C. to 80° C. In embodiments, the method includes amplifying a template polynucleotide by extending an amplification primer with a strand-displacing polymerase at a temperature of about 20° C. to about 50° C. In embodiments, the method includes amplifying a template polynucleotide by extending an amplification primer with a strand-displacing polymerase at a temperature of about 30° C. to about 50° C. In embodiments, the method includes amplifying a template polynucleotide by extending an amplification primer with a strand-displacing polymerase at a temperature of about 25° C. to about 45° C. In embodiments, the method includes amplifying a template polynucleotide by extending an amplification primer with a strand-displacing polymerase at a temperature of about 35° C. to about 45° C. In embodiments, the method includes amplifying a template polynucleotide by extending an amplification primer with a strand-displacing polymerase at a temperature of about 35° C. to about 42° C. In embodiments, the method includes amplifying a template polynucleotide by extending an amplification primer with a strand-displacing polymerase at a temperature of about 37° C. to about 40° C.

In embodiments, prior to step (a), the strand-displacing polymerase is contacted with the amplification primer and template polynucleotide in the absence of dNTPs; optionally, excess strand-displacing polymerase is removed; and amplification buffer with dNTPs is added to initiate amplification. In embodiments, prior to step (a), the strand-displacing polymerase is contacted with the amplification primer and template polynucleotide in the absence of dNTPs; and optionally, excess strand-displacing polymerase is removed. In embodiments, the amplification primer is hybridized to the template polynucleotide prior to contact with the strand-displacing polymerase. For example, the amplification primer and template polynucleotide form a complex, and the strand-displacing polymerase subsequently binds to this complex. In embodiments, the strand-displacing polymerase is contacted with the amplification primer and template polynucleotide in the absence of dNTPs and/or $Mg^{2+}$.

In embodiments, the strand-displacing polymerase is removed or inactivated prior to step (b). In embodiments, the strand-displacing polymerase is inactivated during step (b).

In embodiments, the strand-displacing polymerase is phi29 polymerase, phi29 mutant polymerase or a thermostable phi29 mutant polymerase. In embodiments, the strand-displacing polymerase is a thermostable strand-displacing (SD) DNA polymerase. In embodiments, the strand-displacing enzyme is an SD polymerase, Bst large fragment polymerase, or a phi29 polymerase or mutant thereof. In embodiments, the strand-displacing polymerase is phi29 polymerase, phi29 mutant polymerase or a thermostable phi29 mutant polymerase. A "phi polymerase" (or "φ29 polymerase") is a DNA polymerase from the φ29 phage or from one of the related phages that, like φ29, contain a terminal protein used in the initiation of DNA replication. For example, phi29 polymerases include the B103, GA-1, PZA, Φ15, BS32, M2Y (also known as M2), Nf, G1, Cp-1, PRD1, PZE, SFS, Cp-5, Cp-7, PR4, PR5, PR722, L17, Φ21, and AV-1 DNA polymerases, as well as chimeras thereof. A phi29 mutant DNA polymerase includes one or more mutations relative to naturally-occurring wild-type phi29 DNA polymerases, for example, one or more mutations that alter interaction with and/or incorporation of nucleotide analogs, increase stability, increase read length, enhance accuracy, increase phototolerance, and/or alter another polymerase property, and can include additional alterations or modifications over the wild-type phi29 DNA polymerase, such as one or more deletions, insertions, and/or fusions of additional peptide or protein sequences. Thermostable phi29 mutant polymerases are known in the art, see for example US 2014/0322759, which is incorporated herein by reference for all purposes. For example, a thermostable phi29 mutant polymerase refers to an isolated bacteriophage phi29 DNA polymerase comprising at least one mutation selected from the group consisting of MBR, V51A, M97T, L123S, G197D, K209E, E221K, E239G, Q497P, K512E, E515A, and F526 (relative to wild type phi29 polymerase).

In embodiments, step (b) includes (i) extension of a 3' end of a first substrate-bound primer extension product hybridized to a second substrate-bound primer or a second substrate-bound primer extension product. In embodiments, step (b) includes (i) extension of a 3' end of a first substrate-bound primer extension product hybridized to a second substrate-bound primer or a second substrate-bound primer extension product and (ii) extension of a 3' end of a third substrate-bound primer extension product hybridized to itself. In embodiments, step (b) includes (i) extension of a 3' end of a first substrate-bound primer extension product hybridized to a second substrate-bound primer or a second substrate-bound primer extension product or (ii) extension of a 3' end of a third substrate-bound primer extension product hybridized to itself. In embodiments, step (b) includes addition of a second polymerase. In embodiments, step (b) includes (i) extension of a 3' end of a first substrate-bound primer extension product hybridized to a second substrate-bound primer extension product, and/or (ii) extension of a 3' end of a third substrate-bound primer extension product hybridized to itself. In embodiments, step (b) includes addition of a second polymerase. In embodiments, step (b) includes (ii) extension of a 3' end of a third substrate-bound primer extension product partially hybridized to a complementary substrate bound primer extension product (e.g., a first substrate-bound primer extension product or a second substrate-bound primer extension product).

In embodiments, step (b) includes (i) extension of a 3' end of a first immobilized primer extension product hybridized to a second immobilized primer or a second immobilized primer extension product in a cell. In embodiments, step (b) includes (i) extension of a 3' end of a first immobilized primer extension product hybridized to a second immobilized primer or a second immobilized primer extension product in a cell and (ii) extension of a 3' end of a third immobilized primer extension product hybridized to itself in a cell. In embodiments, step (b) includes (i) extension of a 3' end of a first immobilized primer extension product hybridized to a second immobilized primer or a second immobilized primer extension product in a cell or (ii) extension of a 3' end of a third immobilized primer extension product hybridized to itself in a cell. In embodiments, step (b) includes addition of a second polymerase in a cell. In embodiments, step (b) includes (i) extension of a 3' end of a first immobilized primer extension product hybridized to a second immobilized primer extension product in a cell, and/or (ii) extension of a 3' end of a third immobilized primer extension product hybridized to itself in a cell. In embodiments, step (b) includes (ii) extension of a 3' end of a third immobilized primer extension product partially hybridized to a complementary immobilized primer extension product in a cell (e.g., a first immobilized primer extension product or a second immobilized primer extension product in a cell).

In embodiments, step (b) includes amplification methodologies described herein or known in the art to amplify the products of the first amplification reaction. Suitable methods for amplification include, but are not limited to, the polymerase chain reaction (PCR), strand displacement amplification (SDA), transcription mediated amplification (TMA) and nucleic acid sequence-based amplification (NASBA), for example, as described in U.S. Pat. No. 8,003,354, which is incorporated herein by reference in its entirety. The above amplification methods can be employed to amplify one or more nucleic acids of interest. For example, PCR, multiplex PCR, SDA, TMA, NASBA and the like can be utilized to amplify immobilized nucleic acid fragments generated from the first amplification method of the two-step method described herein.

In embodiments, step (b) includes addition of a second polymerase. In embodiments, the second polymerase is different than the polymerase used in step (a). In embodiments, the polymerase is an archaeal DNA polymerase. In embodiments, the second polymerase is Bst DNA Polymerase, Vent (exo-) DNA Polymerase, SD polymerase, Pfu DNA polymerase, Taq polymerase, Phusion High-Fidelity DNA Polymerase, Q5 High-Fidelity DNA Polymerase, or mutant of any one of the foregoing. In embodiments, the polymerase is Bst DNA Polymerase, Vent (exo-) DNA Polymerase, SD Polymerase, Phusion High-Fidelity DNA Polymerase, or Q5 High-Fidelity DNA Polymerase. In embodiments, the second polymerase is a thermostable strand-displacing (SD) DNA polymerase.

In embodiments, step (b) includes thermal bridge polymerase chain reaction amplification; for example, as exemplified by the disclosures of U.S. Pat. Nos. 5,641,658; 7,115,400; 7,790,418; U.S. Patent Publ. No. 2008/0009420, each of which is incorporated herein by reference in its entirety. In general, bridge amplification uses repeated steps of annealing of primers to templates, primer extension, and separation of extended primers from templates. Because the forward and reverse primers are attached to the solid support, the extension products released upon separation from an initial template are also attached to the solid support. Both strands are immobilized on the solid support at the 5' end, preferably via a covalent attachment. The 3' end of an amplification product is then permitted to anneal to a nearby reverse primer, forming a "bridge" structure. The reverse primer is then extended to produce a further template molecule that can form another bridge. During bridge PCR, additional chemical additives may be included in the reaction mixture, in which the DNA strands are denatured by flowing a denaturant over the DNA, which chemically denatures complementary strands. This is followed by washing out the denaturant and reintroducing a polymerase in buffer conditions that allow primer annealing and extension. In embodiments, forward and/or reverse primers hybridize to primer binding sites that are specific to a particular target nucleic acid sequence present in the first extension product of step (a). In embodiments, forward and/or reverse primers hybridize to primer binding sites that are common among different first extension products of step (a). In embodiments, a portion of the forward primers (i.e., a fraction of the total number of forward primers) include a 3' modification to prevent extension in step (a). In embodiments, after step (a) the 3' modification is removed and the forward primers may extended in step (b). In embodiments, the 3' modification is a C3, C9, C12, or C18 spacer phosphoramidite, a 3'phosphate, a C3, C6, C12 amino modifier, or a reversible blocking moiety (e.g., reversible blocking moieties are described in U.S. Pat. Nos. 7,541,444 and 7,057,026). In embodiments, the 3' modification is a 3'-phosphate modification includes a 3' phosphate moiety, which is removed by a PNK enzyme.

In embodiments, step (b) describes a plurality of strand denaturation cycles, wherein the initial denaturation cycle is at different conditions from the remaining denaturation cycles. For example, in embodiments, the initial denaturation cycle is at about 85° C.-95° C. for about 1 minute to about 10 minutes, whereas denaturation in the remaining cycles is different (e.g. about 85° C. for about 15-30 sec). In embodiments, step (b) includes an initial denaturation at about 85° C.-95° C. for about 5 minutes to about 10 minutes. In embodiments, step (b) includes an initial denaturation at 90° C.-95° C. for about 1 to 10 minutes. In embodiments, step (b) includes an initial denaturation at 80° C.-85° C. for about 1 to 10 minutes. In embodiments, step (b) includes an initial denaturation at 85° C.-90° C. for about 1 to 10 minutes.

In embodiments, step (b) includes an initial denaturation at about 85° C.-95° C. for about 1 minutes to about 10 minutes. In embodiments, step (b) includes an initial denaturation at about 85° C.-95° C. for about 5 minutes to about 10 minutes. In embodiments, the plurality of cycles includes thermally cycling between (i) about 85° C. for about 15-30 sec for denaturation, and (ii) about 65° C. for about 1 minute for annealing/extension of the primer. In embodiments, the plurality of cycles includes thermally cycling between (i) about 85° C. for about 15-30 sec for denaturation, and (ii) about 65° C. for about 30 seconds for annealing/extension of the primer. In embodiments, the plurality of cycles includes thermally cycling between (i) about 80° C. to 90° C. for denaturation, and (ii) about 55° C. to about 65° C. for annealing/extension of the primer. In embodiments, the plurality of cycles includes thermally cycling between (i) about 85° C. for denaturation, and (ii) about 55° C. for annealing/extension of the primer. In embodiments, the plurality of cycles includes thermally cycling between (i) about 85° C. for denaturation, and (ii) about 65° C. for annealing/extension of the primer. In embodiments, the plurality of cycles includes thermally cycling between (i) less than 80° C. (e.g., 70 to 80° C.) for denaturation, and (ii) about 55° C. to about 65° C. for annealing/extension of the primer. In embodiments, the plurality of cycles includes thermally cycling between (i) about 70° C. for denaturation, and (ii) about 65° C. for annealing/extension of the primer. In embodiments, the plurality of cycles includes thermally cycling between (i) about 75° C. for denaturation, and (ii) about 55° C. for annealing/extension of the primer. In embodiments, the plurality of cycles includes thermally cycling between (i) about 85° C. for denaturation, and (ii) about 65° C. for annealing/extension of the primer.

In embodiments, the plurality of cycles includes thermally cycling between (i) about 85° C. for less than 1 minute for denaturation, and (ii) about 65° C. for about 1 to 2 minutes for annealing/extension of the primer. In embodiments, the plurality of cycles includes thermally cycling between (i) about 85° C. for less than 1 minute for denaturation, and (ii) about 60° C. to about 65° C. for about 1 minute for annealing/extension of the primer. In embodiments, the plurality of cycles includes thermally cycling between (i) about 85° C. for about 15-30 sec for denaturation and (ii) about 65° C. for about 1 minute for annealing/extension of the primer. In embodiments, the plurality of cycles includes thermally cycling between (i) about 85° C. for about 30 sec for denaturation and (ii) about 65° C. for about 1 minute for annealing/extension of the primer. In embodiments, the plurality of cycles includes thermally cycling between (i) about 85° C. for about 15-30 sec for denaturation, and (ii) about 65° C. for about 30 seconds for annealing/extension of the primer. In embodiments, the plurality of cycles includes thermally cycling between (i) about 85° C. for about 15-30 sec for denaturation, and (ii) about 65° C. for about 1 minute for annealing/extension of the primer. In embodiments, the temperature and duration for the annealing of the primer and the extension of the primer are different. In embodiments, the plurality of cycles includes thermally cycling between (i) about 90° C. to 95° C. for about 15 to 30 sec for denaturation and (ii) about 55° C. to about 65° C. for about 30 to 60 seconds for annealing and about 65° C. to 70° C. for about 30 to 60 seconds for extension of the primer. In embodiments, the plurality of denaturation steps is at a temperature of about 80° C.-95° C. In embodiments, the plurality of denaturation steps is at a temperature of about 80° C.-90° C. In embodiments, the plurality of denaturation steps is at a temperature of about 85° C.-90° C. In embodiments, the plurality of denaturation steps is at a temperature of about 81° C., 82° C., 83° C., 84° C., 85° C., 86° C., 87° C., 88° C., 89° C., or about 90° C. In embodiments, the plurality of denaturation steps is at a temperature of about 91° C., 92° C., 93° C., 94° C., 95° C., 96° C., 97° C., 98° C., or about 99° C. In embodiments, the plurality of denaturation steps is at a temperature of about 87° C., 88° C., 89° C., 90° C., 91° C., 92° C., 93° C., 94° C., or about 95° C. In embodiments, the plurality of denaturation steps is at a temperature of about 90° C., 91° C., 92° C., 93° C., 94° C., or about 95° C. In embodiments, the plurality of denaturation steps is at a temperature of about 70° C.-85° C. In embodiments, the plurality of denaturation steps is at a temperature of about 70° C.-80° C. In embodiments, the plurality of denaturation steps is at a temperature of about 75° C.-80° C. In embodiments, the plurality of denaturation steps is at a temperature of about 70° C., 71° C., 72° C., 73° C., 74° C., 75° C., 76° C., 77° C., 78° C., 79° C., or about 80° C. In embodiments, the annealing/extension of the primer cycle is at a temperature of about 55° C., 56° C., 57° C., 58° C., 59° C., 60° C., 61° C., 62° C., 63° C., 64° C., or about 65° C.

In embodiments, step (b) includes thermal bridge polymerase chain reaction (t-bPCR) amplification. In embodiments, step (b) includes incubation in an additive. In embodiments, step (b) does not include incubation in an additive. In embodiments, step (b) includes incubation in an additive that lowers a DNA denaturation temperature. In embodiments, the additive is betaine, dimethyl sulfoxide (DMSO), ethylene glycol, formamide, glycerol, guanidine thiocyanate, 4-methylmorpholine 4-oxide (NMO), or a mixture thereof. In embodiments, the additive is betaine, dimethyl sulfoxide (DMSO), ethylene glycol, formamide, glycerol, guanidine thiocyanate, or 4-methylmorpholine 4-oxide (NMO).

In embodiments, step (b) describes amplifying the first extension product or a complement thereof on a solid support, wherein amplifying includes a plurality of cycles of strand denaturation, primer hybridization, and primer extension. Although each cycle will include each of these three events (denaturation, hybridization, and extension), events within a cycle may or may not be discrete. For example, each step may have different reagents and/or reaction conditions (e.g., temperatures). Alternatively, some steps may proceed without a change in reaction conditions. For example, extension may proceed under the same conditions (e.g., same temperature) as hybridization. After extension, the conditions are changed to start a new cycle with a new denaturation step, thereby amplifying the concatemer. Primer extension products from an earlier cycle may serve as templates for a later amplification cycle. In embodiments, the plurality of cycles is about 5 to about 50 cycles. In embodiments, the plurality of cycles is about 10 to about 45 cycles. In embodiments, the plurality of cycles is about 10 to about 20 cycles. In embodiments, the plurality of cycles is about 20 to about 30 cycles. In embodiments, the plurality of cycles is 10 to 45 cycles. In embodiments, the plurality of cycles is 10 to 20 cycles. In embodiments, the plurality of cycles is 20 to 30 cycles. In embodiments, the plurality of cycles is about 10 to about 45 cycles. In embodiments, the plurality of cycles is about 20 to about 30 cycles.

In embodiments, step (b) includes chemical bridge polymerase chain reaction (c-bPCR) amplification. In embodiments, step (b) includes denaturation using a chemical denaturant. In embodiments, step (b) includes denaturation using acetic acid, hydrochloric acid, nitric acid, formamide, guanidine, sodium salicylate, sodium hydroxide, dimethyl sulfoxide (DMSO), propylene glycol, urea, or a mixture thereof. In embodiments, step (b) includes denaturation using acetic acid, hydrochloric acid, nitric acid, formamide, guanidine, sodium salicylate, sodium hydroxide, dimethyl sulfoxide (DMSO), propylene glycol, or urea. In embodiments, the chemical denaturant is sodium hydroxide or formamide. In embodiments, step (b) includes thermal bridge polymerase chain reaction (t-bPCR) amplification. In embodiments, step (b) includes chemical bridge polymerase chain reaction (c-bPCR) amplification. Chemical bridge polymerase chain reactions include fluidically cycling a denaturant (e.g., formamide) and maintaining the temperature within a narrow temperature range (e.g., +/−5° C.). In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a significantly lower concentration than traditional chemical bridge polymerase chain reactions.

In embodiments, step (b) includes fluidic cycling between an extension mixture that includes a polymerase and dNTPs, and a chemical denaturant. In embodiments, the polymerase is a strand-displacing polymerase or a non-strand displacing polymerase. In embodiments, the solutions are thermally cycled between about 40° C. to about 65° C. during fluidic cycling of the extension mixture and the chemical denaturant. For example, the extension cycle is maintained at a temperature of 55° C.-65° C., followed by a denaturation cycle that is maintained at a temperature of 40° C.-65° C., or by a denaturation step in which the temperature starts at 60° C.-65° C. and is ramped down to 40° C. prior to exchanging the reagent. In embodiments, step (b) includes modulating the reaction temperature prior to initiating the next cycle. In embodiments, the denaturation cycle and/or the extension cycle is maintained at a temperature for a sufficient amount of time, and prior to starting the next cycle the temperature is modulated (e.g., increased relative to the starting temperature or reduced relative to the starting temperature). In embodiments, the denaturation cycle is performed at a temperature of 60° C.-65° C. for about 5-45 sec, then the temperature is reduced (e.g., lowered to about 40° C.) before starting an extension cycle (i.e., before introducing an extension mixture). Lowering the temperature, even in the presence of a chemical denaturant, facilitates primer hybridization in the subsequent step when the amplicons are exposed to conditions that promote hybridization. In embodiments, the extension cycle is performed at a temperature of 50° C.-60° C. for about 0.5-2 minutes, then the temperature is increased (e.g., raised to between about 60° C. to about 70° C., or to about 65° C. to about 72° C.) after introducing the extension mixture. In embodiments, the cycling between the extension mixture and the chemical denaturant is performed at least 5, at least 10, at least 20, at least 30, at least 40, at least 50, at least 75, at least 100, or at least 200 times. In embodiments, the cycling between the extension mixture and the chemical denaturant is performed at least 5, at least 10, at least 20, at least 30, at least 40, at least 50, or at least 75 times. In embodiments, the cycling between the extension mixture and the chemical denaturant is performed about 5, about 10, about 20, about 30, about 40, about 50, about 75, about 100, or about 200 times. In embodiments, the cycling between the extension mixture and the chemical denaturant is performed about 5, about 10, about 20, about 30, about 40, about 50, or about 75 times. In embodiments, the cycling between the extension mixture and the chemical denaturant is performed a total of 5, 10, 20, 30, 40, 50, 75, 100, 200, or more times. In embodiments, the cycling between the extension mixture and the chemical denaturant is performed a total of 5, 10, 20, 30, 40, 50, 75 or more times. In embodiments, the fluidic cycling is performed in the presence of about 2 to about 15 mM $Mg^{2+}$. In embodiments, the fluidic cycling is performed in the presence of about 2, about 3, about 4, about 5, about 6, about 7, about 8, about 9, about 10, about 11, about 12, about 13, about 14, or about 15 mM $Mg^{2+}$.

In embodiments, generating a first sequencing read includes hybridizing one or more first sequencing primers to a single-stranded portion of the first strand. Similarly, generating a second sequencing read includes hybridizing one or more second sequencing primers to a single-stranded portion of the second strand. Following hybridization, the sequencing reaction (e.g., the first or second sequencing reaction) proceeds via successive incorporation of nucleotides or oligonucleotides to the sequencing primer (i.e., the first or the second sequencing primer), resulting in determination of the sequence of a region of the target polynucleotide.

A variety of sequencing methodologies can be used such as sequencing-by synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and. 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750, 341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

A number of techniques have been described for reading out RNA transcription levels in tissue sections directly (i.e., in-situ), without requiring spatial barcoding, based on single molecule fluorescence in situ hybridization. These include MERFISH (Multiplexed Error-Robust Fluorescence In Situ Hybridization), STARmap (Spatially-resolved Transcript Amplicon Readout mapping), DART-FISH, seq-FISH (Sequential Fluorescence In Situ Hybridization), FISSEQ (fluorescent in situ sequencing), and others (see for example Chen, K. H., et al. (2015). Science, 348(6233), aaa6090; Wang, G., Moffitt, J. R. & Zhuang, X. Sci Rep. 2018; 8, 4847; Wang X. et al; Science, 2018; 27, Vol 361, Issue 6400, eaat5691; Cai, M. Dissertation, (2019) UC San Diego. ProQuest ID: Cai_ucsd_0033D_18822; Lee J H et al. Nat. Protoc. 2015; 10(3):442-58); and Sansone, A. Nat Methods 16, 458; 2019). In all of these techniques, individual RNA transcripts are individually resolved, typically with pre-amplification or requiring multiple instances of labeled probes. Some of these techniques have been combined with super-resolution microscopy, expansion microscopy, or both, to increase the resolution and allow more transcripts to be resolved and thus counted.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing includes a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 7,541,444, 7,057,026, and 10,738,072. Once such a modified nucleotide has been incorporated into the growing polynucleotide chain complementary to the region of the template being sequenced, there is no free 3'—OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Sequencing can be carried out using any suitable sequencing-by-synthesis (SBS) technique, wherein modified nucleotides are added successively to a free 3' hydroxyl group, typically initially provided by a sequencing primer, resulting in synthesis of a polynucleotide chain in the 5' to 3' direction. In embodiments, sequencing includes detecting a sequence of signals. In embodiments, sequencing includes extension of a sequencing primer with labeled nucleotides. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. Non-limiting examples of suitable labels are described in U.S. Pat. Nos. 8,178,360, 5,188,934 (4,7-dichlorofluorscein dyes); U.S. Pat. No. 5,366,860 (spectrally resolvable rhodamine dyes); U.S. Pat. No. 5,847, 162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthene dyes): U.S. Pat. No. 5,688,648 (energy transfer dyes); and the like.

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

In embodiments, generating a sequencing read includes determining the identity of the nucleotides in the template polynucleotide. In embodiments, a sequencing read, e.g., a first sequencing read or a second sequencing read, includes determining the identity of a portion (e.g., 1, 2, 5, 10, 20, 50 nucleotides) of the total template polynucleotide. In embodiments the first sequencing read determines the identity of 5-10 nucleotides and the second sequencing read determines the identity of more than 5-10 nucleotides (e.g., 11 to 200 nucleotides). In embodiments the first sequencing read determines the identity of more than 5-10 nucleotides (e.g., 11 to 200 nucleotides) and the second sequencing read determines the identity of 5-10 nucleotides.

In embodiments, the sequencing method relies on the use of modified nucleotides that can act as reversible reaction terminators. Once the modified nucleotide has been incorporated into the growing polynucleotide chain complementary to the region of the template being sequenced there is no free 3'—OH group available to direct further sequence extension and therefore the polymerase cannot add further nucleotides. Once the identity of the base incorporated into the growing chain has been determined, the 3' reversible terminator may be removed to allow addition of the next successive nucleotide. These such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides may carry a label (e.g., a fluorescent label) to facilitate their detection. Each nucleotide type may carry a different fluorescent label. However, the detectable label need not be a fluorescent label. Any label can be used which allows the detection of an incorporated nucleotide. One method for detecting fluorescently labeled nucleotides includes using laser light of a wavelength specific for the labeled nucleotides, or the use of other suitable sources of illumination. The fluorescence from the label on the nucleotide may be detected (e.g., by a CCD camera or other suitable detection means).

In embodiments, the methods of sequencing a nucleic acid include extending a complementary polynucleotide (e.g., a primer) that is hybridized to the nucleic acid by incorporating a first nucleotide. In embodiments, the method includes a buffer exchange or wash step. In embodiments, the methods of sequencing a nucleic acid include a sequencing solution. The sequencing solution includes (a) an adenine nucleotide, or analog thereof (b) (i) a thymine nucleotide, or analog thereof, or (ii) a uracil nucleotide, or analog thereof; (c) a cytosine nucleotide, or analog thereof and (d) a guanine nucleotide, or analog thereof.

The methods and kits of the present disclosure may be applied, mutatis mutandis, to the sequencing of RNA, or to determining the identity of a ribonucleotide.

In certain embodiments, a sequencing method provided herein comprises sequencing both strands of a double stranded nucleic acid with an error rate of $5 \times 10^{-5}$ or less, $1 \times 10^{-5}$ or less, $5 \times 10^{-6}$ or less, $1 \times 10^{-6}$ or less, $5 \times 10^{-7}$ or less, $1 \times 10^{-7}$ or less, $5 \times 10^{-8}$ or less, or $1 \times 10^{-8}$ or less. In certain embodiments, a sequencing method provided herein comprises sequencing both strands of a double stranded nucleic acid with an error rate of $5 \times 10^{-5}$ to $1 \times 10^{-8}$, $1 \times 10^{-5}$ to $1 \times 10^{-8}$, $5 \times 10^{-5}$ to $1 \times 10^{-7}$, $1 \times 10^{-5}$ to $1 \times 10^{-7}$, $5 \times 10^{-6}$ to $1 \times 10^{-8}$, or $1 \times 10^{-6}$ to $1 \times 10^{-8}$.

Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by N nucleotides, thereby detecting a sequence of length N. Example SBS procedures, fluidic systems and detection platforms that can be readily adapted for use with an array produced by the methods of the present disclosure are described, for example, in Bentley et al., Nature 456: 53-59 (2008), US 2018/0274024, WO 2017/205336, US 2018/0258472, each of which are incorporated herein in their entirety for all purposes.

In embodiments, the methods of the invention herein are performed in situ on isolated cells or in tissue sections that have been prepared according to methodologies known in the art. Methods for permeabilization and fixation of cells and tissue samples are known in the art, as exemplified by Cremer et al., The Nucleus: Volume 1: Nuclei and Subnuclear Components, R. Hancock (ed.) 2008; and Larsson et al., Nat. Methods (2010) 7:395-397, the content of each of which is incorporated herein by reference in its entirety. In embodiments, the cell is cleared (e.g., digested) of proteins, lipids, or proteins and lipids.

In embodiments, the cell in situ is obtained from a subject (e.g., human or animal tissue). Once obtained, the cell is placed in an artificial environment in plastic or glass containers supported with specialized medium containing essential nutrients and growth factors to support proliferation. In embodiments, the cell is permeabilized and immobilized to a solid support surface. In embodiments, the cell is permeabilized and immobilized to an array (i.e., to discrete locations arranged in an array). In embodiments, the cell is immobilized to a solid support surface. In embodiments, the surface includes a patterned surface (e.g., suitable for immobilization of a plurality of cells in an ordered pattern. The discrete regions of the ordered pattern may have defined locations in a regular array, which may correspond to a rectilinear pattern, circular pattern, hexagonal pattern, or the like. These discrete regions are separated by interstitial regions. As used herein, the term "interstitial region" refers to an area in a substrate or on a surface that separates other areas of the substrate or surface. In embodiments, a plurality of cells are immobilized on a patterned surface that have a mean or median separation from one another of about 10-20 μm. In embodiments, a plurality of cells are immobilized on a patterned surface that have a mean or median separation from one another of about 1-10 μm. In embodiments, a plurality of cells are immobilized on a patterned surface that have a mean or median separation from one another of about 10-20; 10-50; or 100 μm. In embodiments, a plurality of cells are arrayed on a substrate. In embodiments, a plurality of cells are immobilized in a 96-well microplate having a mean or median well-to-well spacing of about 8 mm to about 12 mm (e.g., about 9 mm). In embodiments, a plurality of cells are immobilized in a 384-well microplate having a mean or median well-to-well spacing of about 3 mm to about 6 mm (e.g., about 4.5 mm).

In embodiments, the cell forms part of a tissue in situ. In embodiments, the cell is an isolated single cell. In embodiments, the cell is a prokaryotic cell. In embodiments, the cell is a eukaryotic cell. In embodiments, the cell is a bacterial cell, a fungal cell, a plant cell, or a mammalian cell. In embodiments, the cell is a stem cell. In embodiments, the stem cell is an embryonic stem cell, a tissue-specific stem cell, a mesenchymal stem cell, or an induced pluripotent stem cell. In embodiments, the cell is an endothelial cell, muscle cell, myocardial, smooth muscle cell, skeletal muscle cell, mesenchymal cell, epithelial cell; hematopoietic cell, such as lymphocytes, including T cell, e.g., (Th1 T cell, Th2 T cell, Th0 T cell, cytotoxic T cell); B cell, pre-B cell; monocytes; dendritic cell; neutrophils; or a macrophage. In embodiments, the cell is a stem cell, an immune cell, a cancer cell, a viral-host cell, or a cell that selectively binds to a desired target. In embodiments, the cell includes a T cell receptor gene sequence, a B cell receptor gene sequence, or an immunoglobulin gene sequence. In embodiments, the cell includes a Toll-like receptor (TLR) gene sequence. In embodiments, the cell includes a gene sequence corresponding to an immunoglobulin light chain polypeptide and a gene sequence corresponding to an immunoglobulin heavy chain polypeptide. In embodiments, the cell is a genetically modified cell.

In embodiments, the cell is a prokaryotic cell. In embodiments, the cell is a bacterial cell. In embodiments, the bacterial cell is a *Bacteroides, Clostridium, Faecalibacterium, Eubacterium, Ruminococcus, Peptococcus, Peptostreptococcus*, or *Bifidobacterium* cell. In embodiments, the bacterial cell is a *Bacteroides fragilis, Bacteroides melaninogenicus, Bacteroides oxalis, Enterococcus faecalis, Escherichia coli, Enterobacter* sp., *Klebsiella* sp., *Bifidobacterium bifidum, Staphylococcus aureus, Lactobacillus, Clostridium perfringens, Proteus mirabilis, Clostridium tetani, Clostridium septicum, Pseudomonas aeruginosa, Salmonella enterica, Faecalibacterium prausnitzii, Peptostreptococcus* sp., or *Peptococcus* sp. cell. In embodiments, the cell is a fungal cell. In embodiments, the fungal cell is a *Candida, Saccharomyces, Aspergillus, Penicillium, Rhodotorula, Trametes, Pleospora, Sclerotinia, Bullera*, or a *Galactomyces* cell.

In embodiments, the cell is a viral-host cell. A "viral-host cell" is used in accordance with its ordinary meaning in virology and refers to a cell that is infected with a viral genome (e.g., viral DNA or viral RNA). The cell, prior to infection with a viral genome, can be any cell that is susceptible to viral entry. In embodiments, the viral-host cell is a lytic viral-host cell. In embodiments, the viral-host cell is capable of producing viral protein. In embodiments, the viral-host cell is a lysogenic viral-host cell. In embodiments, the cell is a viral-host cell including a viral nucleic acid sequence, wherein the viral nucleic acid sequence is from a Hepadnaviridae, Adenoviridae, Herpesviridae, Poxviridae, Parvoviridae, Reoviridae, Coronaviridae, Retroviridae virus.

In embodiments, the cell is an adherent cell (e.g., epithelial cell, endothelial cell, or neural cell). Adherent cells are usually derived from tissues of organs and attach to a substrate (e.g., epithelial cells adhere to an extracellular matrix coated substrate via transmembrane adhesion protein complexes). Adherent cells typically require a substrate, e.g., tissue culture plastic, which may be coated with extracellular matrix (e.g., collagen and laminin) components to increase adhesion properties and provide other signals needed for growth and differentiation. In embodiments, the cell is a neuronal cell, an endothelial cell, epithelial cell, germ cell, plasma cell, a muscle cell, peripheral blood mononuclear cell (PBMC), a myocardial cell, or a retina cell.

In embodiments, the cell is bound to a known antigen. In embodiments, the cell is a cell that selectively binds to a desired target, wherein the target is an antibody, or antigen binding fragment, an aptamer, affimer, non-immunoglobulin scaffold, small molecule, or genetic modifying agent. In embodiments, the cell is a leukocyte (i.e., a white-blood cell). In embodiments, leukocyte is a granulocyte (neutrophil, eosinophil, or basophil), monocyte, or lymphocyte (T cells and B cells). In embodiments, the cell is a lymphocyte. In embodiments, the cell is a T cell, an NK cell, or a B cell.

In embodiments, the cell is an immune cell. In embodiments, the immune cell is a granulocyte, a mast cell, a monocyte, a neutrophil, a dendritic cell, or a natural killer (NK) cell. In embodiments, the immune cell is an adaptive cell, such as a T cell, NK cell, or a B cell. In embodiments, the cell includes a T cell receptor gene sequence, a B cell receptor gene sequence, or an immunoglobulin gene sequence. In embodiments, the plurality of target nucleic acids includes non-contiguous regions of a nucleic acid molecule. In embodiments, the non-contiguous regions include regions of a VDJ recombination of a B cell or T cell.

In embodiments, the cell is a cancer cell. In embodiments, the cancer is lung cancer, colorectal cancer, skin cancer, colon cancer, pancreatic cancer, breast cancer, cervical cancer, lymphoma, leukemia, or a cancer associated with aberrant K-Ras, aberrant APC, aberrant Smad4, aberrant p53, or aberrant TGFβ. In embodiments, the cancer cell includes a ERBB2, KRAS, TP53, PIK3CA, or FGFR2 gene. In embodiments, the cancer cell includes a cancer-associated gene (e.g., an oncogene associated with kinases and genes involved in DNA repair) or a cancer-associated biomarker. A "biomarker" is a substance that is associated with a particular characteristic, such as a disease or condition. A change in the levels of a biomarker may correlate with the risk or progression of a disease or with the susceptibility of the disease to a given treatment. In embodiments, the cancer is Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, or Uveal Melanoma. In embodiments, the cancer-associated gene is a nucleic acid sequence identified within The Cancer Genome Atlas Program, accessible at www.cancer.gov/tcga.

In embodiments, the cancer-associated biomarker is MDC, NME-2, KGF, P1GF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, or EPO. In embodiments, the cancer-associated gene is a AKT1, AKT2, AKT3, ALK, AR, ARAF, ARID1A, ATM, ATR, ATRX, AXL, BAP1, BRAF, BRCA1, BRCA2, BTK, CBL, CCND1, CCND2, CCND3, CCNE1, CDK12, CDK2, CDK4, CDK6, CDKN1B, CDKN2A, CDKN2B, CHEK1, CHEK2, CREBBP, CSF1R, CTNNB1, DDR2, EGFR, ERBB2, ERBB3, ERBB4, ERCC2, ERG, ESR1, ETV1, ETV4, ETV5, EZH2, FANCA, FANCD2, FANCI, FBXW7, FGF19, FGF3, FGFR1, FGFR2, FGFR3, FGFR4, FGR, FLT3, FOXL2, GATA2, GNA11, GNAQ, GNAS, H3F3A, HIST1H3B, HNF1A, HRAS, IDH1, IDH2, IGF1R, JAK1, JAK2, JAK3, KDR, KIT, KNSTRN, KRA5, MAGOH, MAP2K1, MAP2K2, MAP2K4, MAPK1, MAX, MDM2, MDM4, MED12, MET, MLH1, MRE11A, MSH2, MSH6, MTOR, MYB, MYBL1, MYC, MYCL, MYCN, MYD88, NBN, NF1, NF2, NFE2L2, NOTCH1, NOTCH2, NOTCH3, NOTCH4, NRAS, NRG1, NTRK1, NTRK2, NTRK3, NUTM1, PALB2, PDGFRA, PDGFRB, PIK3CA, PIK3CB, PIK3R1, PMS2, POLE, PPARG, PPP2R1A, PRKACA, PRKACB, PTCH1, PTEN, PTPN11, RAC1, RAD50, RAD51, RAD51B, RAD51C, RAD51D, RAF1, RB1, RELA, RET, RHEB, RHOA, RICTOR, RNF43, ROS1, RSPO2, RSPO3, SETD2, SF3B1, SLX4, SMAD4, SMARCA4, SMARCB1, SMO, SPOP, SRC, STAT3, STK11, TERT, TOP1, TP53, TSC1, TSC2, U2AF1, or XPO1 gene. In embodiments, the cancer-associated gene is a ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNF1A, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, or VHL gene. In embodiments, the cell is a cell (e.g., a T cell) within a tumor. In embodiments, the cell is a non-allogenic cell (i.e., native cell to the subject) within a tumor. In embodiments, the cell is a tumor infiltrating lymphocyte (TIL). In embodiments, the cell is an allogenic cell. In embodiments, the cell is a circulating tumor cell.

In embodiments, the cell is attached to the substrate via a bioconjugate reactive linker. In embodiments, the cell is attached to the substrate via a specific binding reagent. In embodiments, the specific binding reagent includes an antibody, single-chain Fv fragment (scFv), antibody fragment-antigen binding (Fab), or an aptamer. In embodiments, the specific binding reagent includes an antibody, or antigen binding fragment, an aptamer, affimer, or non-immunoglobulin scaffold. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. Substrates may be prepared for selective capture of particular cells. For example, a substrate containing a plurality of bioconjugate reactive moieties or a plurality of specific binding reagents, optionally in an ordered pattern, contacts a plurality of cells. Only cells containing complementary bioconjugate reactive moieties or complementary specific binding reagents are capable of reacting, and thus adhering, to the substrate.

In embodiments, the cell is immobilized to a substrate. Substrates can be two- or three-dimensional and can include a planar surface (e.g., a glass slide). A substrate can include glass (e.g., controlled pore glass (CPG)), quartz, plastic (such as polystyrene (low cross-linked and high cross-linked polystyrene), polycarbonate, polypropylene and poly(methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites. In embodiments, the substrate includes a polymeric coating, optionally containing bioconjugate reactive moieties capable of affixing the sample. Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a sample. In embodiments, the substrate is not a flow cell. In embodiments, the substrate includes a polymer matrix material (e.g., polyacrylamide, cellulose, alginate, polyamide, cross-linked agarose, cross-linked dextran or cross-linked polyethylene glycol), which may be referred to herein as a "matrix", "synthetic matrix", "exogenous polymer" or "exogenous hydrogel". In embodiments, a matrix may refer to the various components and organelles of a cell, for example, the cytoskeleton (e.g., actin and tubulin), endoplasmic reticulum, Golgi apparatus, vesicles, etc. In embodiments, the matrix is endogenous to a cell. In embodiments, the matrix is exogenous to a cell. In embodiments, the matrix includes both the intracellular and extracellular components of a cell. In embodiments, polynucleotide primers may be immobilized on a matrix including the various components and organelles of a cell. Immobilization of polynucleotide primers on a matrix of cellular components and organelles of a cell is accomplished as described herein, for example, through the interaction/reaction of complementary bioconjugate reactive moieties. In embodiments, the exogenous polymer may be a matrix or a network of extracellular components that act as a point of attachment (e.g., act as an anchor) for the cell to a substrate.

In embodiments, the cell is exposed to paraformaldehyde (i.e., by contacting the cell with paraformaldehyde). Any suitable permeabilization and fixation technologies can be used for making the cell available for the detection methods provided herein. In embodiments the method includes affixing single cells or tissues to a transparent substrate. Exemplary tissues include those from skin tissue, muscle tissue, bone tissue, organ tissue and the like. In embodiments, the method includes immobilizing the cell in situ to a substrate and permeabilized for delivering probes, enzymes, nucleotides and other components required in the reactions. In embodiments, the cell includes many cells from a tissue section in which the original spatial relationships of the cells are retained. In embodiments, the cell in situ is within a Formalin-Fixed Paraffin-Embedded (FFPE) sample. In embodiments, the cell is subjected to paraffin removal methods, such as methods involving incubation with a hydrocarbon solvent, such as xylene or hexane, followed by two or more washes with decreasing concentrations of an alcohol, such as ethanol. The cell may be rehydrated in a buffer, such as PBS, TBS or MOPs. In embodiments, the FFPE sample is incubated with xylene and washed using ethanol to remove the embedding wax, followed by treatment with Proteinase K to permeabilized the tissue. In embodiments, the cell is fixed with a chemical fixing agent. In embodiments, the chemical fixing agent is formaldehyde or glutaraldehyde. In embodiments, the chemical fixing agent is glyoxal or dioxolane. In embodiments, the chemical fixing agent includes one or more of ethanol, methanol, 2-propanol, acetone, and glyoxal. In embodiments, the chemical fixing agent includes formalin, Greenfix®, Greenfix® Plus, UPM, CyMol®, HOPE®, CytoSkelFix™, F-Solv®, FineFIX®, RCL2/KINFix, UMFIX, Glyo-Fixx®, Histochoice®, or PAXgene®. In embodiments, the cell is fixed within a synthetic three-dimensional matrix (e.g., polymeric material). In embodiments, the synthetic matrix includes polymeric-crosslinking material. In embodiments, the material includes polyacrylamide, poly-ethylene glycol (PEG), poly(acrylate-co-acrylic acid) (PAA), or Poly(N-isopropylacrylamide) (NIPAM).

In embodiments the cell is lysed to release nucleic acid or other materials from the cells. The cells may release, for instance, DNA, RNA, mRNA, proteins, or enzymes. For example, the cells may be lysed using reagents (e.g., a surfactant such as Triton-X or SDS, an enzyme such as lysozyme, lysostaphin, zymolase, cellulase, mutanolysin, glycanases, proteases, mannase, proteinase K, etc.) or a physical lysing mechanism a physical condition (e.g., ultrasound, ultraviolet light, mechanical agitation, etc.) (see, for example US Pat. Pub. 2021/0032618 for alternative lysis modalities, which is hereby incorporated by reference in its entirety). In some embodiments, the lysis reagent is a mixture including an amount of an ionic detergent and/or an amount of a base. In embodiments, the amounts of the ionic detergent and base in the mixture are effective concentration to release nucleic acid or other materials from the cells. In embodiments, the lysis reagent is added to cells and heated to at least about 50° C. In embodiments, the lysis reagent is added to cells and heated from at least about 50° C. to about 100° C. In embodiments, the cell and lysis reagent mixture is heated for at least 0.25 minutes. In embodiments, the cell and lysis reagent mixture is heated for at least 1 minute. In embodiments, the ionic detergent is one of sodium dodecyl sulfate (SDS), N-lauroylsarcosine sodium salt, or sodium deoxycholate. In some embodiments, the ionic detergent is present in the lysis reagent at a concentration from about 0.1% to about 10% by weight. In embodiments, the ionic detergent is sodium dodecyl sulfate (SDS) at a concentration of 1% by weight. In embodiments, the base is one of potassium hydroxide (KOH), lithium hydroxide (LiOH), sodium hydroxide (NaOH), rubidium hydroxide (RbOH), cesium hydroxide (CsOH), calcium hydroxide (Ca(OH)$_2$), strontium hydroxide (SR(OH)$_2$), or barium hydroxide (Ba(OH)$_2$). In some embodiments, the concentration of the base is from about 0.05 molar to about 1 molar. In some embodiments, the base is potassium hydroxide (KOH) at a concentration of about 0.2 molar. In some embodiments, after the cells are lysed with lysis reagent, the mixture is cooled from about 4° C. to about 40° C.

The cells may originate from any suitable source. For instance, the cells may be any cells for which nucleic acid from the cells is desired to be studied or sequenced, etc., and may include one, or more than one, cell type. The cells may be for example, from a specific population of cells, such as from a certain organ or tissue (e.g., cardiac cells, immune cells, muscle cells, cancer cells, etc.), cells from a specific individual or species (e.g., human cells, mouse cells, bacteria, etc.), cells from different organisms, cells from a naturally-occurring sample (e.g., pond water, soil, etc.), or the like. In some cases, the cells may be dissociated from tissue. In embodiments, the method does not include dissociating the cell from the tissue or the cellular microenvironment. In embodiments, the method does not include lysing the cell.

In embodiments, the method further includes subjecting the cell to expansion microscopy methods and techniques. Expansion allows individual targets (e.g., mRNA or RNA transcripts) which are densely packed within a cell, to be resolved spatially in a high-throughput manner. Expansion microscopy techniques are known in the art and can be performed as described in US 2016/0116384 and Chen et al., Science, 347, 543 (2015), each of which are incorporated herein by reference in their entirety.

In embodiments, the method does not include subjecting the cell to expansion microscopy. Typically, expansion microscopy techniques utilize a swellable polymer or hydrogel (e.g., a synthetic matrix-forming material) which can significantly slow diffusion of enzymes and nucleotides. Matrix (e.g., synthetic matrix) forming materials include polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art. Additionally, expansion microscopy techniques may render the temperature of the cell sample difficult to modulate in a uniform, controlled manner. Modulating temperature provides a useful parameter to optimize amplification and sequencing methods.

In embodiments, the method includes subjecting the cell to a polymer including a plurality of immobilized oligonucleotide primers (e.g., primers covalently attached to components within the matrix forming polymer). In embodiments, the method includes contacting the cell with a plurality of oligonucleotide primers that are capable of forming a covalent attachment to one or more cellular components; when the oligonucleotide primers form a covalent attachment to a cellular component, they may be referred to as immobilized oligonucleotide primers. In embodiments, the covalent attachment of the oligonucleotide primers to one or more cellular components does not require cross-linking. In embodiments, the attachment of the oligonucleotide primers to one or more cellular components includes hybridization of modified oligonucleotides (e.g., LNA-containing oligonucleotides that provide increased thermal hybridization stability). Non-limiting examples of covalent attachment include amine-modified polynucleotides within the primer reacting with epoxy or isothiocyanate groups within the matrix, succinylated polynucleotides within the primer reacting with aminophenyl or aminopropyl functional groups within the matrix, dibenzocyclooctyne-modified polynucleotides within the primer reacting with azide functional groups within the matrix (or vice versa), trans-cyclooctyne-modified polynucleotides within the primer reacting with tetrazine or methyl tetrazine groups within the matrix (or vice versa), disulfide modified polynucleotides within the primer reacting with mercapto-functional groups within the matrix, amine-functionalized polynucleotides within the primer reacting with carboxylic acid groups within the matrix or cellular component via 1-ethyl-3-(3-dimethylaminopropyl)-carbodiimide hydrochloride (EDC) chemistry, thiol-modified polynucleotides within the primer attaching to the matrix or cellular component via a disulfide bond or maleimide linkage, alkyne-modified polynucleotides within the primer attaching to a matrix via copper-catalyzed click reactions to azide functional groups within the matrix, azide-modified polynucleotides within the primer attaching to the matrix via copper-catalyzed click reactions to alkyne functional groups within the matrix, and acrydite-modified polynucleotides within the primer polymerizing with free acrylic acid monomers within the matrix to form polyacrylamide. In embodiments, the primer is attached to the matrix through electrostatic binding. For example, the negatively charged phosphate backbone of the primer may be bound electrostatically to positively charged monomers in the matrix.

In embodiments, the plurality of oligonucleotide primers form covalent attachments to one or more cellular components through bioconjugate reactive moieties. In embodiments, the 5' end of the primer contains a functional group that is capable of reacting with a complementary group so the primer may be tethered to a cellular component (e.g., a protein). In embodiments, the primers may be used to aid in tethering the extension product to a confined area and may not be extended. In embodiments, the immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the method includes extending the one or more immobilized oligonucleotides hybridized to an extension product with a polymerase. For example, the one or more immobilized oligonucleotides may be used to aid in tethering the extension product to a localized area and may be extended in an exponential RCA amplification reaction. In embodiments, the 5' end of the primer is covalently attached to a cellular component. In embodiments, the 5' end of the primer is covalently attached to the matrix. In embodiments, the 3' end of the primer is covalently attached to a cellular component. In embodiments, the 3' end of the primer is covalently attached to the matrix. The primers can include one or more reactive moieties. As used herein, the term reactive moiety includes any group capable of reacting with another molecule, e.g., a nucleic acid or polypeptide through covalent, non-covalent or other interactions. By way of example, the primer can include an amino acid reactive moiety that reacts with an amino acid on a protein or polypeptide through a covalent, non-covalent or other interaction.

In embodiments, the amplification method includes a standard dNTP mixture including dATP, dCTP, dGTP and dTTP (for DNA) or dATP, dCTP, dGTP and dUTP (for RNA). In embodiments, the amplification method includes a mixture of standard dNTPs and modified nucleotides that contain functional moieties (e.g., bioconjugate reactive groups) that serve as attachment points to the matrix in which the cell is embedded (e.g. a hydrogel). In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of crosslinking, the functional moiety is cross-linked to modified dNTP or dUTP or both. In embodiments, suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the matrix. In embodiments, suitable exemplary spacer moieties include polyethylene glycol, carbon spacers, photo-cleavable spacers and other spacers known to those of skill in the art and the like. In embodiments, amplification reactions include standard dNTPs and a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, during amplification a mixture of standard dNTPs and aminoallyl deoxyuridine 5'-triphosphate (dUTP) nucleotides may be incorporated into the amplicon and subsequently cross-linked to the cell protein matrix by using a cross-linking reagent (e.g., an amine-reactive crosslinking agent with PEG spacers, such as (PE-Gylated bis(sulfosuccinimidyl)suberate) (BS(PEG)9)).

In embodiments, the amplification primer and the sequencing primer includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers (e.g., amplification primer or sequencing primer) include nucleotides ranging from 17 to 30 nucleotides. In embodiments, the primer is at least 17 nucleotides, or alternatively, at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides, or alternatively at least 50 nucleotides, or alternatively at least 75 nucleotides or alternatively at least 100 nucleotides.

In embodiments, one or more nucleotides within the amplification primer sequence, the sequencing primer sequence, and/or the immobilized oligonucleotide primer contains one or more functional moieties (e.g., bioconjugate reactive groups) that serve as attachment points to the matrix in which the cell is embedded (e.g. a hydrogel). In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein). In embodiments, a plurality of oligonucleotide primers are provided to the matrix in which the cell is embedded prior to amplification. In embodiments, a plurality of oligonucleotide primers are provided to the matrix in which the cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as aminoallyl deoxyuridine 5'-triphosphate (dUTP) nucleotide(s). In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of crosslinking, the functional moiety is cross-linked to modified dNTP or dUTP or both. In embodiments, suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the matrix. In embodiments, suitable exemplary spacer moieties include polyethylene glycol, carbon spacers, photo-cleavable spacers and other spacers known to those of skill in the art and the like. In embodiments, the amplification primer and/or the sequencing primer contains a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, prior to amplification, the modified nucleotide-containing primer is attached to the cell protein matrix by using a cross-linking reagent (e.g., an amine-reactive cross-linking agent with PEG spacers, such as (PEGylated bis (sulfosuccinimidyl)suberate) (BS(PEG)9)).

In embodiments, the method includes hybridizing an oligonucleotide primer to a target nucleic acid (e.g., a the template polynucleotide) in a cell, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region; circularizing the oligonucleotide primer to generate a circular oligonucleotide, wherein circularizing includes extending the 3' end of the oligonucleotide primer along the target nucleic acid to generate a complementary sequence, and ligating the complementary sequence to the 5' end of the oligonucleotide primer; generating a partially double-stranded amplification product in a cell including a first strand hybridized to a second strand, wherein (i) the partially double-stranded amplification product includes multiple copies of the template polynucleotide, and (ii) the first strand and second strand are both immobilized to a cellular component or a matrix within the cell; generating a sequencing read by hybridizing one or more first sequencing primers to a single-stranded portion of the first strand, and extending the one or more first sequencing primers. In embodiments, the method further includes generating a second sequencing read by hybridizing one or more second sequencing primers to the second strand, and extending the one or more second sequencing primers.

In embodiments, a first invasion strand is generated by hybridizing an invasion primer to the second strand of the partially double-stranded amplification product, and extending the invasion primer, wherein the invasion primer is not covalently attached to the solid support; and generating a first sequencing read by hybridizing one or more sequencing primers to the first strand, and extending the one or more first sequencing primers. In embodiments, the method further includes removing the first invasion strand; generating a second invasion strand hybridized to the first strand by hybridizing a second invasion primer to the first strand, and extending the second invasion primer, wherein the second invasion primer is not covalently attached to the solid support; and generating a second sequencing read by hybridizing one or more second sequencing primers to the second strand, and extending the one or more second sequencing primers.

In embodiments, a first invasion strand is generated in situ by hybridizing an invasion primer to the second strand of the partially double-stranded amplification product, and extending the invasion primer, wherein the invasion primer is not immobilized to a cellular component or a matrix within the cell; and generating a first sequencing read by hybridizing one or more sequencing primers to the first strand, and extending the one or more first sequencing primers. In embodiments, the method further includes removing the first invasion strand; generating a second invasion strand hybridized to the first strand by hybridizing a second invasion primer to the first strand, and extending the second invasion primer, wherein the second invasion primer is not immobilized to a cellular component or a matrix within the cell; and generating a second sequencing read by hybridizing one or more second sequencing primers to the second strand, and extending the one or more second sequencing primers.

In embodiments, prior to generating a first invasion strand, the method includes removing immobilized primers that do not contain a first or second strand (i.e., unused primers). Methods of removing immobilized primers can include digestion using an enzyme with exonuclease activity. Removing unused primers may serve to increase the free volume and allow for greater accessibility of the invasion primer. Removal of unused primers may also prevent opportunities for the newly released first strand to rehybridize to an available surface primer, producing a priming site off the available surface primer, thereby facilitating the "reblocking" of the released first strand.

In embodiments, prior to generating a first invasion strand, the method includes blocking the immobilized primers that do not include a first or second strand. In embodiments, the immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, prior to generating a first invasion strand the method includes incubating the amplification products with dideoxynucleotide triphosphates (ddNTPs) to block the 3'-OH of the immobilized oligonucleotides from future extension.

In embodiments, the invasion primer includes a cleavable site. In embodiments, the cleavable site is located at the 3' end of the invasion primer. In embodiments, the method further includes cleaving the cleavable site in the invasion primer to generate a free 3' end within the invasion primer, removing the invasion strand, and generating a second sequencing read by extending the invasion primer.

In embodiments, the method further includes removing the first strand by cleaving the first strand at a cleavable site and generating a second sequencing read by hybridizing one or more second sequencing primers to the second strand; and extending the one or more second sequencing primers.

In embodiments, the first strand is cleaved after generating the first sequencing read but before generating the second sequencing read. In embodiments, the first strand is not cleaved after generating the first sequencing read. Cleaving one strand of the partially double-stranded amplification product may be referred to as linearization. Suitable methods for linearization are known, and described in more detail in application number U.S. Patent Publication 2009/0118128, which is incorporated herein by reference in its entirety. For example, the first strand may be cleaved by exposing the first strand to a mixture containing a glycosylase and one or more suitable endonucleases. In embodiments, the first strand is attached to the surface in a way that allows for selective removal. If the first template strand is removed from the surface, and the partially double-stranded amplification product is denatured, for example by treatment with hydroxide or formamide, then the second strand remains immobilized as a linearized single strand. If one of the surface immobilized primers includes a cleavable site such that it can be cleaved from the surface, (e.g., diol linkage) the resulting partially double-stranded amplification product can be made single-stranded using heat or chemical denaturing conditions to give a single strand containing a primer hybridization site.

Any suitable enzymatic, chemical, or photochemical cleavage reaction may be used to cleave the cleavable site. The cleavage reaction may result in removal of a part or the whole of the strand being cleaved. Suitable cleavage means include, for example, restriction enzyme digestion, in which case the cleavable site is an appropriate restriction site for the enzyme which directs cleavage of one or both strands of a duplex template; RNase digestion or chemical cleavage of a bond between a deoxyribonucleotide and a ribonucleotide, in which case the cleavable site may include one or more ribonucleotides; chemical reduction of a disulfide linkage with a reducing agent (e.g., THPP or TCEP), in which case the cleavable site should include an appropriate disulfide linkage; chemical cleavage of a diol linkage with periodate, in which case the cleavable site should include a diol linkage; generation of an abasic site and subsequent hydrolysis, etc. In embodiments, the cleavable site is included in the surface immobilized primer (e.g., within the polynucleotide sequence of the primer). In embodiments, one strand of the partially double-stranded amplification product (or the surface immobilized primer) may include a diol linkage which permits cleavage by treatment with periodate (e.g., sodium periodate). It will be appreciated that more than one diol can be included at the cleavable site. One or more diol units may be incorporated into a polynucleotide using standard methods for automated chemical DNA synthesis. Polynucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate (NaIO4). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine.

In embodiments, the cleavable site is not in the immobilized primer sequence (e.g., within the polynucleotide sequence of the primer). In embodiments, the cleavable site is included in the linking moiety responsible for tethering the primer to the substrate. In embodiments, the cleavable site is a cleavable linker (e.g., a disulfide containing linker that cleaves when exposed to a reducing agent).

In embodiments, the first strand includes at least one cleavable site. In embodiments, the first linker includes at least one cleavable site. In embodiments, the cleavable site includes deoxyuracil triphosphate (dUTP). The enzyme uracil DNA glycosylase (UDG) may then be used to remove dUTP, generating an abasic site on one strand. The polynucleotide strand including the abasic site may then be cleaved at the abasic site by treatment with endonuclease (e.g EndoIV endonuclease, AP lyase, FPG glycosylase/AP lyase, EndoVIII glycosylase/AP lyase), heat or alkali. In embodiments, the USER' reagent available from New England Biolabs (NEB catalog #M5508) is used for the creation of a single nucleotide gap at a uracil base in a duplex strand.

In embodiments, the cleavable site includes a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent.

In embodiments, the cleavable site includes one or more ribonucleotides. In embodiments, the cleavable site includes 2 to 5 ribonucleotides. In embodiments, the cleavable site includes one ribonucleotide. In embodiments, the cleavable site includes more than one ribonucleotide. In embodiments, the cleavable site includes deoxyuracil triphosphate (dUTP) or deoxy-8-oxo-guanine triphosphate (d-8-oxoG).

In embodiments, cleaving includes enzymatically cleaving the first strand at the at least one cleavable site (e.g., enzymatically cleaving with an endonuclease). In embodiments, the first strand includes a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent.

In embodiments, cleaving the first strand includes contacting the cleavable site with a cleaving agent, wherein the cleaving agent includes a reducing agent, sodium periodate, RNase, Formamidopyrimidine DNA Glycosylase (Fpg), endonuclease, restriction enzyme, or uracil DNA glycosylase (UDG). In embodiments, the cleaving agent is an endonuclease enzyme such as nuclease P1, AP endonuclease, T7 endonuclease, T4 endonuclease IV, Bal 31 endonuclease, Endonuclease I (endo I), Micrococcal nuclease, Endonuclease II (endo VI, exo III), nuclease BAL-31 or mung bean nuclease. In embodiments, the cleaving agent includes a restriction endonuclease, including, for example a type IIS restriction endonuclease. In embodiments, the cleaving agent is an exonuclease (e.g., RecBCD), restriction nuclease, endoribonuclease, exoribonuclease, or RNase (e.g., RNAse I, II, or III). In embodiments, the cleaving agent is a restriction enzyme. In embodiments, the cleaving agent includes a glycosylase and one or more suitable endonucleases. In embodiments, cleavage is performed under alkaline (e.g., pH greater than 8) buffer conditions at between 40° C. to 80° C.

In embodiments, cleaving includes chemically cleaving the first strand at the at least one cleavable site. In embodiments, the first linker includes a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent.

In embodiments, the invasion primer is not covalently attached to the solid support. In embodiments, the invasion primer includes synthetic nucleotides. In embodiments, the invasion primer includes locked nucleic acids (LNAs), Bis-locked nucleic acids (bisLNAs), twisted intercalating nucleic acids (TINAs), bridged nucleic acids (BNAs), 2'-O-methyl RNA:DNA chimeric nucleic acids, minor groove binder (MGB) nucleic acids, morpholino nucleic acids, C5-modified pyrimidine nucleic acids, peptide nucleic acids (PNAs), or combinations thereof. In embodiments, the invasion primer includes locked nucleic acids (LNAs), Bis-locked nucleic acids (bisLNAs), twisted intercalating nucleic acids (TINAs), bridged nucleic acids (BNAs), peptide nucleic acids (PNAs), or combinations thereof. In embodiments, the invasion primer includes locked nucleic acids (LNAs). In embodiments, the invasion primer includes Bis-locked nucleic acids (bisLNAs). In embodiments, the invasion primer includes twisted intercalating nucleic acids (TINAs). In embodiments, the invasion primer includes bridged nucleic acids (BNAs). In embodiments, the invasion primer includes 2'-O-methyl RNA:DNA chimeric nucleic acids. In embodiments, the invasion primer includes minor groove binder (MGB) nucleic acids. In embodiments, the invasion primer includes morpholino nucleic acids. In embodiments, the invasion primer includes C5-modified pyrimidine nucleic acids. In embodiments, the invasion primer includes peptide nucleic acids (PNAs). In embodiments, the invasion primer includes locked nucleic acids (LNAs), Bis-locked nucleic acids (bisLNAs), twisted intercalating nucleic acids (TINAs), bridged nucleic acids (BNAs), peptide nucleic acids (PNAs), or combinations thereof. In embodiments, the invasion primer includes from 5' to 3' a plurality of synthetic nucleotides (e.g., LNAs) followed by a plurality (e.g., 2 to 5) canonical nucleotides (e.g., dNTPs). In embodiments, the invasion primer comprises one or more (e.g., 2 to 5) deoxyuracil nucleobases (dU). In embodiments, the one or more dU nucleobases are at or near the 3' end of the invasion primer (e.g., within 5 nucleotides of the 3' end). In embodiments, the invasion primer includes from 5' to 3' a plurality (e.g., 2 to 5) of phosphorothioate nucleotides, followed by a plurality of synthetic nucleotides (e.g., LNAs), and subsequently followed by a plurality (e.g., 2 to 5) of canonical bases. In some embodiments, the invasion primer includes a plurality of canonical bases, wherein the canonical bases terminate (i.e., at the 3' end) with a deoxyuracil nucleobase (dU).

In embodiments, the invasion primer includes one or more morpholino nucleic acids. Morpholino nucleic acids are synthetic nucleotides that have standard nucleic acid bases (e.g., adenine, guanine, cytosine, and thymine) wherein those bases are bound to methylenemorpholine rings linked through phosphorodiamidate groups instead of phosphates. Morpholino nucleic acids may be referred to as phosphorodiamidate morpholino oligomers (PMOs).

In embodiments, the invasion primer includes locked nucleic acids (LNAs), or peptide nucleic acids (PNAs). In embodiments, the invasion primer includes LNAs dispersed throughout the primer, wherein at least 2 to 5 nucleotides on the 3' end are canonical dNTPs. In embodiments, the entire composition of the invasion primer includes less than 50%, less than 40%, or less than 30% of LNAs.

In embodiments, the invasion primer is about 10 to 100 nucleotides in length. In embodiments, the invasion primer is about 15 to about 75 nucleotides in length. In embodiments, the invasion primer is about 25 to about 75 nucleotides in length. In embodiments, the invasion primer is about 15 to about 50 nucleotides in length. In embodiments, the invasion primer is about 10 to about 20 nucleotides in length. In embodiments, the invasion primer is about 10, 11, 12, 13, 14, 15, 16, 17, 18, 19, or about 20 nucleotides in length. In embodiments, the invasion primer is about 20, 21, 22, 23, 24, 25, 26, 27, 28, 29, or about 30 nucleotides in length. In embodiments, the invasion primer is about 30, 31, 32, 33, 34, 35, 36, 37, 38, 39, or about 40 nucleotides in length. In embodiments, the invasion primer is about 40, 41, 42, 43, 44, 45, 46, 47, 48, 49, or about 50 nucleotides in length. In embodiments, the invasion primer is greater than 30 nucleotides in length. In embodiments, the invasion primer is greater than 40 nucleotides in length. In embodiments, the invasion primer is greater than 50 nucleotides in length.

In embodiments, generating the invasion strand includes a plurality of invasion primer extension cycles. In embodiments, generating the invasion strand includes extending the invasion primer by incorporating one or more nucleotides (e.g., dNTPs) using Bst large fragment (Bst LF) polymerase, Bst2.0 polymerase, Bsu polymerase, SD polymerase, Vent exo-polymerase, Phi29 polymerase, or a mutant thereof.

In embodiments, generating the invasion strand includes a plurality of invasion-primer extension cycles by incorporating universal nucleobases (e.g., 5-nitroindole and/or inosine nucleobases) into the invasion primer. The blocking strand does not need to be a faithful representation (i.e., an exact copy) of the strand to which the invasion primer is hybridized. In the interest of speed, in embodiments, one or more inosine nucleotides may be incorporated into the primer to generate a blocking strand. In embodiments, the blocking strand includes universal nucleobases. In embodiments, the invasion strand is generated using an error-prone polymerase, for example Taq, a Y-family member Dpo4, or others known in the art (e.g., Rattray A J and Strathern J N. Annu Rev Genet. 2003; 37:31-66). In embodiments, the blocking strand is not a copy of the strand the invasion primer is hybridized to. In embodiments, the blocking strand does not replicate the exact sequence of the strand to which the invasion primer is hybridized.

In embodiments, generating the invasion strand includes a first plurality of invasion-primer extension cycles followed by a second plurality of invasion-primer extension cycles, wherein the reaction conditions for the first plurality of invasion-primer extension cycles are different than the second plurality of invasion-primer extension cycles. In embodiments, generating the invasion strand includes alternating between a first plurality of invasion-primer extension cycles and a second plurality of invasion-primer extension cycles, wherein the reaction conditions for the first plurality of invasion-primer extension cycles are different than the second plurality of invasion-primer extension cycles. In embodiments, the reaction conditions for the first plurality of invasion-primer extension cycles include higher stringency hybridization conditions relative to the second plurality of invasion-primer extension cycles.

In embodiments, the reaction conditions for the first plurality of invasion-primer extension cycles include incubation in a first denaturant. In embodiments, the first denaturant includes additives such as ethylene glycol, polyethylene glycol, 1,2-propanediol, dimethyl sulfoxide (DMSO), glycerol, formamide, 7-deaza-dGTP, acetamide, betaine, or tetramethylammonium chloride (TMAC). In embodiments, the first denaturant is a buffered solution including about 0% to about 50% dimethyl sulfoxide (DMSO); about 0% to about 50% ethylene glycol; about 0% to about 20% formamide; or about 0 to about 3M betaine, or a mixture thereof. In embodiments, the reaction conditions for the first plurality of invasion-primer extension cycles include incubation in a first denaturant, wherein the first denaturant is a buffered solution including about 15% to about 50% dimethyl sulfoxide (DMSO); about 15% to about 50% ethylene glycol; about 10% to about 20% formamide; or about 0 to about 3M betaine, or a mixture thereof.

In embodiments, the reaction conditions for the second plurality of invasion-primer extension cycles include incubation in a second denaturant. In embodiments, the second denaturant includes additives such as ethylene glycol, polyethylene glycol, 1,2-propanediol, dimethyl sulfoxide (DMSO), glycerol, formamide, 7-deaza-dGTP, acetamide, betaine, or tetramethylammonium chloride (TMAC), wherein the concentrations of the additives in the second denaturant differ than the concentrations of the additives in the first denaturant. In embodiments, the second denaturant is a buffered solution including about 0 to about 50% dimethyl sulfoxide (DMSO); about 0 to about 50% ethylene glycol; about 0 to about 20% formamide; or about 0 to about 3M betaine, or a mixture thereof. In embodiments, the reaction conditions for the second plurality of invasion-primer extension cycles include incubation in a second denaturant, wherein the second denaturant is a buffered solution including about 0% to about 15% dimethyl sulfoxide (DMSO); about 0 to about 15% ethylene glycol; about 0 to about 10% formamide; or about 0 to about 3M betaine, or a mixture thereof.

In embodiments, the first denaturant is a buffered solution including dimethyl sulfoxide (DMSO); and the second denaturant is a buffered solution including dimethyl sulfoxide (DMSO) and betaine. In embodiments, the first denaturant is a buffered solution including about 25 to about 35% DMSO; and the second denaturant is a buffered solution including about 0 to about 10% DMSO and about 1M to about 4M betaine. In embodiments, the first denaturant is a buffered solution including about 30% DMSO; and the second denaturant is a buffered solution including about 5% DMSO, about 2.5M betaine.

In embodiments, the reaction conditions for the second plurality of invasion-primer extension cycles further includes incubation with a SSB protein.

In embodiments, generating the invasion strand includes contacting the partially double-stranded amplification product with one or more invasion-reaction mixtures; each of the invasion-reaction mixture including a plurality of invasion primers, a plurality of deoxyribonucleotide triphosphate (dNTPs), and a polymerase. In embodiments, generating the invasion strand includes contacting the partially double-stranded amplification product with a first invasion-reaction mixture followed by contacting the partially double-stranded amplification product with a second invasion-reaction mixture; the first invasion-reaction mixture including a plurality of invasion primers and no polymerase; and the second invasion-reaction mixture includes a plurality of deoxyribonucleotide triphosphate (dNTPs) and a polymerase. In embodiments, the polymerase is a strand-displacing polymerase. In embodiments, the strand-displacing polymerase is Bst large fragment (Bst LF) polymerase, Bst 3.0 polymerase, Bst2.0 polymerase, Bsu polymerase, SD polymerase, Vent exo-polymerase, Phi29 polymerase, or a mutant thereof.

In embodiments, each invasion-reaction mixture further includes a denaturant, single-stranded DNA binding protein (SSB), or a combination thereof. In embodiments, each invasion-reaction mixture includes a different amount of a denaturant, single-stranded DNA binding protein (SSB), or a combination thereof.

In embodiments, the denaturant is a buffered solution including betaine, dimethyl sulfoxide (DMSO), ethylene glycol, formamide, glycerol, guanidine thiocyanate, 4-methylmorpholine 4-oxide (NMO), TMAC, or a mixture thereof. In embodiments, the denaturant is a buffered solution including betaine, dimethyl sulfoxide (DMSO), ethylene glycol, formamide, or a mixture thereof.

In embodiments, each invasion-reaction mixture includes a denaturant including an SSB, a strand-displacing polymerase, and one or more crowding agents. In embodiments, the denaturant does not include a chemical denaturant (e.g., betaine, DMSO, ethylene glycol, formamide, guanidine thiocyanate, NMO, TMAC, or a mixture thereof). In embodiments, the SSB in the denaturant is T4 gp32 protein, SSB protein, T7 gene 2.5 SSB protein, or phi29 SSB protein, *Thermococcus kodakarensis* (KOD) SSB, *Thermus thermophilus* (TTH) SSB, *Sulfolobus solfataricus* (SSO) SSB, or Extreme Thermostable Single-Stranded DNA Binding Protein (ET-SSB). In embodiments, the strand-displacing polymerase in the denaturant is Bst large fragment (Bst LF) polymerase, Bst 3.0 polymerase, Bst2.0 polymerase, Bsu polymerase, SD polymerase, Vent exo-polymerase, Bsm DNA Polymerase, Phi29 polymerase, or a mutant thereof. In embodiments, the crowding agent in the denaturant is poly (ethylene glycol) (e.g., PEG 200, PEG 600, PEG 800, PEG 2,050, PEG 4,600, PEG 6,000, PEG 8,000, PEG 10,000, PEG 20,000, or PEG 35,000). In embodiments, PEG is present in the denaturant at a concentration of 1% to 25%. In embodiments, PEG is present in the denaturant at a concentration of about 1%, about 5%, about 10%, about 15%, about 20%, or about 25%. In embodiments, the denaturant is a buffered solution including T4 gp32 protein, Bsu polymerase, and 5 to 10% PEG 20,000. In embodiments, the denaturant is a buffered solution including T4 gp32 protein, Bsu polymerase, and 5% PEG 20,000. In embodiments, the denaturant is a buffered solution including T4 gp32 protein, Bsu polymerase, and 10% PEG 20,000.

In embodiments, the SSB is T4 gp32 protein, SSB protein, T7 gene 2.5 SSB protein, or phi29 SSB protein, *Thermococcus kodakarensis* (KOD) SSB, *Thermus thermophilus* (TTH) SSB, *Sulfolobus solfataricus* (SSO) SSB, or Extreme Thermostable Single-Stranded DNA Binding Protein (ET-SSB). In embodiments, the SSB is active (i.e., has measurable activity) at temperatures less than about 72° C. In embodiments, the SSB is active (i.e., has measurable activity) at temperatures about 72° C. In embodiments, the SSB is active (i.e., has measurable activity) at temperatures greater than about 72° C.

Complexes and Kits

In an aspect, provided herein is a complex including a polynucleotide and a solid support. In embodiments, the complex includes one or more elements described herein with regard to any of the various methods described herein. In embodiments the complex includes (a) a partially double-stranded amplification product including a first strand hybridized to a second strand, wherein (i) the partially double-stranded amplification product includes multiple copies of a template polynucleotide, and (ii) the first strand and second strand are both covalently attached to a solid surface; and (b) one or more first sequencing primer extension products hybridized to a single-stranded portion of the first strand, wherein the sequencing primer extension product includes a modified nucleotide; and (c) one or more polymerases. The modified nucleotides may carry a label to facilitate their detection. In embodiments, the label is a fluorescent label. Each nucleotide type may carry a different fluorescent label. However, the detectable label need not be a fluorescent label. Any label can be used which allows the detection of the incorporation of the nucleotide into the DNA sequence.

In an aspect, provided herein is a complex including a polynucleotide and a solid support. In embodiments, the complex includes one or more elements described herein with regard to any of the in situ methods described herein. In embodiments the complex includes (a) a partially double-stranded amplification product including a first strand hybridized to a second strand, wherein (i) the partially double-stranded amplification product includes multiple copies of a template polynucleotide, and (ii) the first strand and second strand are both immobilized to a cellular component or a matrix (e.g., a synthetic matrix) within the cell; and (b) one or more first sequencing primer extension products hybridized to a single-stranded portion of the first strand, wherein the sequencing primer extension product includes a modified nucleotide; and (c) one or more polymerases. The modified nucleotides may carry a label to facilitate their detection. In embodiments, the label is a fluorescent label. Each nucleotide type may carry a different fluorescent label. However, the detectable label need not be a fluorescent label. Any label can be used which allows the detection of the incorporation of the nucleotide into the DNA sequence.

In embodiments, the template polynucleotide of (a) is a circular polynucleotide that is about 100 to about 1000 nucleotides in length, about 100 to about 300 nucleotides in length, about 300 to about 500 nucleotides in length, or about 500 to about 1000 nucleotides in length. In embodiments, the circular polynucleotide is about 300 to about 600 nucleotides in length.

In embodiments, the template polynucleotide includes one or more adapters. In embodiments, the one or more adapters include a hairpin loop structure. In some embodiments, a hairpin adapter comprises a single nucleic acid strand comprising a stem-loop structure. A hairpin adapter can be any suitable length. In some embodiments, a hairpin adapter is at least 40, at least 50, or at least 100 nucleotides in length. In some embodiments, a hairpin adapter has a length in a range of 45 to 500 nucleotides, 75-500 nucleotides, 45 to 250 nucleotides, 60 to 250 nucleotides or 45 to 150 nucleotides. In some embodiments, a hairpin adapter comprises a nucleic acid having a 5'-end, a 5'-portion, a loop, a 3'-portion and a 3'-end (e.g., arranged in a 5' to 3' orientation). In some embodiments, the 5' portion of a hairpin adapter is annealed and/or hybridized to the 3' portion of the hairpin adapter, thereby forming a stem portion of the hairpin adapter. In some embodiments, the 5' portion of a hairpin adapter is substantially complementary to the 3' portion of the hairpin adapter. In certain embodiments, a hairpin adapter comprises a stem portion (i.e., stem) and a loop, wherein the stem portion is substantially double stranded thereby forming a duplex. In some embodiments, the loop of a hairpin adapter comprises a nucleic acid strand that is not complementary (e.g., not substantially complementary) to itself or to any other portion of the hairpin adapter. In some embodiments, a loop of a hairpin adapter comprise one or more of a primer binding site, a capture nucleic acid binding site (e.g., a nucleic acid sequence complementary to a capture nucleic acid), a UMI, a sample barcode, a sequencing adapter, a label, the like or combinations thereof. In certain embodiments, a loop of a hairpin adapter comprises a primer binding site. In certain embodiments, a loop of a hairpin adapter comprises a primer binding site and a UMI.

In embodiments, the complex includes one or more polymerases. In embodiments, the complex includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol α, DNA polymerase, Pol δ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes).

In embodiments, the complex includes a strand-displacing polymerase. In embodiments, the complex includes a strand-displacing polymerase, such as a phi29 polymerase, phi29 mutant polymerase or a thermostable phi29 mutant polymerase.

In embodiments, the complex further includes an additive that lowers a DNA denaturation temperature. In embodiments, the complex includes an additive such as betaine, dimethyl sulfoxide (DMSO), ethylene glycol, formamide, glycerol, guanidine thiocyanate, 4-methylmorpholine 4-oxide (NMO), or a mixture thereof.

In embodiments, the solid support is glass or quartz, such as a microscope slide, having a surface that is uniformly silanized. This may be accomplished using conventional protocols e.g., Beattie et a (1995), Molecular Biotechnology, 4: 213. Such a surface is readily treated to permit end-attachment of primers (e.g., forward and reverse primers, and/or an amplification primer) prior to amplification. In embodiments the solid support surface further includes a polymer coating, which contains functional groups capable of immobilizing primers. In some embodiments, the solid support includes a patterned surface suitable for immobilization of primers in an ordered pattern. A patterned surface refers to an arrangement of different regions in or on an exposed layer of a solid support. For example, one or more of the regions can be features where one or more primers are present. The features can be separated by interstitial regions where capture primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. In some embodiments, the primers are randomly distributed upon the solid support. In some embodiments, the primers are distributed on a patterned surface. In embodiments, the solid support is planar.

In an aspect is provided a kit containing a complex as described herein, including embodiments. Generally, the kit includes one or more containers providing a complex, composition, and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, labeled nucleotides, and/or modified nucleotides), buffers, salts, and/or labels (e.g., fluorophores). In embodiments, the kit includes components useful for circularizing template polynucleotides using a ligation enzyme (e.g., Circligase enzyme, Taq DNA Ligase, HiFi Taq DNA Ligase, T4 ligase, or Ampligase DNA Ligase). For example, such a kit further includes the following components: (a) reaction buffer for controlling pH and providing an optimized salt composition for a ligation enzyme (e.g., Circligase enzyme, Taq DNA Ligase, HiFi Taq DNA Ligase, T4 ligase, or Ampligase DNA Ligase), and (b) ligation enzyme cofactors. In embodiments, the kit further includes instructions.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

EXAMPLES

Example 1. An Efficient Approach to Sequencing Two Strands of the Same Polynucleotide Before a target nucleic acid is sequenced, some degree of DNA pre-processing into a library is typically required. For example, these steps may involve fragmenting input polynucleotides into an appropriate platform-specific size range, followed by an end-polishing step to generate blunt ended DNA fragments. Specific adapters are then ligated to these fragments. A functional library typically includes having specific adapter sequences added to the 3' and 5' ends to ensure compatibility with the underlying flow cell, so it may be amplified appropriately.

Current SBS platforms require clonal amplification of the initial template molecules with a cluster (i.e., polonies) to increase the signal-to-noise ratio because the systems are not sensitive enough to detect the extension of one base at the individual DNA template molecule level. Standard amplification methods employed in commercial sequencing devices (e.g., solid-phase bridge amplification) typically amplify a template using surface immobilized primers to produce a plurality of double-stranded nucleic acid molecules, wherein at least one strand of each double-stranded nucleic acid molecule is attached to the solid support at its 5' ends. A common method of doing solid-phase amplification involves bridge amplification methodologies (referred to as bridge PCR) as exemplified by the disclosures of U.S. Pat. Nos. 5,641,658; 7,115,400; 7,790,418; U.S. Patent Publ. No. 2008/0009420, each of which is incorporated herein by reference in its entirety. In sum, bridge amplification methods allow amplification products (e.g., amplicons) to be immobilized on a solid support in order to form arrays comprised of colonies (or "clusters") of immobilized nucleic acid molecules. Each cluster or colony on such an array is formed from a plurality of identical immobilized polynucleotide strands and a plurality of identical immobilized complementary polynucleotide strands. The products of solid-phase amplification reactions are referred to as "bridged" structures when formed by annealed pairs of immobilized polynucleotide strands and immobilized complementary strands, both strands being immobilized on the solid support at the 5' end, preferably via a covalent attachment. During bridge PCR, additional chemical additives may be included in the reaction mixture, in which the DNA strands are denatured by flowing a denaturant such as formamide or NaOH over the DNA, which chemically denatures complementary strands. This is followed by washing out the denaturant and reintroducing a polymerase in buffer conditions that allow primer annealing and extension.

However, the typical amplification methods used in commercial sequencing devices suffer from a number of disadvantages. For example, standard bridge PCR produces amplicons which have limited efficiency of re-priming (~30%) due to the spatial proximity of amplicons to their reverse complement strands. It is more energetically favorable for the two strands to remain hybridized together, and compounded with the limited mobility of the sequencing primers, the amplicons favor reannealing of full-length complementary strands as opposed to primer annealing. Therefore, in order to provide more suitable templates for nucleic acid sequencing it is preferred to remove substantially all or at least a portion of one of the immobilized strands in the "bridged" structure in order to generate a template which is at least partially single-stranded. The portion of the template which is single-stranded will thus be available for hybridization to a sequencing primer. The process of removing all or a portion of one immobilized strand in a "bridged" double-stranded nucleic acid structure may be referred to herein as "linearization". Bridged template structures may be linearized by cleavage of one or both strands with a restriction endonuclease or by cleavage of one strand with a nicking endonuclease. Other methods of cleavage can be used as an alternative to restriction enzymes or nicking enzymes, including chemical cleavage (e.g. cleavage of a diol linkage with periodate), cleavage of abasic sites by cleavage with endonuclease, or by exposure to heat or alkali, cleavage of ribonucleotides incorporated into amplification products otherwise comprised of deoxyribonucleotides, photochemical cleavage or cleavage of a peptide linker. Alternatively, the primers may be attached to the solid surface with a cleavable linker, such that upon exposure to a cleaving agent, all or a portion of the primer is removed from the surface.

Dual-read sequencing, that is sequencing a first strand and a second strand of a double-stranded polynucleotide, gathers nucleotide information from two "reads" of a double stranded polynucleotide. Within commercial platforms capable of performing dual-read sequencing-by-synthesis workflows (e.g., Illumina MiSeq™), the amplicon strands within monoclonal clusters contain a single copy of the forward or reverse strand, i.e. the amplicons are non-concatemeric. For example, such amplicons generated within the cluster using bridge PCR or recombinase polymerase amplification (RPA). Because of the relatively short length of these amplicons, and their density (i.e., their close proximity within a cluster on the flow cell surface), the configuration of these amplicons after cluster amplification is in double-stranded DNA (dsDNA) format. Hybridizing a sequencing primer directly into dsDNA is challenging, necessitating cleaving and removing either the forward or the reverse strands of the amplicons, thereby creating ssDNA to allow for hybridization of a sequencing primer. Following hybridization of the sequencing primer, a first sequencing read of either reverse or forward amplicons is completed (i.e., an appropriate read length is obtained), and the amplicon sequence that was initially cleaved must be regenerated prior to starting the second read. This can be done by additional amplification steps, such as additional rounds of bridge PCR. All of these steps add complexity and time to the DNA sequencing workflow.

In contrast, in amplification and sequencing methods described herein, the concatemeric forward and reverse amplicons that are created are longer as compared to the conventional methods (e.g., the methods mentioned above). The longer concatemeric forward and reverse amplicons fold over and do not consistently form full-length dsDNA molecules (i.e., there are regions of ssDNA and dsDNA). This enables greater reach because of the longer initial amplicons, and allows for hybridization of free 3' ends not only to other solid-phase DNA primers, but also to a complementary region of other DNA amplicons. This enhances the amount of re-priming/hybridization events, which greatly enhances the amplification and sequencing efficiency compared to amplification with amplicon strands that contain only one copy of the initial nucleic acid molecule.

Importantly, using an amplification method which produces a forward and reverse concatemers enables the amplicons to be configured within a monoclonal cluster in a way that allows a sequencing primer to be hybridized directly to the amplicons without cleaving off the forward or the reverse amplicons. This permits sequencing of two distinct regions, one at each end of the complementary strands of a target polynucleotide duplex, thereby doubling the sequencing throughput that allow for very high accuracy results and sequencing depth.

Due to accuracy and phasing limitations, some implementations of SBS technologies are limited to about 100 to 150 base pairs. Under ideal circumstances, all bases within a cluster will be extended in phase. However, a small portion of the molecules do not extend properly and fall either behind (phasing) or advance a base (pre-phasing). Over many cycles, these errors will accumulate and decrease the signal to noise ratio per cluster, causing a decrease in quality towards the ends of the reads. In embodiments where the first strand contains complementarity to the second strand (e.g., initial template sizes 50 to 150 base pairs), there is significantly more information to be gained from sequencing two stretches from a single double stranded template than from sequencing from each of two independent templates in a random fashion. Not only does it greatly enhance assembly of the sequence information, dual-read sequencing improves the ability resolve structural rearrangements such as gene insertions, deletions, or inversions. In embodiments where the first strand contains limited, if any, complementarity to the second strand (e.g., initial template sizes 200 to 600 base pairs) such that there is limited overlap between the sequenced strands, dual read sequencing can provide information useful for de novo sequencing or for studying complex genomic rearrangements.

Utilizing two different amplification methods to generate partially double-stranded amplification products, i) exponential rolling circle amplification (eRCA) and a ii) hybrid (i.e., a combination of two distinct amplification steps, such as initial amplification via eRCA followed by successive rounds of thermal bridge PCR), we demonstrated that dual-read sequencing can be achieved without the need for cleaving the opposite strand.

The first amplification method produced monoclonal clusters using exponential rolling circle amplification (eRCA). Circular DNA templates (300-600 nucleotides long), were hybridized in Tris HCl buffer with NaCl to a solid support (e.g., a flow cell) that contained forward and reverse nucleic acid primers (20 to 25 nucleotides long). Barbell-shaped template DNA molecules, formed by ligating hairpin adapters to both ends of the DNA template, can be used for this purpose as well. The surface-bound primers for DNA amplification contained phosphorothioates at the 3' end and one of the two surface-bound primers contained a cleavable moiety (e.g., a diol functional group). The template was extended with a mutant phi29 enzyme (e.g., EquiPhi polymerase) for 2 minutes, or 10 minutes to generate a complement to the template. The template was removed using 0.1 M NaOH at room temperature.

The second amplification protocol is a method for amplifying single template nucleic acid molecules on a solid-phase without thermal cycling (i.e., the hybrid method described above). Circular DNA templates (300-600 nucleotides long) were hybridized in Tris HCl buffer with NaCl to a solid support (e.g., a flow cell) that contains forward and reverse nucleic acid primers (20 to 25 nucleotides long). The surface-bound primers for DNA amplification contained phosphorothioates at the 3' end and one of the two surface-bound primers contained a cleavable moiety (e.g., a diol functional group). The template was extended with a mutant phi29 enzyme (e.g., EquiPhi polymerase) for 0.5 minutes, 2 minutes, or 10 minutes to generate a complement to the template. The template was removed using 0.1 M NaOH at room temperature. The extended primers were then subjected to 45 cycles of chemical bridge polymerase chain reaction (c-bPCR) using a Bst DNA Polymerase, Large Fragment (Bsf LF) for the extension step wherein solutions of 100% formamide were cycled in and out of the reaction vessel. One cycle included extending using Bst LF in an extension mix (e.g., 1× Thermopol Buffer, dNTPs, etc.) for 60 seconds, followed by flowing in 100% formamide for 60 seconds. Note, 60 seconds of exposure was used in this experiment, but shorter times can be used. Extension and denaturation times can be at least 15 seconds each, but greater than 30 seconds is preferred. The c-PCR cycles comprise an extension step (e.g., extending using Bst LF in an extension mix (e.g., 1× Thermopol Buffer, dNTPs, etc.)) and a denaturation step (e.g., exposing the extension products to 100% formamide), and optionally a washing solution is flowed between the extension and denaturation step. The temperature of the reaction is performed at temperatures of about 40° C. to 58° C.

The monoclonal clusters can proceed to any necessary post-processing steps such as blocking of free 3' ends, removal of select amplicons, or hybridization of a sequencing primer. The clusters described above were quantified by introducing a nucleic acid stain (e.g., SYBR® Gold stain available from Thermo Fisher, Catalog #S11494 or a FAM (6-fluorescein amidite) labeled oligonucleotide) in the presence of a Tris-EDTA buffer, and allowed to incubate with the amplicons for 10 minutes. After a wash, the substrate containing the stained amplicons was imaged and subjected to post-processing analysis to determine cluster size and brightness. After these steps, clusters were ready for sequencing in a sequencing-by-synthesis system.

Example 2. Dual-Sequencing the Clusters

In another aspect is provided methods of sequencing amplified nucleic acids, optionally generated by the amplification methods described herein. As described above, arrays comprised of traditional double-stranded bridged structures provide inefficient templates for nucleic acid sequencing, since hybridization of a conventional sequencing primer to one of the immobilized strands is not preferred compared to annealing of this strand to its immobilized complementary strand under standard conditions for hybridization. Traditionally, in order to provide more suitable templates for nucleic acid sequencing it is preferred to remove substantially all or at least a portion of one of the immobilized strands in the "bridged" structure in order to generate a template which is at least partially single-stranded and thus be available for hybridization to a sequencing primer. For example, during sequencing only one strand of the amplicon (e.g., the forward strand or the reverse strand) may be present. By contrast, the method of the present example does not include removing all or a portion of one immobilized strand of the double-stranded nucleic acid structure (i.e. linearizing) prior to sequencing (i.e., during sequencing the amplification product retains at least partial double-stranded nature).

As described above, the amplification methods produced clusters of oligonucleotides for sequencing. The initiation point for the first sequencing reaction was provided by annealing a sequencing primer complementary to a region within one of the strands. In the presence of an enzyme (e.g., a DNA polymerase), nucleotides (e.g., labeled nucleotides) are incorporated and detected such that the identity incorporated nucleotides allow for the identification of the first strand. Thus, the first sequencing reaction may include hybridizing a sequencing primer to a region of an amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand. Note, the second sequenced strand is present while sequencing the first strand.

Next, a second sequencing reaction is initiated by annealing a sequencing primer complementary to a region in the second strand, and in the presence of an enzyme (e.g., a DNA polymerase), nucleotides (e.g., labeled nucleotides) are incorporated and detected such that the identity incorporated nucleotides allow for the identification of the second template strand. Thus, the second sequencing reaction may include hybridizing a sequencing primer to a region of an amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

Experiments were performed that sequenced the first strand in the presence of the second strand (i.e., the full second strand was immobilized to the support during sequencing of the first strand), then the second strand was sequenced in the presence of the first strand (i.e., the full first strand, and the sequencing generated complement thereof are present during sequencing). An additional experiment was performed where the first strand is sequenced, followed by cleaving and removing the first strand and the sequencing generated complement thereof prior to sequencing the second strand.

Figure 2:
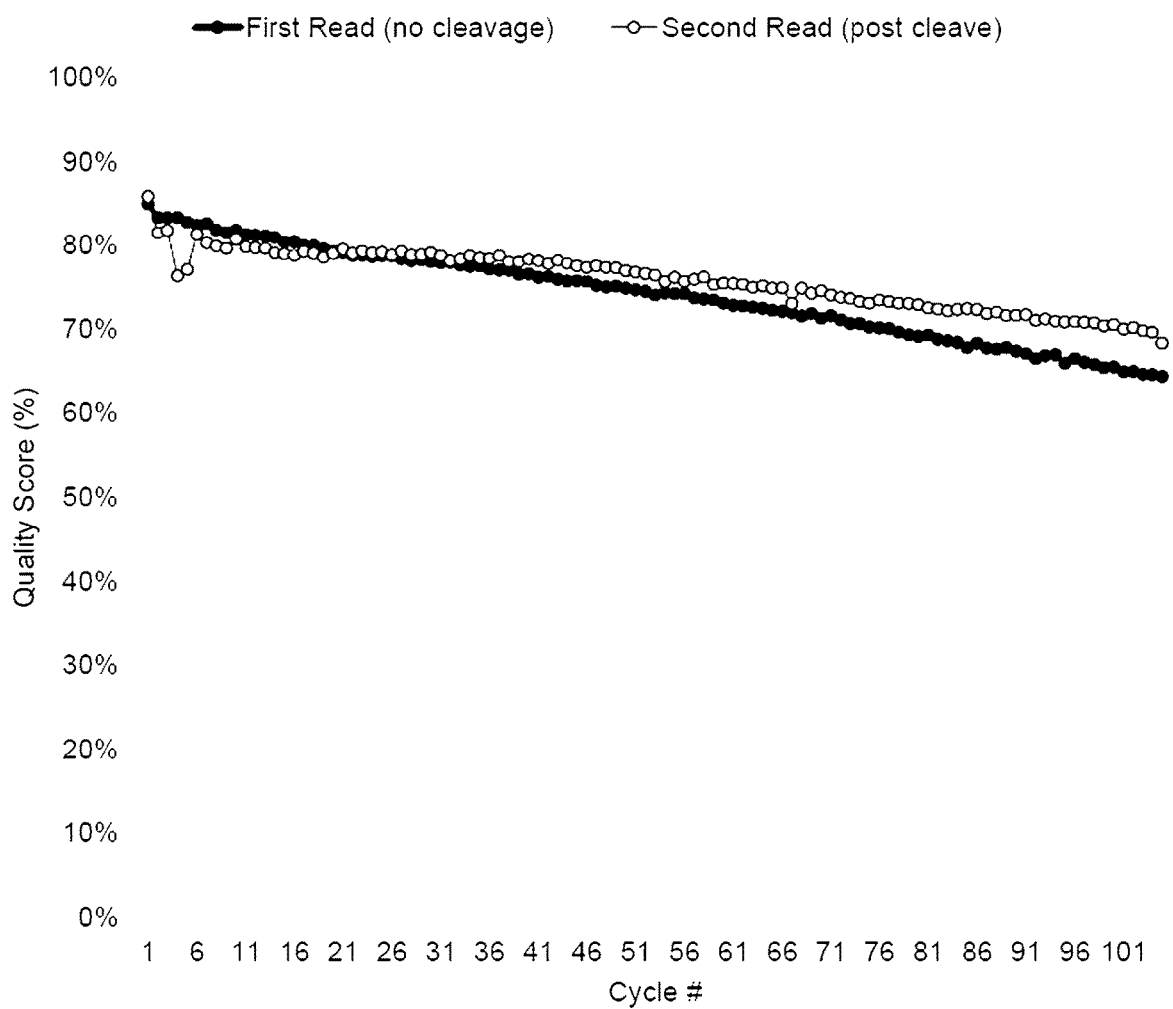
FIG. 2. Sequencing quality scores for a 100-cycle sequencing run. Quality scores quantify the degree of confidence that a base within a sequencing read is called correctly. As observed in FIG. 2, the quality scores remain relatively invariant for a plurality of sequencing cycles using a dual-read sequencing method as described herein.
Figure 3:
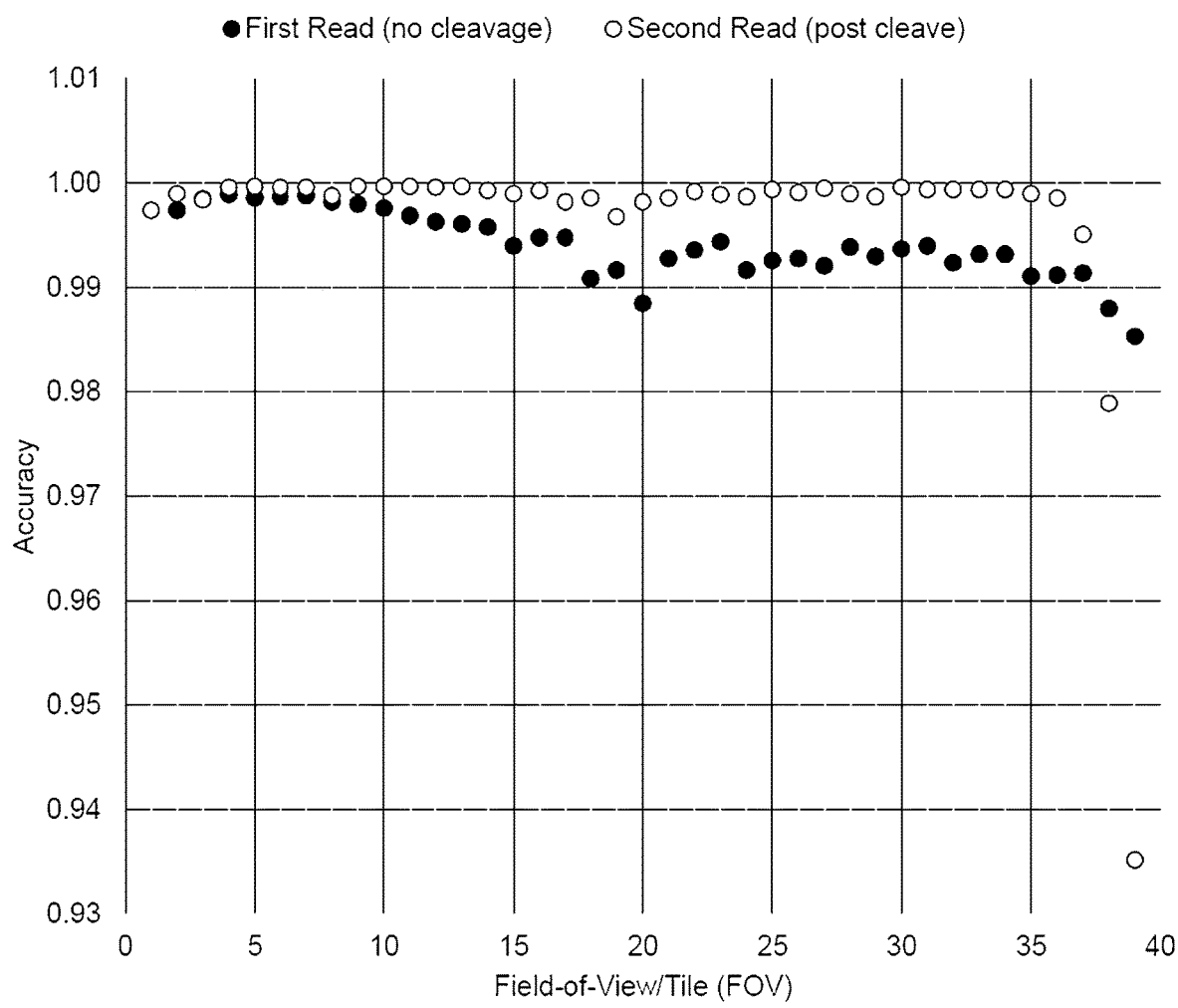
FIG. 3. Sequencing accuracy data for sequencing two strands of the same polynucleotide for multiple fields of view. The first read is completed in the presence of the first and the second strand. The second read is completed following cleavage of the first strand.

Sequencing quality scores assign (shown in FIG. 2 for a 100-cycle sequencing run) confidence to a particular base within a sequencing read by quantifying the probability that a base is called incorrectly. As observed in FIG. 2, the quality scores remained relatively invariant for a plurality of sequencing cycles using the dual-read sequencing methods as described herein. The accuracy of the sequencing is observed in FIG. 3.

Example 3. In Situ Dual Sequencing

The amplification and sequencing methods described herein may be applied to in situ sequencing applications. Typically, in situ sequencing consists of sequencing only one strand of a template polynucleotide in a cell as it is traditionally preferred to generate a template which is at least partially single-stranded and thus be available for hybridization to a sequencing primer. Using the amplification and sequencing methods described here, for example in Examples 1 and 2, the concatemeric forward and reverse amplicons that are created are longer as compared to conventional methods (e.g., the methods mentioned above). This enables greater reach because of the longer initial amplicons and allows for hybridization of free 3' ends not only to other immobilized primers, but also to a complementary region of other DNA amplicons. This enhances the amount of re-priming/hybridization events, which greatly enhances the amplification and sequencing efficiency compared to amplification with amplicons that contain only one copy of the initial nucleic acid molecule. Importantly, using an in situ amplification method which produces forward and reverse concatemers enables the amplicons to be configured within a localized cluster in a way that allows a sequencing primer to be hybridized directly to the amplicons without cleaving off the forward or the reverse amplicons. This permits sequencing of two distinct regions in situ, one at each end of the complementary strands of a target polynucleotide duplex, thereby doubling the sequencing throughput, allowing for very high accuracy results and sequencing depth.

In situ sequencing applications, an emerging area of genomics, where low amounts of target material can limit the ability of successful detection of the target molecules, may therefore benefit from the increased sequencing efficiency of the methods described herein. Methods for in situ spatial sequencing using, for example, padlock probes and other oligonucleotide primers to target cellular nucleic acids are known. Padlock probes are specialized ligation probes, see, for example, Nilsson M, et al. Science. 1994; 265 (5181):2085-2088, and have been applied to detect transcribed RNA in cells, see, for example, Christian A T, et al. Proc Natl Acad Sci USA. 2001; 98(25):14238-14243, both of which are incorporated herein by reference in their entireties. The oligonucleotide primer is similar to a padlock probe, however with an important distinction. Typically, both ends of a padlock probe hybridize to adjacent sequences and are then ligated together to form a circular oligonucleotide. Oligonucleotide primers hybridize to sequences adjacent to the target nucleic acid sequence resulting in a gap (e.g., a gap spanning the length of the target nucleic acid sequence). A polymerase then extends the first complementary region to generate a complement to the target nucleic acid sequence, and ligation circularizes the oligonucleotide primer. The circular oligonucleotide is then amplified and sequenced.

Figure 4A:
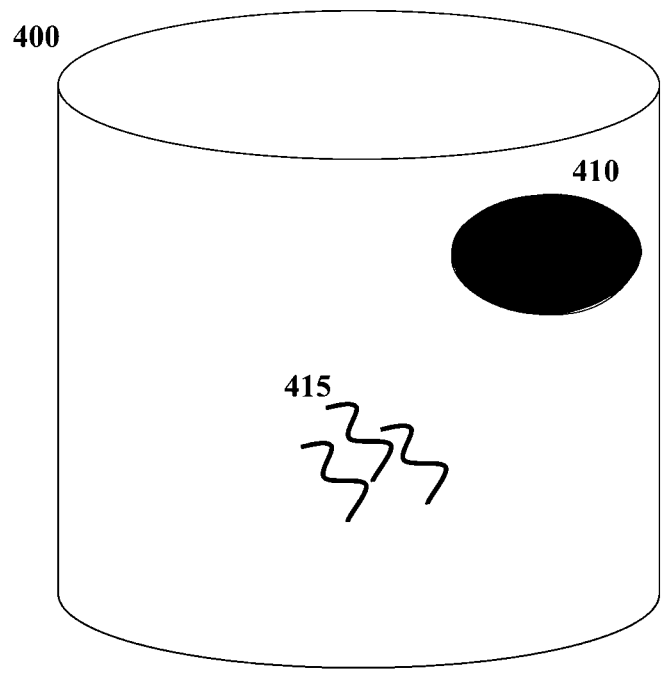
FIGS. 4A-4G. Cartoon illustration of an in situ sequencing method in according with some embodiments.
Figure 4B:
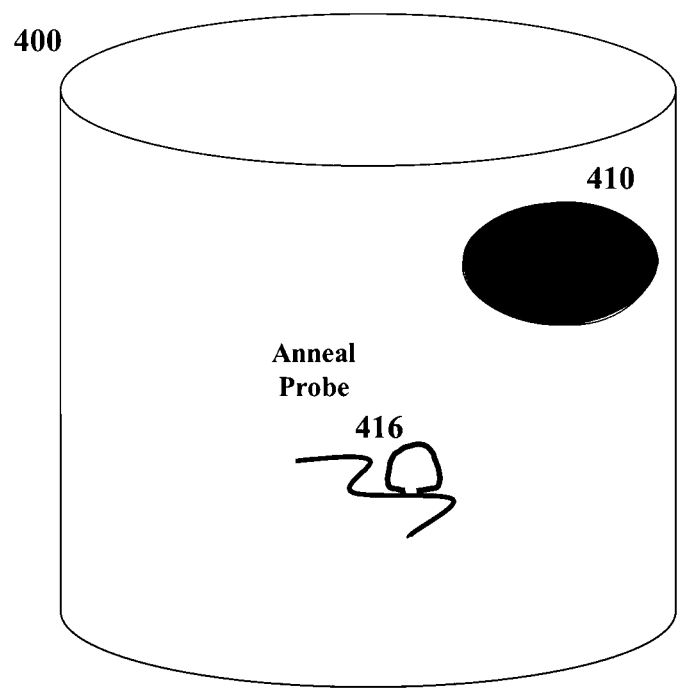
Figure 4C:
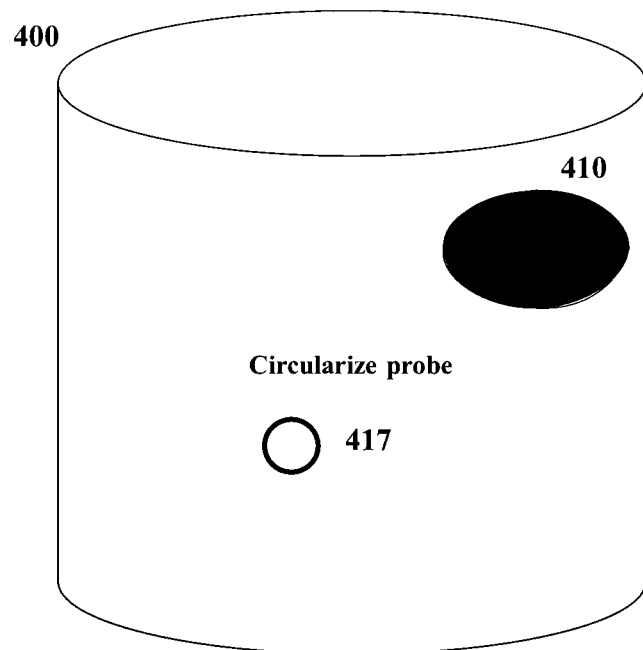
Figure 4D:
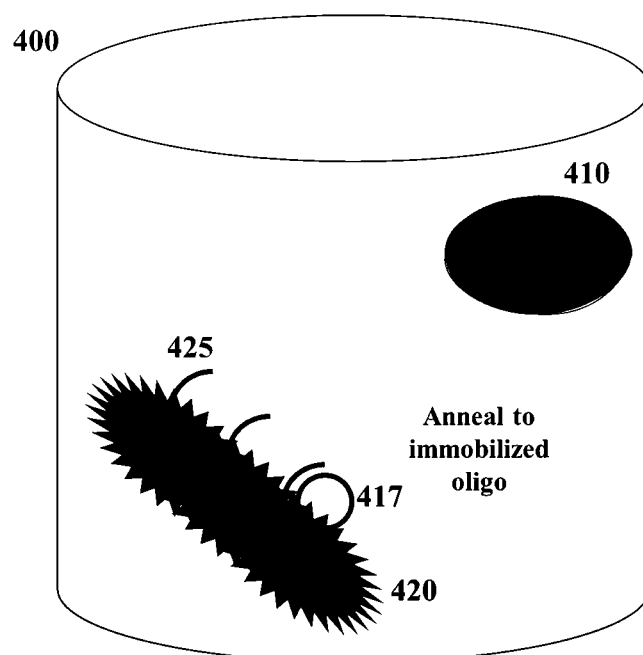
Figure 4E:
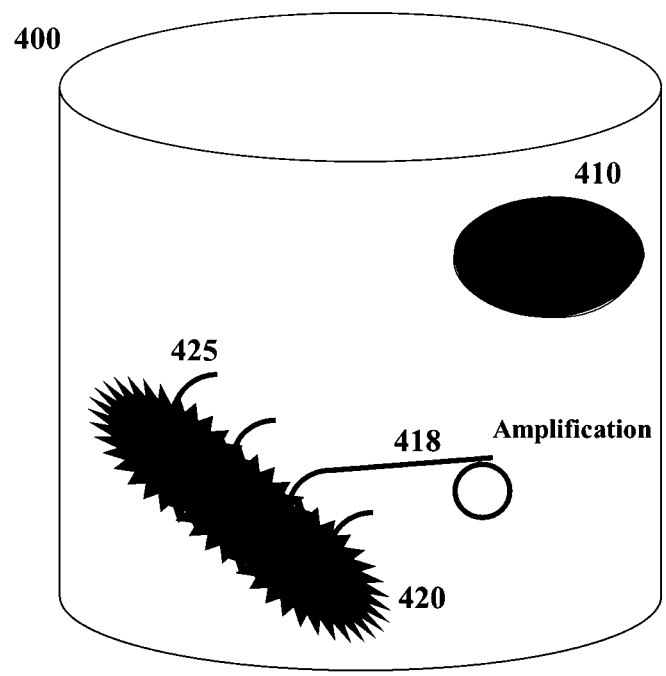
Figure 4F:
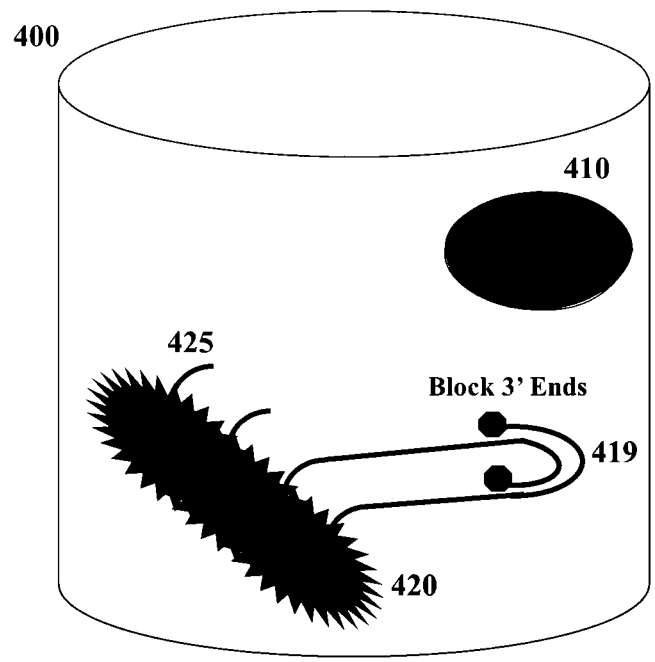
Figure 4G:
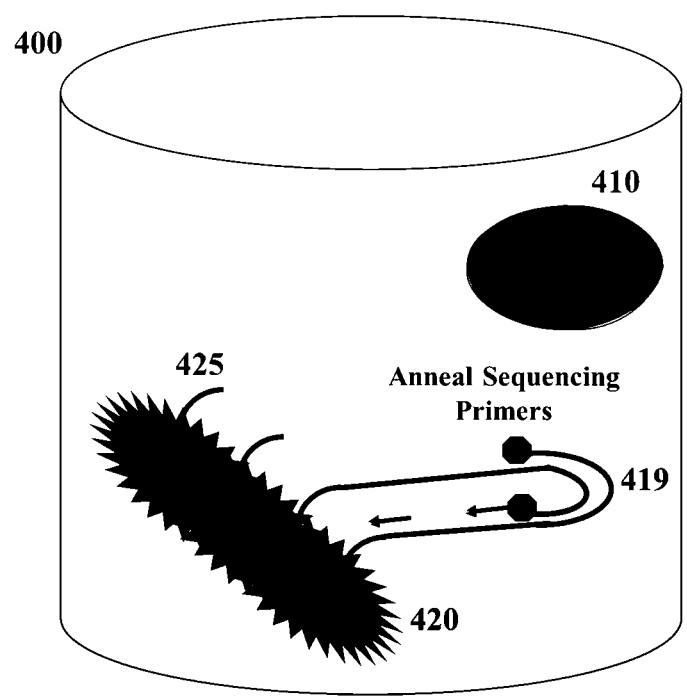

Briefly, cells and their surrounding milieu are attached to a substrate surface, fixed, and permeabilized (see, FIG. 4A). Oligonucleotide primers designed for recognition of a nucleic acid target of interest are then annealed to complementary regions which flank the nucleic acid of interest or a portion thereof (see, FIG. 4B). The oligonucleotide primer hybridizes to regions which flank the target nucleic acid sequence or a portion thereof, referred to as the first and the second complementary regions. In the presence of a polymerase (e.g., a non-strand displacing polymerase), the complement to the target sequence is generated by extending from the first complementary region and is ligated to the second complementary region to form a circularized oligonucleotide (see, FIG. 4C). The resulting circularized oligonucleotide is primed with an amplification primer and extended with a strand-displacing polymerase to generate a concatemer (see, FIGS. 4D-4F). This product is then primed and subjected to sequencing processes as described herein (see, FIG. 4G).

In embodiments, an exogenous polymer (e.g., a hydrogel) is added to the sample (e.g., a tissue) to provide a scaffold or matrix. Alternatively, in embodiments, the cell does not include an exogenous polymer. Optionally, one or more nucleotides within the amplification primer sequence, the sequencing primer sequence, and/or the immobilized oligonucleotide primer contains one or more functional moieties (e.g., bioconjugate reactive groups) that serve as attachment points to an exogenous matrix applied to the cell. In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein or the exogenous matrix). In embodiments, the complementary bioconjugate reactive groups within the cell to which the primers may be bound include one or more of lysines, cysteines, tyrosines, N- and C-termini of polypeptides, and serines. In embodiments, a plurality of oligonucleotide primers are provided to the matrix in which the cell is embedded prior to amplification. In embodiments, a plurality of oligonucleotide primers are provided to the matrix in which cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as aminoallyl deoxyuridine 5'-triphosphate (dUTP) nucleotide(s). In embodiments, the immobilized oligonucleotide primers may be used to aid in tethering the extension product to a confined area and may not be extended. In embodiments, the immobilized oligonucleotide primers may be used to aid in tethering the extension product to a confined area and may also be capable of being extended. For example, one or more immobilized oligonucleotides may be used to aid in tethering the extension product to a localized area and may be extended in an exponential RCA amplification reaction.

After the circular template molecules have undergone rolling circle amplification (e.g., exponential RCA or traditional RCA), a solvent exchange occurs to remove the strand-displacing polymerase. This is then followed by introduction of a second DNA polymerase for performing thermal bridge PCR (t-bPCR) or chemical bridge PCR (c-bPCR). In some embodiments, c-bPCR may be more favorable than t-bPCR for performing in situ amplification due to the smaller thermal variation window when cycling between denaturation and extension. For t-bPCR, a thermostable polymerase (e.g., Phusion) is introduced in a buffer containing dNTPs and additives (e.g., ethylene glycol). After an initial denaturation, the fixed cell including the amplified template polynucleotide is thermally cycled. After 10 to 45 thermal cycles, the polymerase is removed from the cell via another solvent exchange. In the case of c-bPCR, a solution containing a strand-displacement polymerase (for example, Bst LF or Bsu polymerase) is introduced to the rolling circle amplification products in the cell, followed by an incubation at 40° C.-65° C. for 0.5-2 min. This is followed by introducing a chemical denaturant, such as formamide or ethylene glycol, to the reaction vessel. After denaturation with the chemical denaturant, the cycle is reset by a wash step and flowing the strand-displacement polymerase over the cell. This cycle can be repeated 10 to 45 times in consecutive c-bPCR cycles.

The clusters can proceed to any necessary post-processing steps such as blocking of free 3' ends, removal of select amplicons, or hybridization of a sequencing primer. The clusters may be quantified by introducing a nucleic acid stain (e.g., SYBR® Gold stain available from Thermo Fisher, Catalog #S11494 or a FAM (6-fluorescein amidite) labeled oligonucleotide) in the presence of a buffer and allowed to incubate with the amplicons. After a wash, the cells containing the stained amplicons are imaged and subjected to post-processing analysis to determine cluster size and brightness. After these steps, clusters are ready for in situ sequencing in an in situ sequencing system.

These amplicons may be used for alternative sequencing technologies that have been described based on single molecule fluorescence in situ hybridization. These include MERFISH (Multiplexed Error-Robust Fluorescence In Situ Hybridization), STARmap (Spatially-resolved Transcript Amplicon Readout mapping), DART-FISH, seq-FISH (Sequential Fluorescence In Situ Hybridization), FISSEQ (fluorescent in situ sequencing), and others (see for example Chen, K. H., et al. (2015). Science, 348(6233), aaa6090; Wang, G., Moffitt, J. R. & Zhuang, X. Sci Rep. 2018; 8, 4847; Wang X. et al; Science, 2018; 27, Vol 361, Issue 6400, eaat5691; Cai, M. *Dissertation*, (2019) UC San Diego. ProQuest ID: Cai_ucsd_0033D_18822; Lee J H et al. Nat. Protoc. 2015; 10(3):442-58); and Sansone, A. Nat Methods 16, 458; 2019). Some of these techniques have been combined with super-resolution microscopy, expansion microscopy, or both, to increase the resolution and allow more transcripts to be resolved and thus counted.

In embodiments, sequencing includes encoding the sequencing read into a codeword. Useful encoding schemes include those developed for telecommunications, coding theory and information theory such as those set forth in Hamming, *Coding and Information Theory*, $2^{nd}$ Ed. Prentice Hall, Englewood Cliffs, N.J. (1986) and Moon T K. Error Correction Coding: Mathematical Methods and Algorithms. ed. 1st Wiley: 2005., each of which are incorporated herein by reference. A useful encoding scheme uses a Hamming code. A Hamming code can provide for signal (and therefore sequencing and barcode) distinction. In this scheme, signal states detected from a series of nucleotide incorporation and detection events (i.e., while sequencing the oligonucleotide barcode) can be represented as a series of the digits to form a codeword, the codeword having a length equivalent to the number incorporation/detection events. The digits can be binary (e.g. having a value of 1 for presence of signal and a value of 0 for absence of the signal) or digits can have a higher radix (e.g., a ternary digit having a value of 1 for fluorescence at a first wavelength, a value of 2 for fluorescence at a second wavelength, and a value of 0 for no fluorescence at those wavelengths, etc.). Barcode discrimination capabilities are provided when codewords can be quantified via Hamming distances between two codewords (i.e., barcode 1 having codeword 1, and barcode 2 having codeword 2, etc.). In embodiments, the barcodes in the known set of barcodes have a specified Hamming distance. In embodiments, the Hamming distance is 4 to 15. In embodiments, the Hamming distance is 8 to 12. In embodiments, the Hamming distance is 10. In embodiments, the Hamming distance is 0 to 100. In embodiments, the Hamming distance is 0 to 15. In embodiments, the Hamming distance is 0 to 10. In embodiments, the Hamming distance is 1 to 10. In embodiments, the Hamming distance is 5 to 10. In embodiments, the Hamming distance is 1 to 100.

Example 4. Invasion Strand-Assisted Dual Sequencing

In some embodiments, an invasion strand is generated to improve the accessibility of sequencing primers towards the partially double-stranded template polynucleotide by increasing the amount of ssDNA available for primer hybridization. Methods for generation of invasion strands for sequencing two strands are discussed briefly herein. In embodiments, methods disclosed herein utilize strand invasion using invasion primers into partially dsDNA amplicons bound to a solid phase or immobilized to a cellular component or a matrix within the cell, followed by polymerase extension of the invasion primers. Strand invasion into dsDNA can be challenging in general but can be particularly challenging in dense monoclonal clusters of dsDNA where DNA molecules are packed tightly together in a spatially localized fashion on a solid phase or in a cell. Because the local concentration of partially double-stranded concatemers is very high, insertion of a traditional primer oligonucleotide is thermodynamically unfavorable.

The invasion primers are oligonucleotide sequences that bind to one strand of the partially dsDNA molecule in the cluster. For example, the invasion primer may bind to a portion of the common adapter sequence of only the forward, or only the reverse amplicons in clusters. These invasion oligonucleotides may include nucleic acids having a binding affinity higher than the binding affinity of standard or canonical DNA oligonucleotides, such as locked nucleic acids (LNA), peptide nucleic acids (PNAs), 2'-O-methyl RNA:DNA chimeras, minor groove binder probes (MGB), or morpholino probes. The invasion primers are introduced into a flow cell that contains monoclonal partially dsDNA clusters generated using an amplification method described herein. Some of these invasion primers can undergo spontaneous strand invasion into partially dsDNA, as is the case for example for PNA invasion primers under low ionic strength conditions, while other invasion primers may need assistance of additives such as DMSO, ethylene glycol, formamide, betaine, or other denaturants that assist strand invasion by inducing more breathability within partially dsDNA amplicons. For example, such additives may include a buffered solution containing about 0 to about 50% DMSO, about 0 to about 50% ethylene glycol, about 0 to about 20% formamide, or about 0 to about 3M betaine. In order to achieve sufficient "breathability" within partially dsDNA amplicons that are bound to a solid phase, it is helpful to include additives that can assist the "fraying" of the partially dsDNA molecules, particularly at the 5' and 3' ends.

The invasion oligonucleotide can be introduced without a polymerase and allowed to invade and anneal to the complementary region, or it may be introduced together with a polymerase for runoff extension. Examples of polymerases that can be used for runoff extension are strand-displacing polymerases such as Bst large fragment, Bst2.0 (New England Biolabs), Bsm DNA polymerase, Bsu polymerase, SD polymerase, Vent exo-polymerase or Phi29 polymerase. In certain experiments, it is preferable to introduce the invasion oligonucleotide (e.g., a 15-75 bp invasion primer) together with a polymerase in the same reaction mixture. Because of the close physical proximity of the forward and reverse strands of the partially dsDNA molecules within a cluster, the hybridization of the invasion oligo to one of the DNA strands is often transient, and can be outcompeted easily by the reannealing of the forward and reverse strands of the partially dsDNA molecules. To efficiently extend the invasion oligos that transiently hybridize, it is useful to have the polymerase within the same reaction mixture such that the polymerase can immediately extend the invasion oligo during the transient hybridizations that occur.

The initiation point for the first sequencing reaction is provided by annealing a sequencing primer complementary to a region within one of the strands. In the presence of an enzyme (e.g., a DNA polymerase), nucleotides (e.g., labeled nucleotides) are incorporated and detected such that the identity of the incorporated nucleotides allows for the identification of the first strand. Thus, the first sequencing reaction may include hybridizing a sequencing primer to a region of an amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand. Note, the second sequenced strand is present while sequencing the first strand, albeit the second strand is hybridized to the invasion strand.

P—Embodiments

The present disclosure provides the following illustrative embodiments.

Embodiment P1. A method of sequencing a template polynucleotide, the method comprising: (A) generating a partially double-stranded amplification product comprising a first strand hybridized to a second strand, wherein (i) the partially double-stranded amplification product comprises multiple copies of the template polynucleotide, and (ii) the first strand and second strand are both covalently attached to a solid surface; (B) generating a first sequencing read by hybridizing one or more first sequencing primers to a single-stranded portion of the first strand, and extending the one or more first sequencing primers; and (C) generating a second sequencing read by hybridizing one or more second sequencing primers to the second strand, and extending the one or more second sequencing primers.

Embodiment P2. The method of embodiment P1, wherein neither the first strand nor the second strand is cleaved before generating the first sequencing read.

Embodiment P3. The method of embodiment P1 or P2, wherein the first strand is not cleaved after generating the first sequencing read.

Embodiment P4. The method of embodiment P1 or P2, wherein the first strand is cleaved after generating the first sequencing read but before generating the second sequencing read.

Embodiment P5. The method of any one of embodiment P1 to embodiment P4, wherein the method does not comprise an amplification step between generating the first sequencing read and generating the second sequencing read.

Embodiment P6. The method of any one of embodiment P1 to embodiment P5, wherein the partially double-stranded amplification product comprises three or more copies of the template polynucleotide.

Embodiment P7. The method of any one of embodiment P1 to embodiment P6, wherein (i) generating the first sequencing read comprises extending two or more first sequencing primers hybridized to the first strand, and/or (ii) generating the second sequencing read comprises extending two or more second sequencing primers hybridized to the second strand.

Embodiment P8. The method of any one of embodiment P1 to embodiment P7, wherein the template polynucleotide comprises primer binding sequences that are complementary to one or more substrate-bound primers.

Embodiment P9. The method of any one of embodiment P1 to embodiment P8, wherein generating the partially double-stranded amplification product comprises exponential rolling circle amplification (eRCA), loop-mediated isothermal amplification (LAMP), or multiple displacement amplification (MDA).

Embodiment P10. The method of embodiment P9, wherein generating the partially double-stranded amplification product comprises exponential rolling circle amplification (eRCA).

Embodiment P11. The method of embodiment P9, wherein generating the partially double-stranded amplification product comprises loop-mediated isothermal amplification (LAMP).

Embodiment P12. The method of embodiment P9, wherein generating the partially double-stranded amplification product comprises multiple displacement amplification (MDA).

Embodiment P13. The method of any one of embodiment P1 to embodiment P8, wherein generating the partially double-stranded amplification product comprises: (a) amplifying the template polynucleotide to produce a first amplicon comprising multiple complements of the template polynucleotide; and (b) extending a reverse primer hybridized to the first amplicon to produce a double-stranded amplicon comprising multiple copies of the template polynucleotide.

Embodiment P14. The method of embodiment P13, wherein step (a) is performed in solution and then the first amplicon is hybridized to a solid support, wherein the solid support contains a plurality of substrate-bound primers.

Embodiment P15. The method of embodiment P13, wherein both step (a) and step (b) are performed on a solid support, wherein the solid support contains a plurality of substrate-bound primers.

Embodiment P16. The method of any one of embodiment P14 to embodiment P15, wherein at least some of the substrate-bound primers are phosphorothioated primers.

Embodiment P17. The method of any one of embodiment P9 to embodiment P16, wherein the template polynucleotide is single-stranded DNA, double-stranded DNA, single-stranded RNA, or double-stranded RNA.

Embodiment P18. The method of any one of embodiment P1 to embodiment P8, wherein generating the partially double-stranded amplification product comprises: (a) amplifying the template polynucleotide by extending an amplification primer with a strand-displacing polymerase, wherein the template polynucleotide comprises a continuous strand lacking free 5' and 3' ends, and wherein the primer extension generates a first extension product comprising multiple complements of the template polynucleotide; (b) amplifying the first extension product or a complement thereof with a plurality of primers attached to the solid surface, wherein the plurality of primers comprise a plurality of forward primers with complementarity to the first extension product and a plurality of reverse primers with complementarity to a complement of the first extension product, and the amplifying comprises a plurality of cycles of strand denaturation, primer hybridization, and primer extension.

Embodiment P19. The method of embodiment P18, wherein the first extension product comprises at least one cleavable site.

Embodiment P20. The method of embodiment P19, wherein the at least one cleavable site comprises deoxyuracil triphosphate (dUTP).

Embodiment P21. The method of embodiment P19 or P20, wherein the first extension product is cleaved at the at least one cleavable site prior to step (b).

Embodiment P22. The method of embodiment P18, wherein step (b) comprises (i) extension of a 3' end of a first substrate-bound primer extension product hybridized to a second substrate-bound primer, and/or (ii) extension of a 3' end of a third substrate-bound primer extension product hybridized to itself.

Embodiment P23. The method of any one of embodiment P18 to embodiment P22, wherein the amplification primer is attached to the solid surface.

Embodiment P24. The method of any one of embodiment P18 to embodiment P22, wherein the amplification primer is in solution.

Embodiment P25. The method of any one of embodiment P18 to embodiment P24, wherein the template polynucleotide comprises single-stranded circular DNA.

Embodiment P26. The method of any one of embodiment P18 to embodiment P24, wherein the template polynucleotide comprises double-stranded DNA.

Embodiment P27. The method of any one of embodiment P18 to embodiment P24, wherein the template polynucleotide comprises single stranded RNA.

Embodiment P28. The method of any one of embodiment P18 to embodiment P24, wherein the template polynucleotide comprises double stranded RNA.

Embodiment P29. The method of any one of embodiment P18 to embodiment P22, further comprising forming the template polynucleotide by ligating ends of a linear polynucleotide together.

Embodiment P30. The method of any one of embodiment P18 to embodiment P22, further comprising forming the template polynucleotide by ligating a hairpin adapter to an end of a linear polynucleotide.

Embodiment P31. The method of embodiment P30, wherein forming the template polynucleotide comprises ligating hairpin adapters to both ends of the linear polynucleotide.

Embodiment P32. The method of any one of embodiment P18 to embodiment P31, wherein step (a) comprises exponential rolling circle amplification (eRCA).

Embodiment P33. The method of any one of embodiment P18 to embodiment P31, wherein step (a) comprises hyper-branched rolling circle amplification (HRCA).

Embodiment P34. The method of any one of embodiment P18 to embodiment P33, wherein the amplification primer comprises one or more phosphorothioate nucleotides.

Embodiment P35. The method of any one of embodiments P18 to embodiment P34, wherein the step of extending the amplification primer comprises incubation with the strand-displacing polymerase (i) for about 10 seconds to about 30 minutes, and/or (ii) at a temperature of about 20° C. to about 50° C.

Embodiment P36. The method of embodiment P35, wherein incubation with the strand-displacing polymerase is for about 0.5 minutes to about 16 minutes.

Embodiment P37. The method of embodiment P35, wherein incubation with the strand-displacing polymerase is for about 0.5 minutes to about 10 minutes.

Embodiment P38. The method of embodiment P35, wherein incubation with the strand-displacing polymerase is for about 1 minutes to about 5 minutes.

Embodiment P39. The method of any one of embodiment P35 to embodiment P38, wherein incubation with the strand-displacing polymerase is at a temperature of about 35° C. to 42° C.

Embodiment P40. The method of any one of embodiment P35 to embodiment P38, wherein incubation with the strand-displacing polymerase is at a temperature of about 37° C. to 40° C.

Embodiment P41. The method of any one of embodiment P18 to embodiment P40, wherein the strand-displacing polymerase is phi29 polymerase, phi29 mutant polymerase or a thermostable phi29 mutant polymerase.

Embodiment P42. The method of any one of embodiment P18 to embodiment P41, wherein the strand-displacing polymerase is removed or inactivated prior to step (b).

Embodiment P43. The method of any of embodiment P18 to embodiment P42, wherein step (b) comprises addition of a second polymerase.

Embodiment P44. The method of any one of embodiment P18 to embodiment P43, wherein step (b) comprises thermal bridge polymerase chain reaction amplification.

Embodiment P45. The method of embodiment P44, wherein step (b) comprises incubation in an additive that lowers a DNA denaturation temperature.

Embodiment P46. The method of embodiment P45, wherein the additive is betaine, dimethyl sulfoxide (DMSO), ethylene glycol, formamide, glycerol, guanidine thiocyanate, 4-methylmorpholine 4-oxide (NMO), or a mixture thereof.

Embodiment P47. The method of any one of embodiment P18 to embodiment P46, wherein the plurality of cycles is about 10 to about 45 cycles.

Embodiment P48. The method of any one of embodiment P18 to embodiment P47, wherein the plurality of cycles is about 20 to about 30 cycles.

Embodiment P49. The method of any one of embodiment P18 to embodiment P48, wherein step (b) comprising an initial denaturation at about 85° C.-95° C. for about 1 minutes to about 10 minutes.

Embodiment P50. The method of any one of embodiment P18 to embodiment P49, wherein step (b) comprising an initial denaturation at about 85° C.-95° C. for about 5 minutes to about 10 minutes.

Embodiment P51. The method of any one of embodiment P18 to embodiment P50, wherein the plurality of cycles comprises thermally cycling between (i) about 85° C. for about 15-30 sec for denaturation, and (ii) about 65° C. for about 1 minute for annealing/extension of the primer.

Embodiment P52. The method of any one of embodiment P18 to embodiment P51, wherein the plurality of cycles comprises thermally cycling between (i) about 85° C. for about 15-30 sec for denaturation, and (ii) about 65° C. for about 30 seconds for annealing/extension of the primer.

Embodiment P53. The method of any one of embodiment P18 to embodiment P52, wherein the plurality of cycles comprises thermally cycling between (i) about 85° C.-95° C. for about 15-30 sec for denaturation, and (ii) about 65° C. for about 30 seconds for annealing/extension of the primer.

Embodiment P54. The method of any one of embodiment P18 to embodiment P53, wherein step (b) comprises denaturation using a chemical denaturant.

Embodiment P55. The method of any one of embodiment P18 to embodiment P54, wherein step (b) comprises denaturation using acetic acid, hydrochloric acid, nitric acid, formamide, guanidine, sodium salicylate, sodium hydroxide, dimethyl sulfoxide (DMSO), propylene glycol, urea, or a mixture thereof.

Embodiment P56. The method of any one of embodiment P18 to embodiment P55, wherein the template polynucleotide of step (a) is a circular polynucleotide that is about 100 to about 1000 nucleotides in length, about 100 to about 300 nucleotides in length, about 300 to about 500 nucleotides in length, or about 500 to about 1000 nucleotides in length.

Embodiment P57. The method of embodiment P56, wherein the circular polynucleotide is about 300 to about 600 nucleotides in length.

Embodiment P58. The method of embodiment P56 or P57, wherein the circular polynucleotide includes at least one cleavable site.

Embodiment P59. A complex comprising: (a) a partially double-stranded amplification product comprising a first strand hybridized to a second strand, wherein (i) the partially double-stranded amplification product comprises multiple copies of a template polynucleotide, and (ii) the first strand and second strand are both covalently attached to a solid surface; and (b) one or more first sequencing primer extension products hybridized to a single-stranded portion of the first strand, wherein the sequencing primer extension product comprises a labeled nucleotide; and (c) one or more polymerases.

Embodiment P60. The complex of embodiment P59, wherein the template polynucleotide of (a) is a circular polynucleotide that is about 100 to about 1000 nucleotides in length, about 100 to about 300 nucleotides in length, about 300 to about 500 nucleotides in length, or about 500 to about 1000 nucleotides in length.

Embodiment P61. The complex of embodiment P59 or P60, wherein the template polynucleotide comprises one or more adapters.

Embodiment P62. The complex of embodiment P61, wherein the one or more adapters comprise a hairpin loop structure.

Embodiment P63. The complex of any one of embodiment P59 to embodiment P62, wherein the label is a fluorescent label.

Additional Embodiments

The present disclosure provides the following additional illustrative embodiments.

Embodiment 1. A method of sequencing a template polynucleotide, the method comprising: (A) generating a partially double-stranded amplification product comprising a first strand hybridized to a second strand, wherein (i) the partially double-stranded amplification product comprises multiple copies of the template polynucleotide, and (ii) the first strand and second strand are both covalently attached to a solid surface; (B) generating a first sequencing read by hybridizing one or more first sequencing primers to a single-stranded portion of the first strand, and extending the one or more first sequencing primers; and (C) generating a second sequencing read by hybridizing one or more second sequencing primers to the second strand, and extending the one or more second sequencing primers.

Embodiment 2. A method of sequencing a template polynucleotide in situ, the method comprising: (A) generating a partially double-stranded amplification product in a cell comprising a first strand hybridized to a second strand, wherein (i) the partially double-stranded amplification product comprises multiple copies of the template polynucleotide, and (ii) the first strand and second strand are both immobilized to a cellular component or a matrix within the cell; (B) generating a first sequencing read by hybridizing one or more first sequencing primers to a single-stranded portion of the first strand, and extending the one or more first sequencing primers; and (C) generating a second sequencing read by hybridizing one or more second sequencing primers to the second strand, and extending the one or more second sequencing primers.

Embodiment 3. The method of embodiment 1 or embodiment 2, wherein the partially double-stranded amplification product is a concatemer.

Embodiment 4. The method of any one of embodiment 1-3, wherein neither the first strand nor the second strand is cleaved before generating the first sequencing read.

Embodiment 5. The method of any one of embodiment 1-3, wherein the first strand is not cleaved after generating the first sequencing read.

Embodiment 6. The method of any one of embodiment 1-3, wherein the first strand is cleaved after generating the first sequencing read but before generating the second sequencing read.

Embodiment 7. The method of any one of embodiment 1-6, wherein the method does not comprise an amplification step between generating the first sequencing read and generating the second sequencing read.

Embodiment 8. The method of any one of embodiment 1-7, wherein the partially double-stranded amplification product comprises three or more copies of the template polynucleotide.

Embodiment 9. The method of any one of embodiment 1-8, wherein (i) generating the first sequencing read comprises extending two or more first sequencing primers hybridized to the first strand, and/or (ii) generating the second sequencing read comprises extending two or more second sequencing primers hybridized to the second strand.

Embodiment 10. The method of any one of embodiment 1-9, wherein the template polynucleotide comprises primer binding sequences that are complementary to one or more substrate-bound primers.

Embodiment 11. The method of any one of embodiment 1-10, wherein generating the partially double-stranded amplification product comprises exponential rolling circle amplification (eRCA), hyperbranched rolling circle amplification (HRCA), loop-mediated isothermal amplification (LAMP), or multiple displacement amplification (MDA).

Embodiment 12. The method of any one of embodiment 1-11, wherein generating the partially double-stranded amplification product comprises exponential rolling circle amplification (eRCA).

Embodiment 13. The method of any one of embodiment 1-11, wherein generating the partially double-stranded amplification product comprises hyperbranched rolling circle amplification (eRCA).

Embodiment 14. The method of any one of embodiment 1-11, wherein generating the partially double-stranded amplification product comprises loop-mediated isothermal amplification (LAMP).

Embodiment 15. The method of any one of embodiment 1-11, wherein generating the partially double-stranded amplification product comprises multiple displacement amplification (MDA).

Embodiment 16. The method of any one of embodiment 1 or 3-15, wherein generating the partially double-stranded amplification product comprises: (a) amplifying the template polynucleotide to produce a first amplicon comprising multiple complements of the template polynucleotide; and (b) extending a reverse primer hybridized to the first amplicon to produce a double-stranded amplicon comprising multiple copies of the template polynucleotide.

Embodiment 17. The method of embodiment 16, wherein step (a) is performed in solution and then the first amplicon is hybridized to a solid support, wherein the solid support contains a plurality of substrate-bound primers.

Embodiment 18. The method of embodiment 16, wherein both step (a) and step (b) are performed on a solid support, wherein the solid support contains a plurality of substrate-bound primers.

Embodiment 19. The method of any one of embodiment 2-18, wherein generating the partially double-stranded amplification product comprises: (a) amplifying the template polynucleotide to produce a first amplicon comprising multiple complements of the template polynucleotide; and (b) extending a reverse primer hybridized to the first amplicon to produce a double-stranded amplicon comprising multiple copies of the template polynucleotide.

Embodiment 20. The method of embodiment 19, wherein step (a) is performed in solution and then the first amplicon is hybridized to a matrix in a cell, wherein the matrix contains a plurality of immobilized primers.

Embodiment 21. The method of embodiment 19, wherein both step (a) and step (b) are performed on a matrix in a cell, wherein the matrix contains a plurality of substrate-bound primers.

Embodiment 22. The method of embodiment 17 or embodiment 18, wherein at least some of the substrate-bound primers are phosphorothioated primers.

Embodiment 23. The method of embodiment 20 or embodiment 21, wherein at least some of the immobilized primers are phosphorothioated primers.

Embodiment 24. The method of any one of embodiment 1-23, wherein the template polynucleotide is single-stranded DNA, double-stranded DNA, single-stranded RNA, or double-stranded RNA.

Embodiment 25. The method of any one of embodiment 1, 3-18, 22, or 24, wherein generating the partially double-stranded amplification product comprises: (a) amplifying the template polynucleotide by extending an amplification primer with a strand-displacing polymerase, wherein the template polynucleotide comprises a continuous strand lacking free 5' and 3' ends, and wherein the primer extension generates a first extension product comprising multiple complements of the template polynucleotide; and (b) amplifying the first extension product or a complement thereof with a plurality of primers attached to the solid surface, wherein the plurality of primers comprise a plurality of forward primers with complementarity to the first extension product and a plurality of reverse primers with complementarity to a complement of the first extension product, and the amplifying comprises a plurality of cycles of strand denaturation, primer hybridization, and primer extension.

Embodiment 26. The method of any one of embodiment 2-15, 19-21, or 23-24, wherein generating the partially double-stranded amplification product in situ comprises: (a) amplifying the template polynucleotide by extending an immobilized amplification primer with a strand-displacing polymerase, wherein the template polynucleotide comprises a continuous strand lacking free 5' and 3' ends, and wherein the primer extension generates a first extension product comprising multiple complements of the template polynucleotide; (b) amplifying the first extension product or a complement thereof with a plurality of immobilized primers in the cell, wherein the plurality of immobilized primers comprise a plurality of forward primers with complementarity to the first extension product and a plurality of reverse primers with complementarity to a complement of the first extension product, and the amplifying comprises a plurality of cycles of strand denaturation, primer hybridization, and primer extension.

Embodiment 27. The method of embodiment 25 or embodiment 26, wherein the first extension product comprises at least one cleavable site.

Embodiment 28. The method of any one of embodiment 25-27, wherein the at least one cleavable site comprises deoxyuracil triphosphate (dUTP).

Embodiment 29. The method of any one of embodiment 25-28, wherein the first extension product is cleaved at the at least one cleavable site prior to step (b).

Embodiment 30. The method of any one of embodiment 25-29, wherein step (b) comprises (i) extension of a 3' end of a first substrate-bound primer extension product hybridized to a second substrate-bound primer, and/or (ii) extension of a 3' end of a third substrate-bound primer extension product hybridized to itself.

Embodiment 31. The method of any one of embodiment 26-29, wherein step (b) comprises (i) extension of a 3' end of a first immobilized primer extension product hybridized to a second immobilized primer, and/or (ii) extension of a 3' end of a third immobilized primer extension product hybridized to itself in a cell.

Embodiment 32. The method of any one of embodiment 25-30, wherein the amplification primer is attached to the solid surface.

Embodiment 33. The method of any one of embodiment 26-29 or 31, wherein the immobilized amplification primer is attached to the cell.

Embodiment 34. The method of any one of embodiment 25-33, wherein the amplification primer is in solution.

Embodiment 35. The method of any one of embodiment 25-33, wherein the template polynucleotide comprises single-stranded circular DNA.

Embodiment 36. The method of any one of embodiment 25-33, wherein the template polynucleotide comprises double-stranded DNA.

Embodiment 37. The method of any one of embodiment 25-33, wherein the template polynucleotide comprises single-stranded RNA.

Embodiment 38. The method of any one of embodiment 25-33, wherein the template polynucleotide comprises double-stranded RNA.

Embodiment 39. The method of any one of embodiment 25-38, further comprising forming the template polynucleotide by ligating ends of a linear polynucleotide together.

Embodiment 40. The method of any one of embodiment 25-38, further comprising forming the template polynucleotide by ligating a hairpin adapter to an end of a linear polynucleotide.

Embodiment 41. The method of embodiment 40, wherein forming the template polynucleotide comprises ligating hairpin adapters to both ends of the linear polynucleotide.

Embodiment 42. The method of any one of embodiment 25-41, wherein step (a) comprises exponential rolling circle amplification (eRCA).

Embodiment 43. The method of any one of embodiment 25-41, wherein step (a) comprises hyberbranched rolling circle amplification (HRCA).

Embodiment 44. The method of any one of embodiment 25-43, wherein the amplification primer comprises one or more phosphorothioate nucleotides.

Embodiment 45. The method of any one of embodiment 25-44, wherein the step of extending the amplification primer comprises incubation with the strand-displacing polymerase (i) for about 10 seconds to about 30 minutes, and/or (ii) at a temperature of about 20° C. to about 50° C.

Embodiment 46. The method of any one of embodiment 25-45, wherein incubation with the strand-displacing polymerase is for about 0.5 minutes to about 16 minutes.

Embodiment 47. The method of any one of embodiment 25-45, wherein incubation with the strand-displacing polymerase is for about 0.5 minutes to about 10 minutes.

Embodiment 48. The method of any one of embodiment 25-45, wherein incubation with the strand-displacing polymerase is for about 1 minutes to about 5 minutes.

Embodiment 49. The method of any one of embodiment 23-45, wherein incubation with the strand-displacing polymerase is at a temperature of about 35° C. to 42° C.

Embodiment 50. The method of any one of embodiment 25-45, wherein incubation with the strand-displacing polymerase is at a temperature of about 37° C. to 40° C.

Embodiment 51. The method of any one of embodiment 25-50, wherein the strand-displacing polymerase is phi29 polymerase, phi29 mutant polymerase or a thermostable phi29 mutant polymerase.

Embodiment 52. The method of any one of embodiment 25-51, wherein prior to step (a) the strand-displacing polymerase contacts the amplification primer and template polynucleotide in the absence of dNTPs; and optionally, excess strand-displacing polymerase is removed.

Embodiment 53. The method of embodiment 52, further comprising contacting the template polynucleotide with a plurality of dNTPs under conditions suitable for amplification.

Embodiment 54. The method of any one of embodiment 25-53, wherein the strand-displacing polymerase is removed or inactivated prior to step (b).

Embodiment 55. The method of any one of embodiment 25-54, wherein step (b) comprises addition of a second polymerase.

Embodiment 56. The method of any one of embodiment 25-55, wherein step (b) comprises thermal bridge polymerase chain reaction amplification.

Embodiment 57. The method of any one of embodiment 25-56, wherein step (b) comprises incubation in an additive that lowers a DNA denaturation temperature.

Embodiment 58. The method of embodiment 57, wherein the additive is betaine, dimethyl sulfoxide (DMSO), ethylene glycol, formamide, glycerol, guanidine thiocyanate, 4-methylmorpholine 4-oxide (NMO), or a mixture thereof.

Embodiment 59. The method of any one of embodiment 25-58, wherein the plurality of cycles is about 10 to about 45 cycles.

Embodiment 60. The method of any one of embodiment 25-58, wherein the plurality of cycles is about 20 to about 30 cycles.

Embodiment 61. The method of any one of embodiment 25-60, wherein step (b) comprises an initial denaturation at about 85° C.-95° C. for about 1 minutes to about 10 minutes.

Embodiment 62. The method of any one of embodiment 25-60, wherein step (b) comprises an initial denaturation at about 85° C.-95° C. for about 5 minutes to about 10 minutes.

Embodiment 63. The method of any one of embodiment 25-62, wherein the plurality of cycles comprises thermally cycling between (i) about 85° C. for about 15-30 sec for denaturation, and (ii) about 65° C. for about 1 minute for annealing/extension of the primer.

Embodiment 64. The method of any one of embodiment 25-62, wherein the plurality of cycles comprises thermally cycling between (i) about 85° C. for about 15-30 sec for denaturation, and (ii) about 65° C. for about 30 seconds for annealing/extension of the primer.

Embodiment 65. The method of any one of embodiment 25-62, wherein the plurality of cycles comprises thermally cycling between (i) about 85° C.-95° C. for about 15-30 sec for denaturation, and (ii) about 65° C. for about 30 seconds for annealing/extension of the primer.

Embodiment 66. The method of any one of embodiment 25-65, wherein step (b) comprises denaturation using a chemical denaturant.

Embodiment 67. The method of any one of embodiment 25-66, wherein amplifying the first extension product comprises a plurality of fluidic cycles of strand denaturation using a chemical denaturant, and a plurality of fluidic cycles of primer extension comprising an extension mixture.

Embodiment 68. The method of embodiment 67, wherein step (b) comprises thermally cycling between about 40° C. to about 65° C. during the plurality of fluidic cycles.

Embodiment 69. The method of any one of embodiment 25-68, wherein step (b) comprises denaturation using acetic acid, hydrochloric acid, nitric acid, formamide, guanidine, sodium salicylate, sodium hydroxide, dimethyl sulfoxide (DMSO), propylene glycol, urea, or a mixture thereof.

Embodiment 70. The method of any one of embodiment 25-69, wherein the template polynucleotide of step (a) is a circular polynucleotide that is about 100 to about 1000 nucleotides in length, about 100 to about 300 nucleotides in length, about 300 to about 500 nucleotides in length, or about 500 to about 1000 nucleotides in length.

Embodiment 71. The method of embodiment 70, wherein the circular polynucleotide is about 300 to about 600 nucleotides in length.

Embodiment 72. The method of embodiment 70 or embodiment 71, wherein the circular polynucleotide includes at least one cleavable site.

Embodiment 73. The method of any one of embodiment 25, 27-30, or 34-72, wherein a first invasion strand is generated by hybridizing an invasion primer to the second strand of the partially double-stranded amplification product, and extending the invasion primer, wherein the invasion primer is not covalently attached to the solid support; and generating a first sequencing read by hybridizing one or more sequencing primers to the first strand, and extending the one or more first sequencing primers.

Embodiment 74. The method of any one of embodiment 26 or 31-72, wherein a first invasion strand is generated by hybridizing an invasion primer to the second strand of the partially double-stranded amplification product, and extending the invasion primer, wherein the invasion primer is not immobilized to a cellular component or a matrix within the cell; and generating a first sequencing read by hybridizing one or more sequencing primers to the first strand, and extending the one or more first sequencing primers.

Embodiment 75. The method of embodiment 73, further comprising removing the first invasion strand; generating a second invasion strand hybridized to the first strand by hybridizing a second invasion primer to the first strand, and extending the second invasion primer, wherein the second invasion primer is not covalently attached to the solid support; and generating a second sequencing read by hybridizing one or more second sequencing primers to the second strand, and extending the one or more second sequencing primers.

Embodiment 76. The method of embodiment 74, further comprising removing the first invasion strand; generating a second invasion strand hybridized to the first strand by hybridizing a second invasion primer to the first strand, and extending the second invasion primer, wherein the second invasion primer is not immobilized to a cellular component or a matrix within the cell; and generating a second sequencing read by hybridizing one or more second sequencing primers to the second strand, and extending the one or more second sequencing primers.

Embodiment 77. The method of any one of embodiment 73-76, wherein the invasion primer comprises a cleavable site.

Embodiment 78. The method of embodiment 77, wherein the cleavable site is located at the 3' end of the invasion primer.

Embodiment 79. The method of embodiment 77 or embodiment 78, further comprising cleaving the cleavable site in the invasion primer to generate a free 3' end within the invasion primer, removing the invasion strand, and generating a second sequencing read by extending the invasion primer.

Embodiment 80. The method of any one of embodiment 73-79, further comprising removing the first strand by cleaving the first strand at a cleavable site and generating a second sequencing read by hybridizing one or more second sequencing primers to the second strand; and extending the one or more second sequencing primers.

Embodiment 81. A complex comprising: (a) a partially double-stranded amplification product comprising a first strand hybridized to a second strand, wherein (i) the partially double-stranded amplification product comprises multiple copies of a template polynucleotide, and (ii) the first strand and second strand are both covalently attached to a solid surface; and (b) one or more first sequencing primer extension products hybridized to a single-stranded portion of the first strand, wherein the sequencing primer extension product comprises a labeled nucleotide; and (c) one or more polymerases.

Embodiment 82. A complex comprising: (a) a partially double-stranded amplification product comprising a first strand hybridized to a second strand, wherein (i) the partially double-stranded amplification product comprises multiple copies of a template polynucleotide, and (ii) the first strand and second strand are both immobilized to a cellular component or a matrix within the cell; and (b) one or more first sequencing primer extension products hybridized to a single-stranded portion of the first strand, wherein the sequencing primer extension product comprises a labeled nucleotide; and (c) one or more polymerases.

Embodiment 83. The complex of embodiment 81 or embodiment 82, wherein the template polynucleotide of (a) is a circular polynucleotide that is about 100 to about 1000 nucleotides in length, about 100 to about 300 nucleotides in length, about 300 to about 500 nucleotides in length, or about 500 to about 1000 nucleotides in length.

Embodiment 84. The complex of any one of embodiment 81-83, wherein the template polynucleotide comprises one or more adapters.

Embodiment 85. The complex of embodiment 84, wherein the one or more adapters comprise a hairpin loop structure.

Embodiment 86. The complex of any one of embodiment 81-85, wherein the label is a fluorescent label.

What is claimed is:

1. A method of sequencing a circular template polynucleotide, the method comprising:
   (A) contacting a solid support with the circular template polynucleotide and amplifying the circular template polynucleotide by extending a first amplification primer hybridized to said circular template polynucleotide with a strand-displacing polymerase to generate a first immobilized extension product comprising one or more complements of the circular template polynucleotide, wherein said first amplification primer is immobilized to the solid support;
   (B) hybridizing a first sequencing primer to the first immobilized extension product, and extending the first sequencing primer to generate a first sequencing read;
   (C) hybridizing the first immobilized extension product to a second amplification primer and extending with a polymerase to generate a second immobilized extension product comprising one or more complements of the first immobilized extension product, wherein the second amplification primer is immobilized to the solid support; and
   (D) hybridizing a second sequencing primer to the second extension product, and extending the second sequencing primer to generate a second sequencing read.

2. A method of sequencing a circular template polynucleotide in situ, the method comprising:
   (A) amplifying the circular template polynucleotide in a cell by extending a first immobilized amplification primer hybridized to said circular template polynucleotide with a strand-displacing polymerase to generate a first immobilized extension product comprising one or more complements of the circular template polynucleotide, wherein said first amplification primer is immobilized to a cellular component or a matrix within the cell;
   (B) hybridizing a first sequencing primer to the first immobilized extension product, and extending the first sequencing primer to generate a first sequencing read;
   (C) hybridizing the first extension product to a second immobilized amplification primer and extending with a polymerase to generate a second immobilized extension product comprising one or more complements of the first extension product, wherein the second amplification primer is immobilized to a cellular component or a matrix within the cell; and
   (D) hybridizing a second sequencing primer to the second immobilized extension product, and extending the second sequencing primer to generate a second sequencing read.

3. The method of claim 1, wherein the first extension product strand is cleaved after generating the first sequencing read but before generating the second sequencing read.

4. The method of claim 1, wherein (i) generating the first sequencing read comprises extending two or more first sequencing primers hybridized to the first extension product, and/or (ii) generating the second sequencing read comprises extending two or more second sequencing primers hybridized to the second extension product.

5. The method of claim 1, wherein the circular template polynucleotide comprises primer binding sequences that are complementary to one or more immobilized primers.

6. The method of claim 1, wherein amplifying the circular template polynucleotide comprises rolling circle amplification (RCA), exponential rolling circle amplification (eRCA), hyperbranched rolling circle amplification (HRCA), loop-mediated isothermal amplification (LAMP), or multiple displacement amplification (MDA).

7. The method of claim 6, wherein amplifying the circular template polynucleotide comprises rolling circle amplification (RCA) or exponential rolling circle amplification (eRCA).

8. The method of claim 6, wherein amplifying the circular template polynucleotide comprises hyperbranched rolling circle amplification (HRCA).

9. The method of claim 1, wherein the circular template polynucleotide is single-stranded DNA.

10. The method of claim 1, wherein prior to hybridizing the first and second sequencing primers, said method further comprises amplifying the first extension product or a complement thereof with a plurality of primers attached to the solid support, wherein the plurality of primers comprise a first plurality of primers comprising a complementary sequence to the first extension product and a second plurality of primers comprising a complementary sequence to a complement of the first extension product, and the amplifying comprises a plurality of cycles of strand denaturation, primer hybridization, and primer extension.

11. The method of claim 1, wherein the first extension product comprises at least one cleavable site.

12. The method of claim 11, wherein the at least one cleavable site comprises deoxyuracil triphosphate (dUTP).

13. The method of claim 10, wherein amplifying the first extension product further comprises extension of a 3' end of the first extension product hybridized to itself.

14. The method of claim 1, further comprising forming the circular template polynucleotide by ligating the ends of a linear polynucleotide together or by ligating hairpin adapters to both ends of a linear polynucleotide.

15. The method of claim 1, wherein the step of extending the first amplification primer comprises incubation with the strand-displacing polymerase (i) for about 10 seconds to about 30 minutes, and/or (ii) at a temperature of about 20° C. to about 50° C.

16. The method of claim 15, wherein prior to extending the first amplification primer, the strand-displacing polymerase contacts the first amplification primer and circular template polynucleotide in the absence of dNTPs; and optionally, any excess strand-displacing polymerase is removed.

17. The method of claim 10, wherein amplifying the first extension product or a complement thereof comprises an initial denaturation at about 85° C.-95° C. for about 1 minutes to about 10 minutes.

18. The method of claim 10, wherein the plurality of cycles comprises thermally cycling between (i) about 85° C.-95° C. for about 15-30 sec for denaturation, and (ii) about 65° C. for about 30 seconds for annealing/extension of the primer.

19. The method of claim 10, wherein amplifying the first extension product comprises a plurality of fluidic cycles of strand denaturation using a chemical denaturant, and a plurality of fluidic cycles of primer extension comprising an extension mixture.

20. The method of claim 10, wherein the circular template polynucleotide is about 100 to about 1000 nucleotides in length, about 100 to about 300 nucleotides in length, about 300 to about 500 nucleotides in length, or about 500 to about 1000 nucleotides in length.

21. The method of claim 20, wherein the circular template polynucleotide includes at least one cleavable site.

22. The method of claim 10, further comprising hybridizing an invasion primer to the second extension product, and extending the invasion primer thereby generating a first invasion strand hybridized to the second extension product, wherein the invasion primer is not covalently attached to the solid support.

23. The method of claim 22, further comprising removing the first invasion strand; and hybridizing a second invasion primer to the first extension product, and extending the second invasion primer thereby generating a second invasion strand hybridized to the first extension product, wherein the second invasion primer is not covalently attached to the solid support; and generating a second sequencing read by hybridizing one or more second sequencing primers to the second extension product, and extending the one or more second sequencing primers.

24. The method of claim 22, wherein the invasion primer comprises a cleavable site.

25. The method of claim 24, further comprising cleaving the cleavable site in the invasion primer to generate a free 3' end within the invasion primer, removing the invasion strand, and generating a second sequencing read by extending the invasion primer.

26. A complex comprising:
(a) a first concatemer partially hybridized to a second concatemer, wherein (i) the first concatemer comprises multiple copies of a circular template polynucleotide and the second concatemer comprises multiple complementary copies of the circular template polynucleotide, and (ii) the first concatemer and second concatemer are both covalently attached to a solid support; and
(b) one or more first sequencing primer extension products hybridized to a single-stranded portion of the first concatemer, wherein the sequencing primer extension product comprises a nucleotide comprising a reversible terminator; and
(c) one or more polymerases.

27. The method of claim 1, wherein the 3' ends of the first extension product and second extension product each comprise a blocking moiety.

28. The method of claim 1, wherein a portion of first extension product hybridizes to a portion of the second extension product thereby forming a partially double-stranded amplification product.

29. The method of claim 2, wherein the circular template polynucleotide comprises a complement of an endogenous nucleic acid sequence.

30. The method of claim 1, wherein the solid support further comprises a polymer or hydrogel to which the first and second amplification primers are attached.

* * * * *

SEQUENCE LISTING

```
<160> NUMBER OF SEQ ID NOS: 7

<210> SEQ ID NO 1
<211> LENGTH: 12
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(12)

<400> SEQUENCE: 1
attcattcat tc                                                          12
```

```
<210> SEQ ID NO 2
<211> LENGTH: 12
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(12)

<400> SEQUENCE: 2
gaatgaatga at                                                         12

<210> SEQ ID NO 3
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(29)
<223> OTHER INFORMATION: n is a, c, g, or t
<220> FEATURE:
<221> NAME/KEY: misc_feature
<222> LOCATION: (30)..(31)
<220> FEATURE:
<221> NAME/KEY: misc_feature
<222> LOCATION: (32)..(56)
<223> OTHER INFORMATION: n is a, c, g, or t
<220> FEATURE:
<221> NAME/KEY: misc_feature
<222> LOCATION: (57)..(60)

<400> SEQUENCE: 3 ggacnnnnn nnnnnnnnnn nnnnnnnna annnnnnnnn nnnnnnnnnn nnnnnnaatg        60

<210> SEQ ID NO 4
<211> LENGTH: 60
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(29)
<223> OTHER INFORMATION: n is a, c, g, or t
<220> FEATURE:
<221> NAME/KEY: misc_feature
<222> LOCATION: (30)..(31)
<220> FEATURE:
<221> NAME/KEY: misc_feature
<222> LOCATION: (32)..(56)
<223> OTHER INFORMATION: n is a, c, g, or t
<220> FEATURE:
<221> NAME/KEY: misc_feature
<222> LOCATION: (57)..(60)

<400> SEQUENCE: 4 cctgnnnnn nnnnnnnnnn nnnnnnnnnt tnnnnnnnnn nnnnnnnnnn nnnnnnttac        60

<210> SEQ ID NO 5
<211> LENGTH: 60
<212> TYPE: DNA
<213> ORGANISM: Artificial Sequence
```

```
<220> FEATURE:
<223> OTHER INFORMATION: Synthetic polynucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(29)
<223> OTHER INFORMATION: n is a, c, g, or t
<220> FEATURE:
<221> NAME/KEY: misc_feature
<222> LOCATION: (30)..(31)
<220> FEATURE:
<221> NAME/KEY: misc_feature
<222> LOCATION: (32)..(56)
<223> OTHER INFORMATION: n is a, c, g, or t
<220> FEATURE:
<221> NAME/KEY: misc_feature
<222> LOCATION: (57)..(60)

<400> SEQUENCE: 5
cattnnnnnn nnnnnnnnnn nnnnnnnnnt tnnnnnnnnn nnnnnnnnnn nnnnnngtcc    60

<210> SEQ ID NO 6
<211> LENGTH: 180
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(29)
<223> OTHER INFORMATION: n is a, c, g, or t
<220> FEATURE:
<221> NAME/KEY: misc_feature
<222> LOCATION: (30)..(31)
<220> FEATURE:
<221> NAME/KEY: misc_feature
<222> LOCATION: (32)..(56)
<223> OTHER INFORMATION: n is a, c, g, or t
<220> FEATURE:
<221> NAME/KEY: misc_feature
<222> LOCATION: (57)..(60)
<220> FEATURE:
<221> NAME/KEY: misc_feature
<222> LOCATION: (61)..(64)
<220> FEATURE:
<221> NAME/KEY: misc_feature
<222> LOCATION: (65)..(89)
<223> OTHER INFORMATION: n is a, c, g, or t
<220> FEATURE:
<221> NAME/KEY: misc_feature
<222> LOCATION: (90)..(91)
<220> FEATURE:
<221> NAME/KEY: misc_feature
<222> LOCATION: (92)..(116)
<223> OTHER INFORMATION: n is a, c, g, or t
<220> FEATURE:
<221> NAME/KEY: misc_feature
<222> LOCATION: (117)..(120)
<220> FEATURE:
<221> NAME/KEY: misc_feature
<222> LOCATION: (121)..(124)
<220> FEATURE:
<221> NAME/KEY: misc_feature
<222> LOCATION: (125)..(149)
<223> OTHER INFORMATION: n is a, c, g, or t
<220> FEATURE:
<221> NAME/KEY: misc_feature
<222> LOCATION: (150)..(151)
<220> FEATURE:
<221> NAME/KEY: misc_feature
<222> LOCATION: (152)..(176)
<223> OTHER INFORMATION: n is a, c, g, or t
```

```
<220> FEATURE:
<221> NAME/KEY: misc_feature
<222> LOCATION: (177)..(180)

<400> SEQUENCE: 6
ggacnnnnnn nnnnnnnnnn nnnnnnnnna annnnnnnnn nnnnnnnnnn nnnnnnaatg      60
ggacnnnnnn nnnnnnnnnn nnnnnnnnna annnnnnnnn nnnnnnnnnn nnnnnnaatg     120
ggacnnnnnn nnnnnnnnnn nnnnnnnnna annnnnnnnn nnnnnnnnnn nnnnnnaatg     180

<210> SEQ ID NO 7
<211> LENGTH: 180
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(4)
<220> FEATURE:
<221> NAME/KEY: misc_feature
<222> LOCATION: (5)..(29)
<223> OTHER INFORMATION: n is a, c, g, or t
<220> FEATURE:
<221> NAME/KEY: misc_feature
<222> LOCATION: (30)..(31)
<220> FEATURE:
<221> NAME/KEY: misc_feature
<222> LOCATION: (32)..(56)
<223> OTHER INFORMATION: n is a, c, g, or t
<220> FEATURE:
<221> NAME/KEY: misc_feature
<222> LOCATION: (57)..(60)
<220> FEATURE:
<221> NAME/KEY: misc_feature
<222> LOCATION: (61)..(64)
<220> FEATURE:
<221> NAME/KEY: misc_feature
<222> LOCATION: (65)..(89)
<223> OTHER INFORMATION: n is a, c, g, or t
<220> FEATURE:
<221> NAME/KEY: misc_feature
<222> LOCATION: (90)..(91)
<220> FEATURE:
<221> NAME/KEY: misc_feature
<222> LOCATION: (92)..(116)
<223> OTHER INFORMATION: n is a, c, g, or t
<220> FEATURE:
<221> NAME/KEY: misc_feature
<222> LOCATION: (117)..(120)
<220> FEATURE:
<221> NAME/KEY: misc_feature
<222> LOCATION: (121)..(124)
<220> FEATURE:
<221> NAME/KEY: misc_feature
<222> LOCATION: (125)..(149)
<223> OTHER INFORMATION: n is a, c, g, or t
<220> FEATURE:
<221> NAME/KEY: misc_feature
<222> LOCATION: (150)..(151)
<220> FEATURE:
<221> NAME/KEY: misc_feature
<222> LOCATION: (152)..(176)
<223> OTHER INFORMATION: n is a, c, g, or t
<220> FEATURE:
<221> NAME/KEY: misc_feature
<222> LOCATION: (177)..(180)

<400> SEQUENCE: 7
cattnnnnnn nnnnnnnnnn nnnnnnnnnt tnnnnnnnnn nnnnnnnnnn nnnnnngtcc      60
cattnnnnnn nnnnnnnnnn nnnnnnnnnt tnnnnnnnnn nnnnnnnnnn nnnnnngtcc     120
cattnnnnnn nnnnnnnnnn nnnnnnnnnt tnnnnnnnnn nnnnnnnnnn nnnnnngtcc     180
```